United States Patent
Ohashi et al.

(10) Patent No.: US 9,221,742 B2
(45) Date of Patent: Dec. 29, 2015

(54) SULFONIUM SALT, CHEMICALLY AMPLIFIED RESIST COMPOSITION, AND PATTERN FORMING PROCESS

(71) Applicant: SHIN-ETSU CHEMICAL CO., LTD., Tokyo (JP)

(72) Inventors: Masaki Ohashi, Joetsu (JP); Masahiro Fukushima, Joetsu (JP); Tomohiro Kobayashi, Joetsu (JP); Ryosuke Taniguchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/481,324

(22) Filed: Sep. 9, 2014

(65) Prior Publication Data
US 2015/0086926 A1    Mar. 26, 2015

(30) Foreign Application Priority Data
Sep. 11, 2013   (JP) .................................. 2013-188086

(51) Int. Cl.
*G03F 7/004*   (2006.01)
*G03F 7/38*    (2006.01)
(Continued)

(52) U.S. Cl.
CPC .............. *C07C 69/753* (2013.01); *C07C 59/115* (2013.01); *C07C 69/63* (2013.01);
(Continued)

(58) Field of Classification Search
CPC .. C07C 69/753; C07C 69/635; C07C 69/757; G03F 7/004; G03F 7/2004; G03F 7/38
USPC ........ 560/117, 127; 430/270.1, 913, 322, 331
See application file for complete search history.

(56) References Cited

U.S. PATENT DOCUMENTS 5,650,483 A    7/1997   Malik et al.
5,777,151 A *  7/1998   Crochemore .................. 560/61
(Continued)

FOREIGN PATENT DOCUMENTS

JP    11-125907 A    5/1999
JP    11-327143 A    11/1999
(Continued)

OTHER PUBLICATIONS

Machine translation of JP 2002-148790 (no date).*

*Primary Examiner* — Amanda C Walke
(74) *Attorney, Agent, or Firm* — Westerman, Hattori, Daniels & Adrian, LLP

(57) ABSTRACT

A caboxylic acid sulfonium salt having formula (1) is provided wherein $R^0$ is hydrogen or a monovalent hydrocarbon group, $R^{01}$ and $R^{02}$ are hydrogen or a monovalent hydrocarbon group, at least one of $R^0$, $R^{01}$ and $R^{02}$ has a cyclic structure, L is a single bond or forms an ester, sulfonate, carbonate or carbamate bond with the vicinal oxygen atom, $R^2$, $R^3$ and $R^4$ are monovalent hydrocarbon groups. The sulfonium salt functions as a quencher in a resist composition, enabling to form a pattern of good profile with minimal LWR, rectangularity, and high resolution.

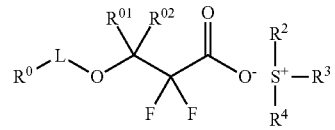

(1)

17 Claims, 14 Drawing Sheets

(51) Int. Cl.
*C07C 69/753* (2006.01)
*C07C 69/635* (2006.01)
*G03F 7/20* (2006.01)
*C07C 381/12* (2006.01)
*C07C 69/63* (2006.01)
*C07C 69/757* (2006.01)
*C07C 59/115* (2006.01)

(52) U.S. Cl.
CPC ............ *C07C 69/635* (2013.01); *C07C 69/757* (2013.01); *C07C 381/12* (2013.01); *G03F 7/004* (2013.01); *G03F 7/2004* (2013.01); *G03F 7/38* (2013.01); *C07C 2101/14* (2013.01); *C07C 2102/42* (2013.01); *C07C 2103/54* (2013.01)

(56) References Cited

U.S. PATENT DOCUMENTS

| | | | |
|---|---|---|---|
| 6,136,500 A | 10/2000 | Kobayashi et al. | |
| 6,312,867 B1 | 11/2001 | Kinsho et al. | |
| 6,485,883 B2 | 11/2002 | Kodama et al. | |
| 6,492,091 B2 * | 12/2002 | Kodama et al. | 430/270.1 |
| 6,830,866 B2 | 12/2004 | Kobayashi et al. | |
| 7,291,441 B2 * | 11/2007 | Sato | 430/270.1 |
| 7,511,169 B2 | 3/2009 | Ohsawa et al. | |
| 7,527,912 B2 | 5/2009 | Ohsawa et al. | |
| 7,537,880 B2 | 5/2009 | Harada et al. | |
| 7,598,016 B2 * | 10/2009 | Kobayashi et al. | 430/270.1 |
| 7,622,242 B2 | 11/2009 | Hatakeyama et al. | |
| 7,771,914 B2 | 8/2010 | Hatakeyama et al. | |
| 7,812,194 B2 * | 10/2010 | Kodama et al. | 568/28 |
| 7,858,289 B2 | 12/2010 | Yamashita | |
| 8,043,786 B2 * | 10/2011 | Ebata et al. | 430/270.1 |
| 8,057,981 B2 | 11/2011 | Harada et al. | |
| 8,057,985 B2 | 11/2011 | Ohashi et al. | |
| 8,101,335 B2 | 1/2012 | Harada et al. | |
| 8,114,570 B2 | 2/2012 | Ohsawa et al. | |
| 8,114,571 B2 | 2/2012 | Ohashi et al. | |
| 8,173,354 B2 | 5/2012 | Ohsawa et al. | |
| 8,252,504 B2 | 8/2012 | Harada et al. | |
| 8,268,528 B2 | 9/2012 | Harada et al. | |
| 8,283,104 B2 | 10/2012 | Ohashi et al. | |
| 8,349,533 B2 | 1/2013 | Ohsawa et al. | |
| 8,426,106 B2 * | 4/2013 | Masuyama et al. | 430/270.1 |
| 8,431,323 B2 | 4/2013 | Watanabe et al. | |
| 8,435,717 B2 | 5/2013 | Hagiwara et al. | |
| 8,632,939 B2 * | 1/2014 | Masunaga et al. | 430/270.1 |
| 8,691,490 B2 * | 4/2014 | Ohashi et al. | 430/270.1 |
| 8,697,903 B2 | 4/2014 | Kinsho et al. | |
| 8,795,948 B2 * | 8/2014 | Dazai et al. | 430/270.1 |
| 8,815,492 B2 * | 8/2014 | Ohsawa et al. | 430/270.1 |
| 8,835,095 B2 * | 9/2014 | Ichikawa et al. | 430/270.1 |
| 8,952,204 B2 * | 2/2015 | Kinoshita et al. | 568/633 |
| 8,980,524 B2 * | 3/2015 | Hirano et al. | 430/270.1 |
| 2009/0233223 A1 * | 9/2009 | Tachibana et al. | 430/270.1 |
| 2009/0269696 A1 * | 10/2009 | Ohsawa et al. | 430/270.1 |
| 2010/0099042 A1 * | 4/2010 | Ohashi et al. | 430/270.1 |
| 2011/0212391 A1 * | 9/2011 | Masunaga et al. | 430/5 |
| 2012/0135351 A1 * | 5/2012 | Ichikawa et al. | 430/285.1 |
| 2012/0288796 A1 * | 11/2012 | Katayama et al. | 430/285.1 |
| 2013/0157197 A1 * | 6/2013 | Komuro et al. | 430/285.1 |
| 2013/0177852 A1 * | 7/2013 | Yoon et al. | 430/285.1 |
| 2013/0224658 A1 * | 8/2013 | Komuro et al. | 430/281.1 |
| 2014/0164864 A1 | 6/2014 | Takeda et al. | |

FOREIGN PATENT DOCUMENTS

| | | | |
|---|---|---|---|
| JP | 2000-336121 A | | 12/2000 |
| JP | 2001-281849 A | | 10/2001 |
| JP | 2002148790 A | * | 5/2002 |
| JP | 2003-66612 A | | 3/2003 |
| JP | 2005274647 A | * | 10/2005 |
| JP | 2007-145797 A | | 6/2007 |
| JP | 2008-106045 A | | 5/2008 |
| JP | 2008-111103 A | | 5/2008 |
| JP | 2008-122932 A | | 5/2008 |
| JP | 2008-281980 A | | 11/2008 |
| JP | 2009-7327 A | | 1/2009 |
| JP | 4226803 B2 | | 2/2009 |
| JP | 2009-98638 A | | 5/2009 |
| JP | 2009-109595 A | | 5/2009 |
| JP | 2009-191151 A | | 8/2009 |
| JP | 2009-192784 A | | 8/2009 |
| JP | 2009-258695 A | | 11/2009 |
| JP | 2009-269953 A | | 11/2009 |
| JP | 2009-276363 A | | 11/2009 |
| JP | 2010-77404 A | | 4/2010 |
| JP | 2010-107695 A | | 5/2010 |
| JP | 2010-113209 A | | 5/2010 |
| JP | 2010-134012 A | | 6/2010 |
| JP | 2010-215608 A | | 9/2010 |
| JP | 2011-16746 A | | 1/2011 |
| JP | 201142789 A | | 3/2011 |
| JP | 2011-250105 A | | 12/2011 |
| JP | 2012-46501 A | | 3/2012 |
| JP | 2012-97256 A | | 5/2012 |
| JP | 2012-108447 A | | 6/2012 |
| WO | 2011/149015 A1 | | 12/2011 |

* cited by examiner

US 9,221,742 B2

SULFONIUM SALT, CHEMICALLY AMPLIFIED RESIST COMPOSITION, AND PATTERN FORMING PROCESS

CROSS-REFERENCE TO RELATED APPLICATION

This non-provisional application claims priority under 35 U.S.C. §119(a) on Patent Application No. 2013-188086 filed in Japan on Sep. 11, 2013, the entire contents of which are hereby incorporated by reference.

TECHNICAL FIELD

This invention relates to a carboxylic acid sulfonium salt of specific structure, a chemically amplified resist composition comprising the salt, and a pattern forming process using the resist composition.

BACKGROUND ART

While a number of recent efforts are being made to achieve a finer pattern rule in the drive for higher integration densities and operating speeds in LSI devices, DUV and EUV lithography is thought to hold particular promise as the next generation in microfabrication technology. In particular, photolithography using an ArF excimer laser as the light source is thought requisite to the micropatterning technique capable of achieving a feature size of 0.13 μm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. While the ArF immersion lithography has entered the commercial stage, the technology still needs a resist material which is substantially non-leachable in water.

In the ArF lithography (193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polyacrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in enhancing the transparency of a resin alone.

Studies have also been made on photoacid generators (PAGs) and diffusion inhibitors. Sulfonium salts such as triphenylsulfonium nonafuorobutanesulfonate are typically used as the PAG because of stability in resist compositions. Amines are typically used as the diffusion inhibitor. Many problems associated with line width roughness (LWR) as an index of pattern roughness and pattern profile are left unsolved. Also use of weak acid onium salts as the diffusion inhibitor is under study. For example, JP-A H11-125907 describes that patterns with minimal roughness can be formed using a compound capable of generating a carboxylic acid having a boiling point of at least 150° C. JP-A H11-327143 reports improvements in sensitivity, resolution and exposure margin by the addition of sulfonic acid ammonium salts or carboxylic acid ammonium salts. Also, JP-A 2001-281849 describes that a resist composition for KrF or EB lithography comprising a PAG capable of generating a fluorinated carboxylic acid is improved in resolution and process latitude such as exposure margin and depth of focus. Further, JP 4226803 describes a positive photosensitive composition for ArF excimer laser lithography comprising a carboxylic acid onium salt. These systems are based on the mechanism that a salt exchange occurs between a weak acid onium salt and a strong acid (sulfonic acid) generated by another PAG upon exposure, to form a weak acid and a strong acid onium salt. That is, the strong acid ($\alpha,\alpha$-difluorosulfonic acid) having high acidity is replaced by a weak acid (alkanesulfonic acid or carboxylic acid), thereby suppressing acid-aided decomposition reaction of acid labile group and reducing or controlling the distance of acid diffusion. The onium salt apparently functions as a quencher, that is, diffusion inhibitor. However, as the microfabrication technology is currently further advanced, the resist compositions using such weak acid onium salts become unsatisfactory with respect to resolution, roughness, depth of focus and the like, particularly when processed by the ArF immersion lithography. The alkanesulfonic acid salts have a low quencher capability because the acidity is not fully low. The carboxylic acid salts are not only insufficient in the above-referred properties, but also suffer from a leaching problem because they are highly hydrophilic. That is, the salts can be leached in immersion water used in the ArF immersion lithography. Since this leaching has a concern of contaminating the exposure tool and can also cause defects, it is desired to minimize the leaching.

JP-A 2012-108447 discloses an onium salt of fluoroalkanesulfonamide as the weak acid onium salt. When this onium salt is applied to the upcoming generation of ultrafine processing using ArF lithography or ArF immersion lithography, the line width roughness (LWR), indicative of pattern roughness, and resolution are yet short. There is still a need for a weak acid onium salt having improved quencher function.

CITATION LIST

Patent Document 1: JP-A H11-125907 (U.S. Pat. No. 6,136,500)
Patent Document 2: JP-A H11-327143
Patent Document 3: JP-A 2001-281849 (U.S. Pat. No. 6,485,883)
Patent Document 4: JP 4226803 (U.S. Pat. No. 6,492,091)
Patent Document 6: JP-A 2012-108447

DISCLOSURE OF INVENTION

An object of the invention is to provide a chemically amplified resist composition which is processed by DUV lithography and EUV lithography to form a resist pattern with improved resolution, reduced LWR and minimal defects after development, and a pattern forming process using the resist composition.

The inventors have found that a resist composition comprising a carboxylic acid sulfonium salt of specific structure can be processed by lithography to form a resist pattern with improved resolution, reduced LWR and minimal defects after development, and is suited for high accuracy micropatterning.

In one aspect, the invention provides a sulfonium salt having the general formula (1).

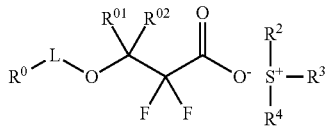

(1)

Herein $R^0$ is hydrogen, or a straight $C_1$-$C_{20}$ or branched or cyclic $C_3$-$C_{20}$ monovalent hydrocarbon group which may be substituted with or separated by a heteroatom; $R^{01}$ and $R^{02}$ are each independently hydrogen, or a straight $C_1$-$C_{20}$ or branched or cyclic $C_3$-$C_{20}$ monovalent hydrocarbon group which may be substituted with or separated by a heteroatom, or $R^{01}$ and $R^{02}$ may bond together to form a ring with the carbon atom to which they are attached, with the proviso that at least one of $R^0$, $R^{01}$ and $R^{02}$ has a cyclic structure; L is a single bond or forms an ester bond, sulfonate bond, carbonate bond or carbamate bond with the vicinal oxygen atom; $R^2$, $R^3$ and $R^4$ are each independently a straight $C_1$-$C_{20}$ or branched or cyclic $C_3$-$C_{20}$ monovalent hydrocarbon group which may be substituted with or separated by a heteroatom, at least two of $R^2$, $R^3$ and $R^4$ may bond together to form a ring with the sulfur atom in the formula.

In a preferred embodiment, the anion moiety of the formula:

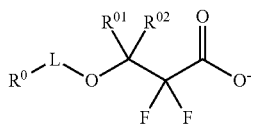

is selected from the following formulae (A-9) to (A-16), (A-27) to (A-34), (A-44) to (A-50), (A-52), and (A-53).

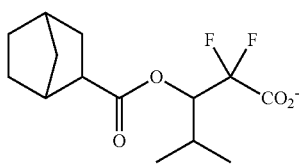

(A-9)

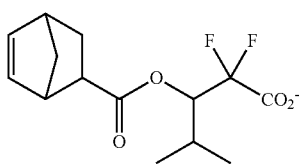

(A-10)

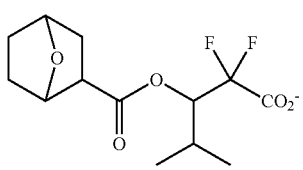

(A-11)

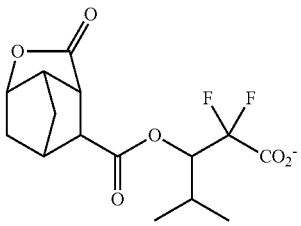

(A-12)

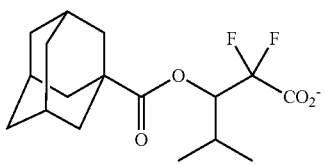

(A-13)

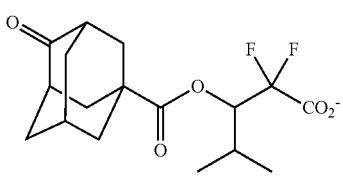

(A-14)

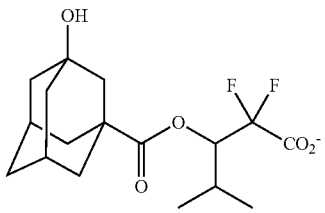

(A-15)

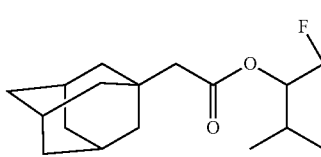

(A-16)

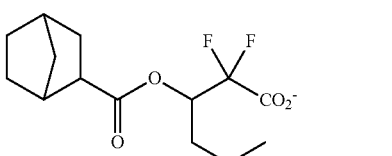

(A-27)

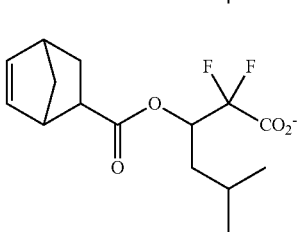

(A-28)

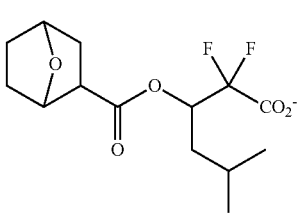

(A-29)

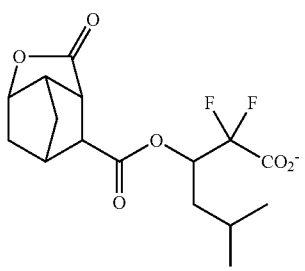
(A-30)
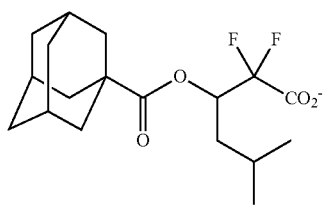
(A-31)
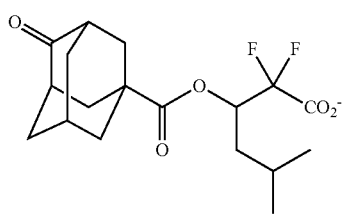
(A-32)
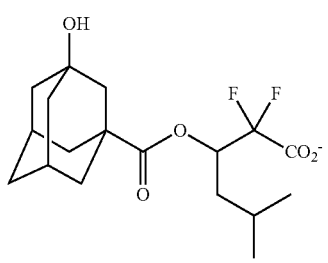
(A-33)
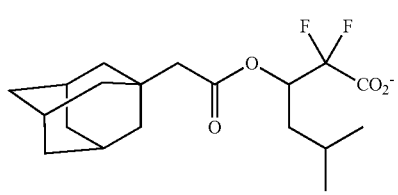
(A-34)
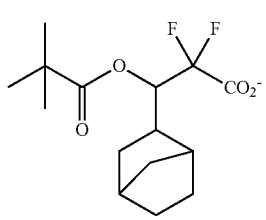
(A-44)
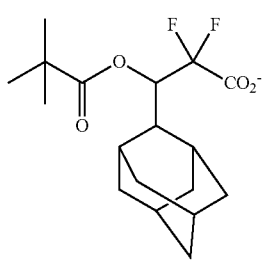
(A-45)
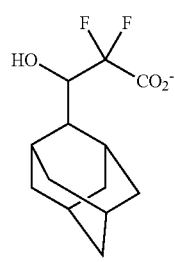
(A-46)
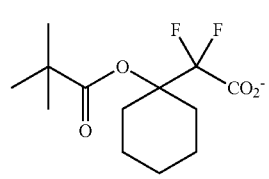
(A-47)
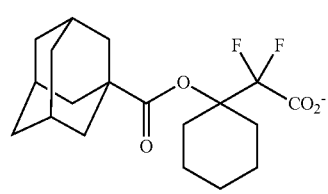
(A-48)
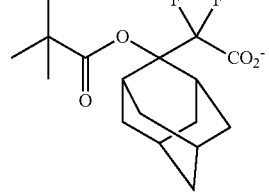
(A-49)
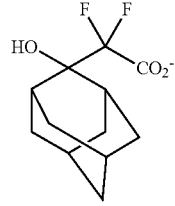
(A-50)
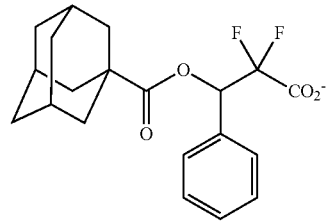
(A-52)
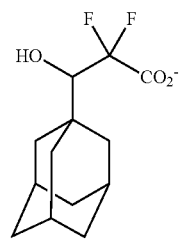
(A-53)

In a preferred embodiment, the cation moiety of the formula:
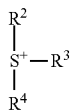
is selected from the following formulae.
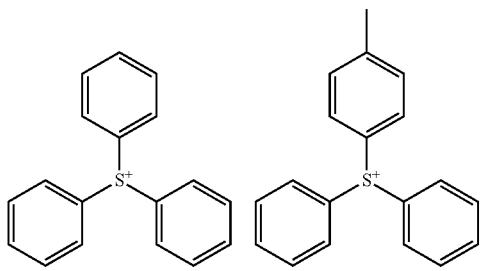
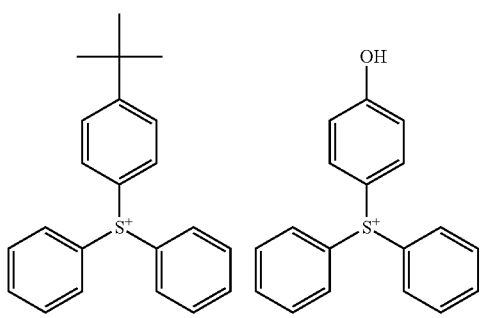
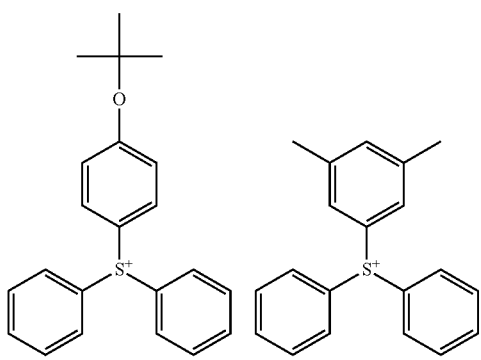
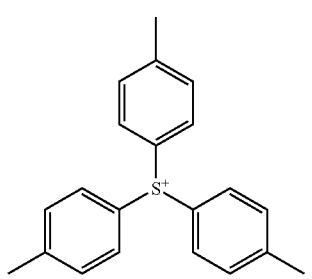
-continued
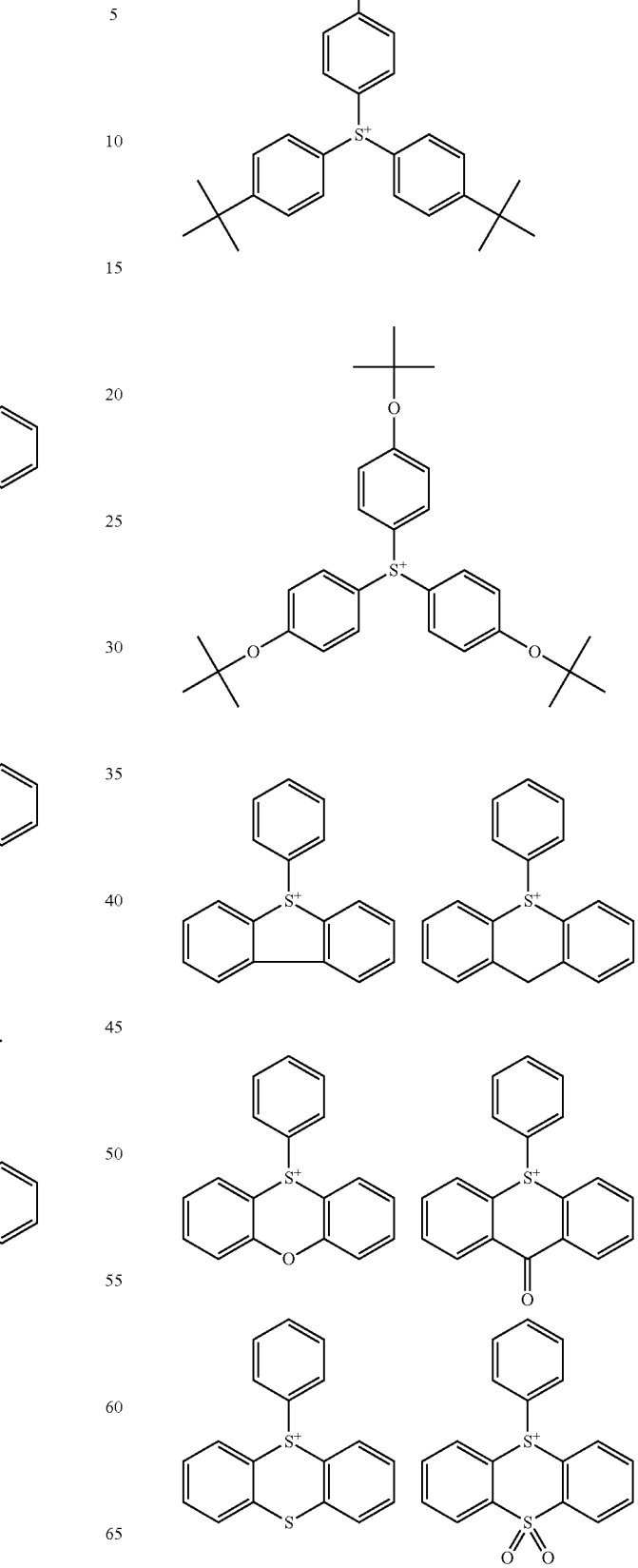

-continued

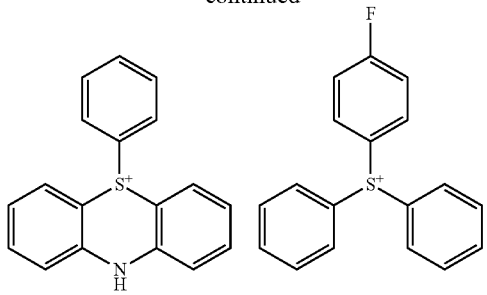

In another aspect, the invention provides a chemically amplified resist composition comprising (A) the sulfonium salt defined above, (B) a polymer as a base resin, and (E) an organic solvent, the polymer comprising recurring units having the general formulae (2) and (3).

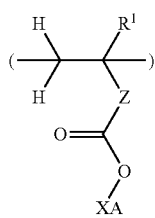 (2)

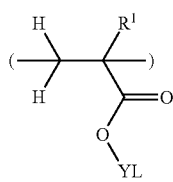 (3)

Herein $R^1$ is hydrogen, fluorine, methyl or trifluoromethyl, Z is a single bond, phenylene, naphthylene or (backbone)-C(=O)—O—Z'—, Z' is a straight $C_1$-$C_{10}$ or branched or cyclic $C_3$-$C_{10}$ alkylene group which may contain a hydroxyl radical, ether bond, ester bond, or lactone ring, or a phenylene or naphthylene group, XA is an acid labile group, and YL is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

In a preferred embodiment, the polymer further comprises recurring units (d1) or (d2) having the general formula below.

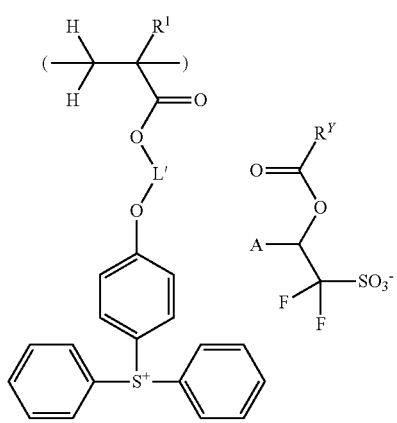 (d1)

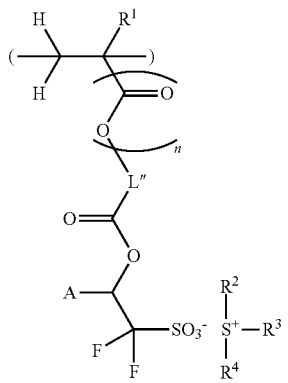 (d2)

Herein $R^1$, $R^2$, $R^3$, and $R^4$ are as defined above, L' is a single bond or $C_2$-$C_5$ alkylene group, $R^Y$ is a straight $C_1$-$C_{20}$ or branched or cyclic $C_3$-$C_{20}$ monovalent hydrocarbon group which may be substituted with or separated by a heteroatom, A is hydrogen or trifluoromethyl, L" is a single bond or a straight $C_1$-$C_{20}$ or branched or cyclic $C_3$-$C_{20}$ divalent hydrocarbon group which may be substituted with or separated by a heteroatom, n is 0 or 1, with the proviso that n is 0 when L" is a single bond.

The resist composition is typically a chemically amplified resist composition further comprising a photoacid generator having the general formula (4).

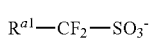 (4)

Herein $R^2$, $R^3$, and $R^4$ are as defined above, $X^-$ is an anion of any one of the general formulae (5) to (8):

 (5) (6)

 (7)

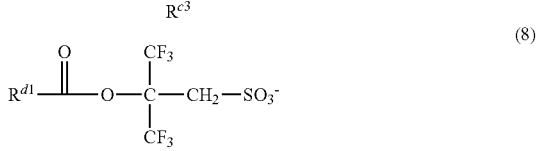 (8)

wherein $R^{a1}$, $R^{b1}$, $R^{b2}$, $R^{c1}$, $R^{c2}$, and $R^{c3}$ are each independently fluorine or a straight $C_1$-$C_{40}$ or branched or cyclic $C_3$-$C_{40}$ monovalent hydrocarbon group which may be substituted with or separated by a heteroatom, $R^{b1}$ and $R^{b2}$, or $R^{c1}$ and $R^{c2}$ may bond together to form a ring with —$CF_2$—$SO_2$— group to which they are attached, $R^{d1}$ is a straight $C_1$-$C_{40}$ or branched or cyclic $C_3$-$C_{40}$ monovalent hydrocarbon group which may be substituted with or separated by a heteroatom.

The resist composition may further comprise a nitrogen-containing compound, and optionally a surfactant which is insoluble in water and soluble in alkaline developer.

In a further aspect, the invention provides a pattern forming process comprising the steps of applying the chemically amplified resist composition defined above onto a substrate, prebaking to form a resist film, exposing the resist film to KrF excimer laser, ArF excimer laser or EUV through a photomask, baking, and developing the exposed resist film in a developer.

In a preferred embodiment, the exposing step is by immersion lithography wherein a liquid having a refractive index of at least 1.0 is interposed between the resist film and a projection lens. In the immersion lithography, preferably a protective film is formed on the resist film, and the liquid is interposed between the protective film and the projection lens.

ADVANTAGEOUS EFFECTS OF INVENTION

Since the carboxylic acid sulfonium salt exerts a satisfactory quencher (or diffusion control) function, the inventive resist composition comprising the same enables to form a pattern of good profile with a high resolution, low LWR, and improved rectangularity. When the resist composition is applied to the ArF immersion lithography, it has advantages including least leaching in immersion water and minimal development defects.

BRIEF DESCRIPTION OF ACCOMPANYING DRAWINGS

DESCRIPTION OF EMBODIMENTS

Figure 1:
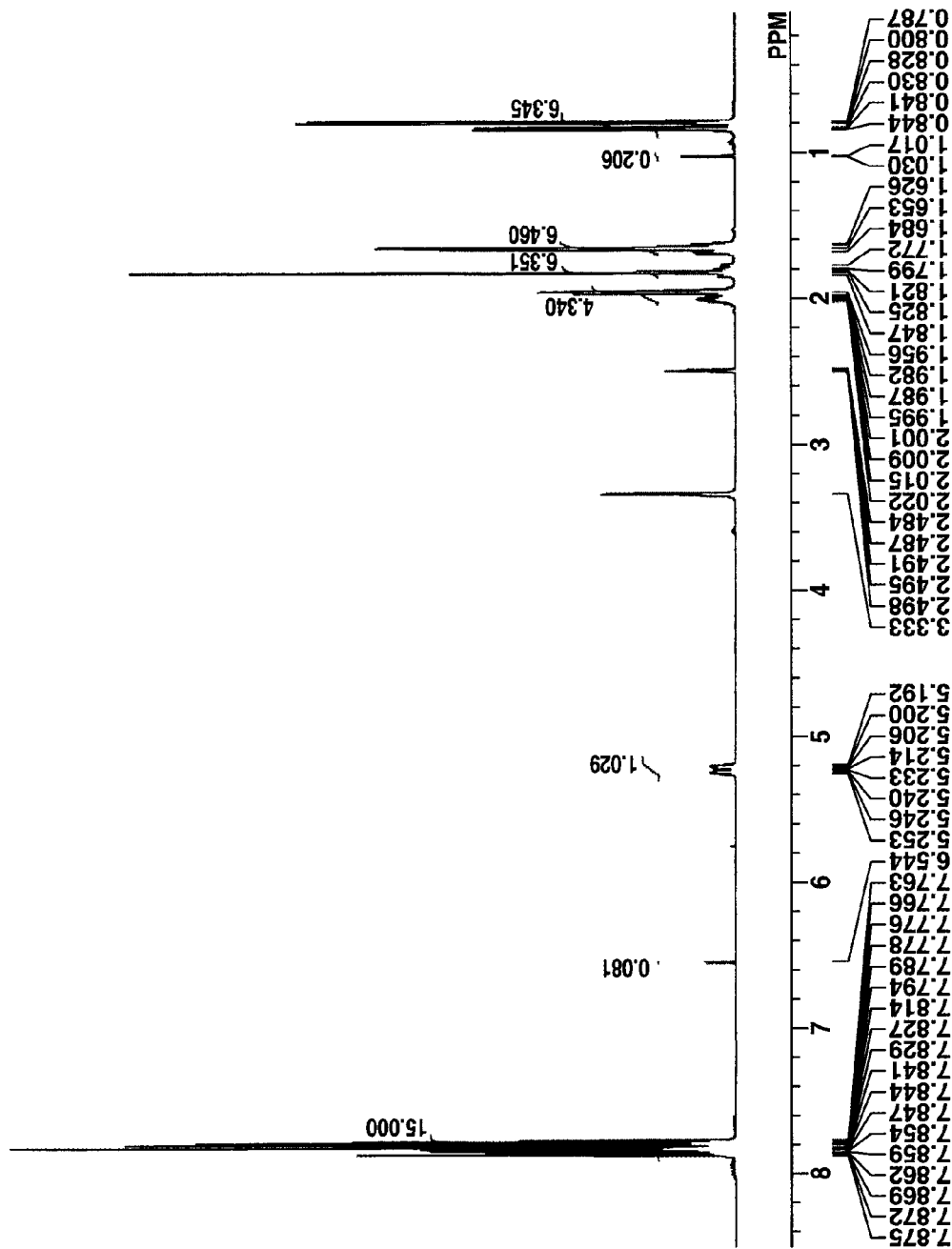
FIG. 1 is a diagram of $^1$H-NMR spectrum of the compound obtained in Synthesis Example 1-2.

As used herein, the singular forms "a," "an" and "the" include plural referents unless the context clearly dictates otherwise. The notation (Cn-Cm) means a group containing from n to m carbon atoms per group.

The abbreviations and acronyms have the following meaning.
DUV: deep ultraviolet
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness In structural formulae, the broken line indicates a valence bond; Ph stands for phenyl and Ac for acetyl.

(A) Sulfonium Salt

One embodiment of the invention is a carboxylic acid sulfonium salt having the general formula (1).

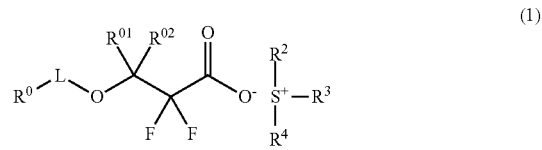

(1)

Herein $R^0$ is hydrogen, or a straight $C_1$-$C_{20}$ or branched or cyclic $C_3$-$C_{20}$ monovalent hydrocarbon group which may be substituted with or separated by a heteroatom. $R^{01}$ and $R^{02}$ are each independently hydrogen, or a straight $C_1$-$C_{20}$ or branched or cyclic $C_3$-$C_{20}$ monovalent hydrocarbon group which may be substituted with or separated by a heteroatom, or $R^{01}$ and $R^{02}$ may bond together to form a ring with the carbon atom to which they are attached, with the proviso that at least one of $R^0$, $R^{01}$ and $R^{02}$ has a cyclic structure. L is a single bond or forms an ester, sulfonate, carbonate or carbamate bond with the vicinal oxygen atom. $R^2$, $R^3$ and $R^4$ are each independently a straight $C_1$-$C_{20}$ or branched or cyclic $C_3$-$C_{20}$ monovalent hydrocarbon group which may be substituted with or separated by a heteroatom, at least two of $R^2$, $R^3$ and $R^4$ may bond together to form a ring with the sulfur atom in the formula.

In formula (1), $R^0$ is hydrogen, or a straight $C_1$-$C_{20}$ or branched or cyclic $C_3$-$C_{20}$ monovalent hydrocarbon group which may be substituted with or separated by a heteroatom. Specifically, suitable monovalent hydrocarbon groups include methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, adamantylmethyl, phenyl, naphthyl, and anthracenyl. In these groups, one or more hydrogen atom may be replaced by a heteroatom such as oxygen, sulfur, nitrogen, or halogen, or a heteroatom such as oxygen, sulfur or nitrogen may intervene, and as a result, a hydroxyl group, cyano group, carbonyl group, ether bond, ester bond, sulfonate (sulfonic acid ester) bond, carbonate bond, lactone ring, sultone ring, carboxylic anhydride or haloalkyl group may form or intervene.

In formula (1), $R^{01}$ and $R^{02}$ are each independently hydrogen, or a straight $C_1$-$C_{20}$ or branched or cyclic $C_3$-$C_{20}$ monovalent hydrocarbon group which may be substituted with or separated by a heteroatom. Also, $R^{01}$ and $R^{02}$ may bond together to form a ring with the carbon atom to which they are attached. Specifically, suitable monovalent hydrocarbon groups are as exemplified for R⁰. When $R^{01}$ and $R^{02}$ bond together to form a ring with the carbon atom to which they are attached, suitable cyclic substituent groups thus formed include cyclopentyl, cyclohexyl, norbornyl and adamantyl. In these groups, one or more hydrogen atom may be replaced by a heteroatom such as oxygen, sulfur, nitrogen, or halogen, or a heteroatom such as oxygen, sulfur or nitrogen may intervene, and as a result, a hydroxyl group, cyano group, carbonyl group, ether bond, ester bond, sulfonate bond, carbonate bond, lactone ring, sultone ring, carboxylic anhydride or haloalkyl group may form or intervene.

It is noted that at least one of $R^0$, $R^{01}$ and $R^{02}$ has a cyclic structure. Suitable cyclic groups include cyclopentyl, cyclohexyl, norbornyl, tricyclo[5.2.1.0²,⁶]decanyl, adamantyl, phenyl, naphthyl, and anthracenyl. In these groups, one or more hydrogen atom may be replaced by a heteroatom such as oxygen, sulfur, nitrogen, or halogen, or a heteroatom such as oxygen, sulfur or nitrogen may intervene, and as a result, a hydroxyl group, cyano group, carbonyl group, ether bond, ester bond, sulfonate bond, carbonate bond, lactone ring, sultone ring, carboxylic anhydride or haloalkyl group may form or intervene. Of the cyclic groups exemplified above, aliphatic hydrocarbon groups are preferred.

In formula (1), L is a single bond or forms an ester bond, sulfonate (sulfonic acid ester) bond, carbonate bond or carbamate bond with the vicinal oxygen atom.

Preferred structures for the anion moiety of the sulfonium salt having formula (1) are shown below although the invention is not limited thereto. Sulfonium salts having these structures as the anion have properly controlled hydrophilicity despite carboxylic acid salts and are least leachable in water during immersion lithography.

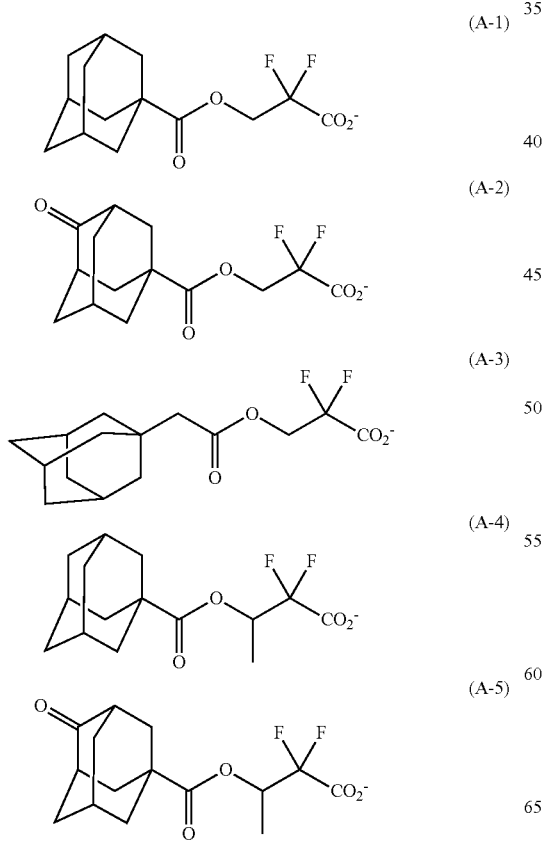

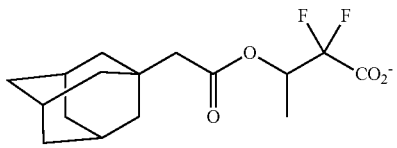

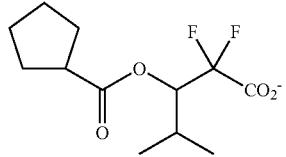

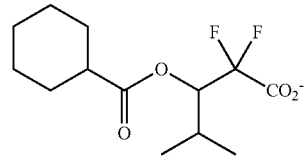

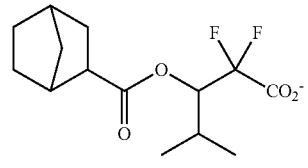

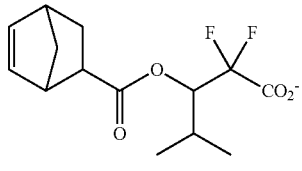

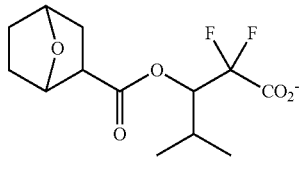

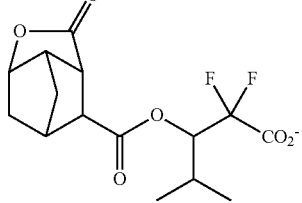

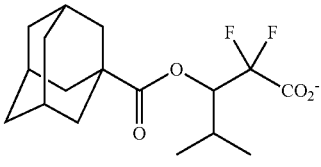

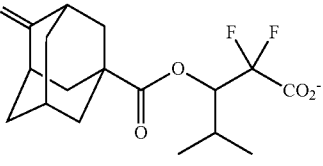

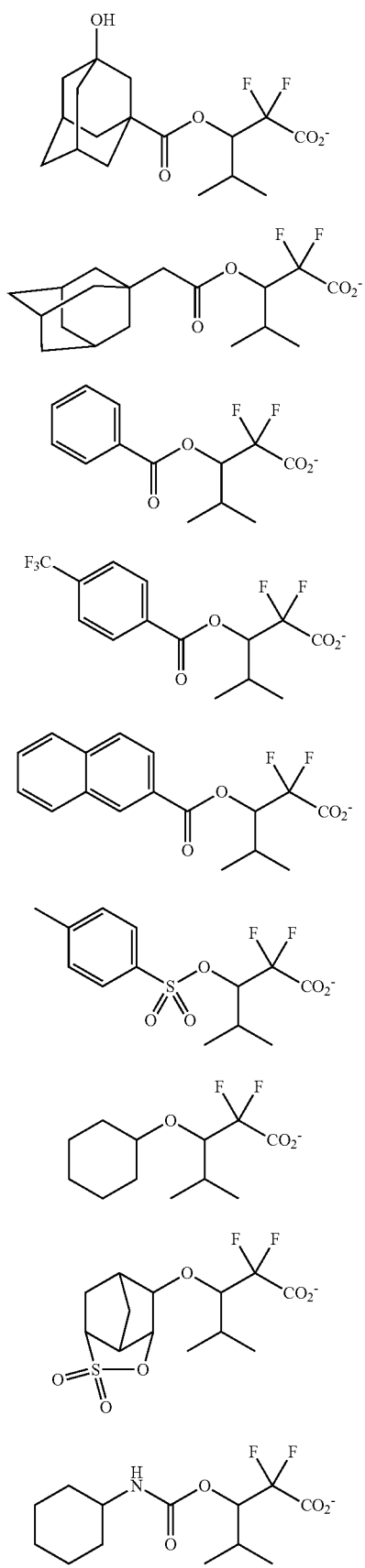
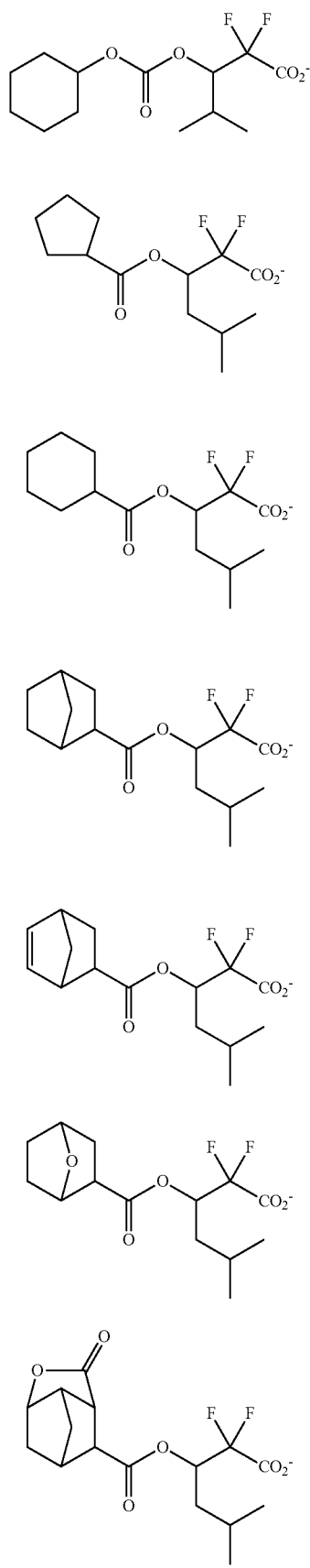

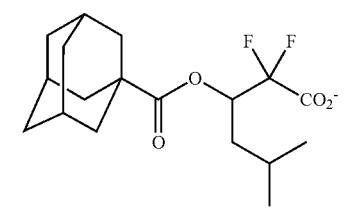
(A-31)
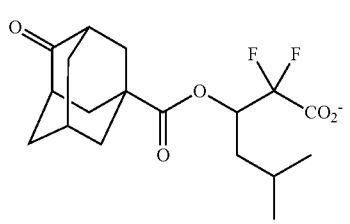
(A-32)
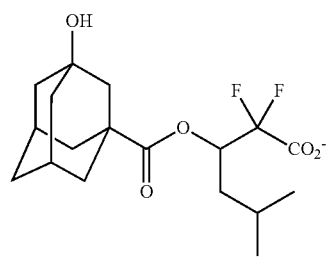
(A-33)
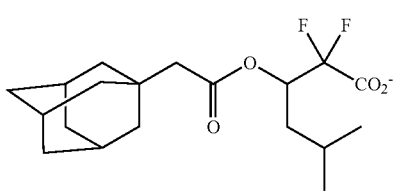
(A-34)
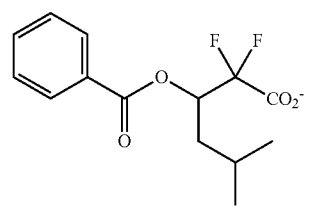
(A-35)
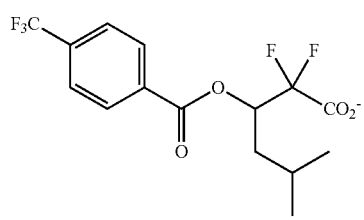
(A-36)
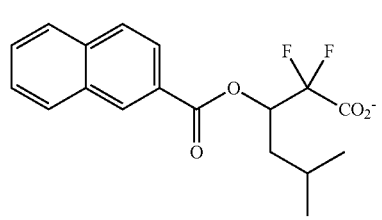
(A-37)
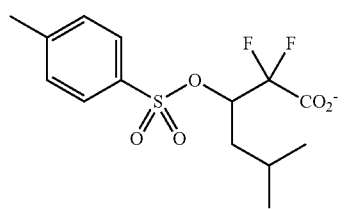
(A-38)
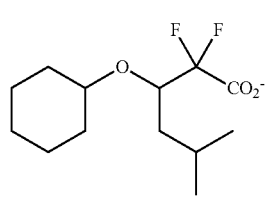
(A-39)
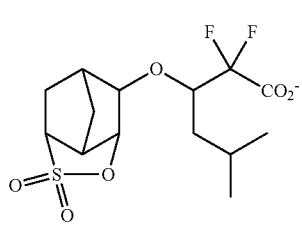
(A-40)
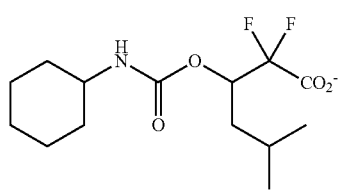
(A-41)
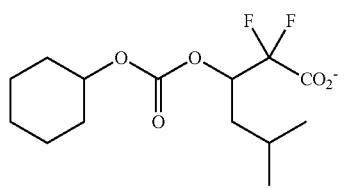
(A-42)
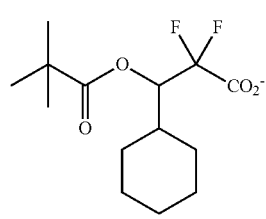
(A-43)
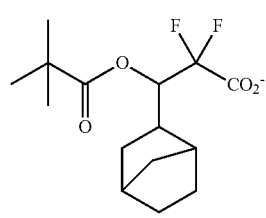
(A-44)

(A-45) 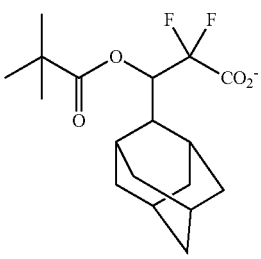

(A-46) 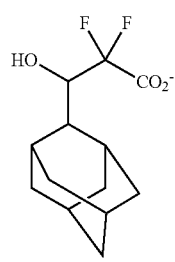

(A-47) 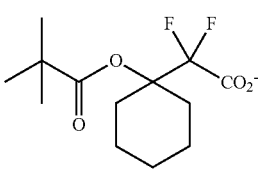

(A-48) 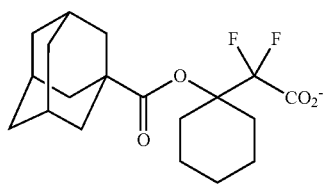

(A-49) 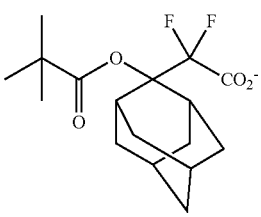

(A-50) 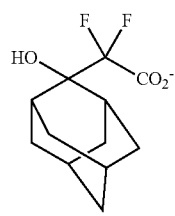

(A-51) 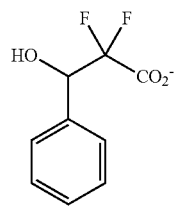

(A-52) 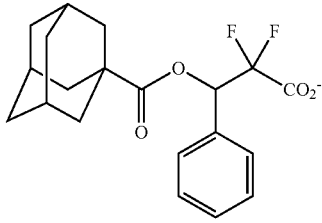

(A-53) 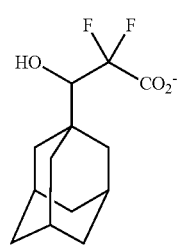

More preferred as the anion moiety of the sulfonium salt are the structures of formulae (A-9) to (A-16), (A-27) to (A-34), (A-44) to (A-50), (A-52), and (A-53). Sulfonium salts having these structures as the anion have high lipophilicity despite carboxylic acid salts and are least leachable in water during immersion lithography. Since acid diffusion is reduced because of the robust bicyclo structure, they are best suited for use in resist compositions.

In formula (1), $R^2$, $R^3$ and $R^4$ are each independently a straight $C_1$-$C_{20}$ or branched or cyclic $C_3$-$C_{20}$ monovalent hydrocarbon group which may be substituted with or separated by a heteroatom. Also, any two or more of $R^2$, $R^3$ and $R^4$ may bond together to form a ring with the sulfur atom in the formula. Suitable monovalent hydrocarbon groups include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl, hexenyl, and cyclohexenyl; aryl groups such as phenyl, naphthyl, and thienyl; and aralkyl groups such as benzyl, 1-phenylethyl and 2-phenylethyl; with the aryl groups being preferred. In these groups, one or more hydrogen atom may be replaced by a heteroatom such as oxygen, sulfur, nitrogen, or halogen, or a heteroatom such as oxygen, sulfur or nitrogen may intervene, and as a result, a hydroxyl group, cyano group, carbonyl group, ether bond, ester bond, sulfonate (sulfonic acid ester) bond, carbonate bond, lactone ring, sultone ring, carboxylic anhydride or haloalkyl group may form or intervene.

Any two or more of $R^2$, $R^3$ and $R^4$ may bond together to form a ring with the sulfur atom in formula (1). In this case, exemplary cyclic structures are shown below.

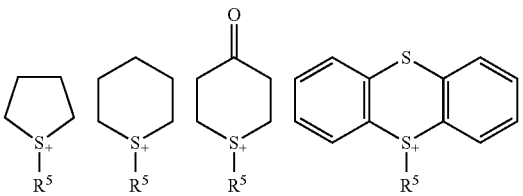

-continued
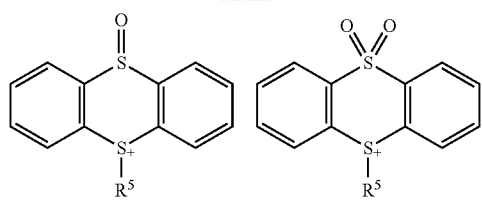
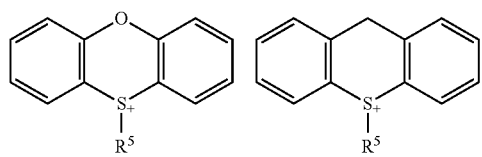
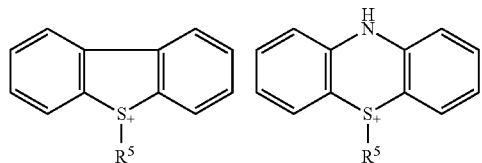
Herein, R⁵ is a group as exemplified above for $R^2$, $R^3$ and $R^4$.
Preferred structures for the cation moiety of the sulfonium salt having formula (1) are shown below although the invention is not limited thereto.
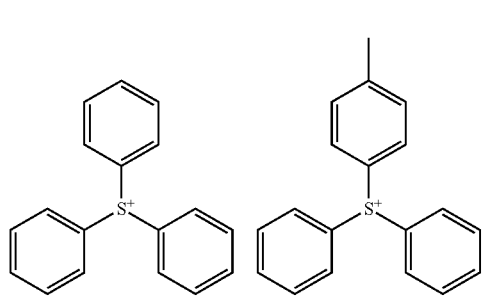
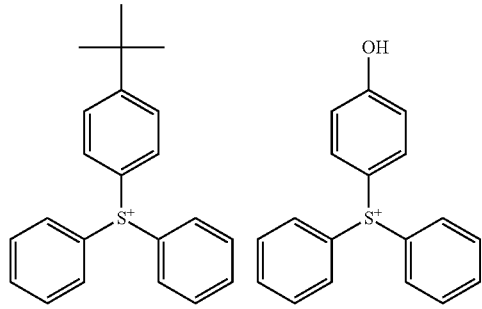
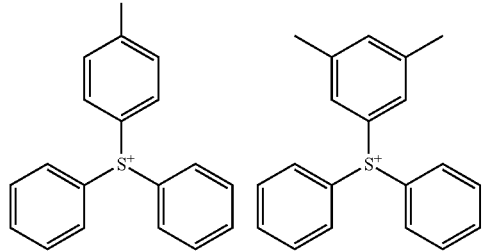
-continued
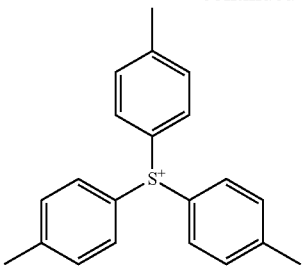
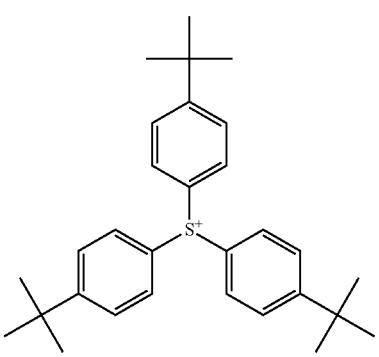
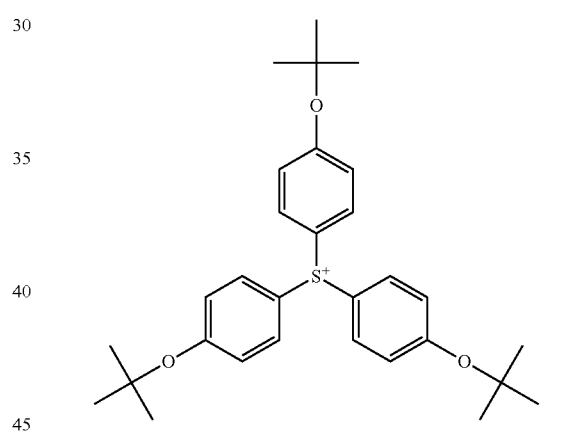

-continued

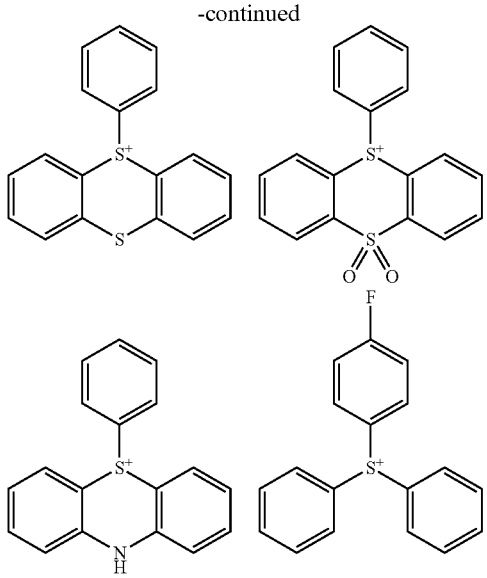

Illustrative structures of the sulfonium salt include arbitrary combinations of the above-exemplified anion moieties with the above-exemplified cation moieties.

In a system where a carboxylic acid onium salt according to the invention and an onium salt capable of generating strong acid such as α-fluorinated sulfonic acid, imidic acid or methidic acid (which are collectively referred to as "strong acid" in this context) are co-present, a corresponding carboxylic acid and strong acid generate upon light exposure. On the other hand, in the region receiving a reduced dose of exposure, much (undecomposed) onium salt is present. The strong acid functions as a catalyst for inducing deprotection reaction to the base resin whereas the carboxylic acid according to the invention induces little deprotection reaction. The strong acid undergoes ion exchange with the residual carboxylic acid sulfonium salt. It is converted to a strong acid onium salt and instead, carboxylic acid is released. Differently stated, through ion exchange, the strong acid is neutralized with the carboxylic acid sulfonium salt. That is, the carboxylic acid sulfonium salt according to the invention functions as a quencher. This onium salt type quencher tends to form a resist pattern with a reduced LWR as compared with the conventional quenchers in the form of amine compounds.

Salt exchange between strong acid and carboxylic acid sulfonium salt is infinitely repeated. The site where strong acid is generated at the end of exposure shifts from the site where the onium salt of strong acid generation type is initially present. It is believed that since the cycle of photo-acid generation and salt exchange is repeated many times, the acid generation point is averaged, which leads to a resist pattern with reduced LWR after development.

As the compound that exerts a quencher effect by a similar mechanism, Patent Documents 1 to 4 report carboxylic acid onium salts, alkylsulfonic acid onium salts, and arylsulfonic acid onium salts. With respect to the type of onium salt, sulfonium, iodonium and ammonium salts are included. However, on use of an alkylsulfonic acid onium salt or arylsulfonic acid onium salt, the generated acid has a certain acid strength so that part thereof may induce deprotection reaction rather than functioning as the quencher, leading to a lowering of resolution and an increase of acid diffusion, which invite losses of resist performance factors like exposure latitude (EL) and mask error factor (MEF). Also, in the case of alkanecarboxylic acid, it can function as the quencher. However, due to its high hydrophilicity, possible leaching of carboxylic acid onium salt in water is a concern, particularly in the ArF immersion lithography. The leaching in water is undesired because it causes contamination to the exposure tool and defect formation after development. As discussed in Patent Document 3, the fluoroalkanecarboxylic acid onium salts offer a certain degree of hydrophilicity control as compared with non-fluorinated acid onium salts, but the control of hydrophilicity is insufficient when the carbon count is low. Although perfluoroalkanecarboxylic acid onium salts having a high carbon count are exemplified, these carboxylic acids have surfactant-like physical properties and are deemed incompatible with resist compositions. Incompatibility with resist composition can cause defect formation. In addition, perfluoroalkanecarboxylic acids are unfavorable from the biotic and environmental aspects.

Also, fluorocarboxylic acid onium salts obtained by simply extending the straight chain allow for acid diffusion and undergo salt exchange with strong acid in the unexposed region, probably leading to losses of resolution, EL and MEF.

When the carboxylic acid sulfonium salt having formula (1) is incorporated in a resist composition, the salt is preferably used in an amount of 0.1 to 40 parts, more preferably 1 to 20 parts by weight per 100 parts by weight of the base resin. Outside the range, a less amount of the salt may fail to achieve the full function whereas a larger amount may invite performance degradations such as a lowering of sensitivity and formation of foreign particles due to short solubility.

The above-discussed problems are solved by the carboxylic acid onium salt of the invention. The carboxylic acid onium salt is structurally characterized in that it is an α,α-difluorocarboxylic acid salt having a cyclic structure. This structure enables to control hydrophilicity to a proper level, minimizes leaching in water particularly in the ArF immersion lithography, and is effective for reducing defects after development. Also due to its bulky structure, acid diffusion is controlled so that a resist composition which is improved not only in LWR, but also in resolution, EL and MEF is available. Furthermore, since the carboxylic acid onium salt of the invention is fully compatible with resist components by virtue of its structure, defects resulting from less-dissolvable onium salts are eliminated or reduced.

The carboxylic acid onium salt of the invention may be synthesized, for example, according to the following Scheme 1.

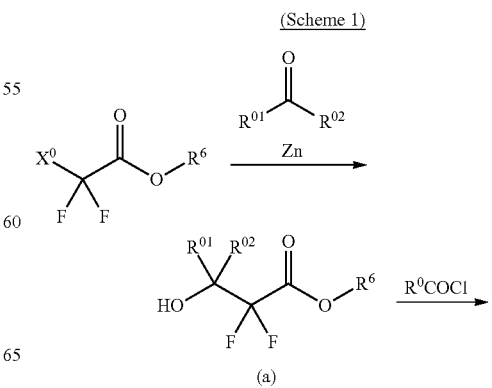

(a)

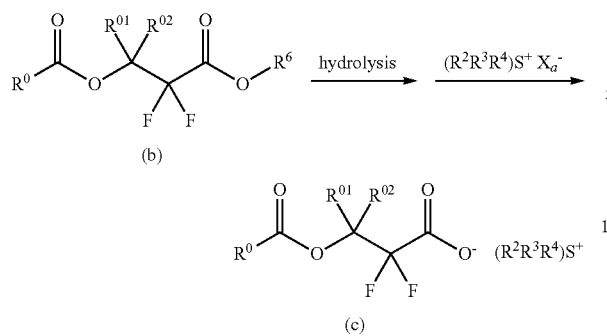

(b)

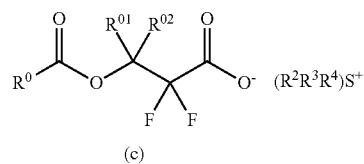

(c)

Herein $X^0$ is a halogen atom, $R^6$ is a straight, branched or cyclic $C_1$-$C_{10}$ monovalent hydrocarbon group, $R^0$, $R^{01}$, $R^{02}$, $R^2$, $R^3$, and $R^4$ are as defined above, and $X_a^-$ is an anion.

In the first step, an α-halodifluoroacetate is reacted with a carbonyl compound in the presence of zinc to synthesize a first intermediate (a). Those compounds wherein $X^0$ is chlorine or bromine and $R^6$ is methyl or ethyl are commercially available. The first intermediate (a) is reacted with an acid chloride for acylation to synthesize a second intermediate (b). For the acylation reaction, not only the reaction with acid chloride, but also any well-known organic chemistry reactions such as reaction with acid anhydride are applicable. Next, the second intermediate (b) is hydrolyzed in a standard manner to eliminate $R^6$. The resulting carboxylic acid salt or carboxylic acid is then reacted with a sulfonium salt of the formula: $(R^2R^3R^4)S^+X_a^-$, to synthesize the desired compound, carboxylic acid sulfonium salt (c). Of the anions represented by $X_a^-$, chloride, bromide, iodide, and methylsulfate anions are preferred because they allow for quantitative progress of exchange reaction.

The final step of ion exchange in Scheme 1 may be readily carried out by well-known methods, for example, with reference to JP-A 2007-145797 (U.S. Pat. No. 7,511,169).

Alternatively, the carboxylic acid onium salt of the invention may be synthesized according to the following Scheme 2.

(Scheme 2)

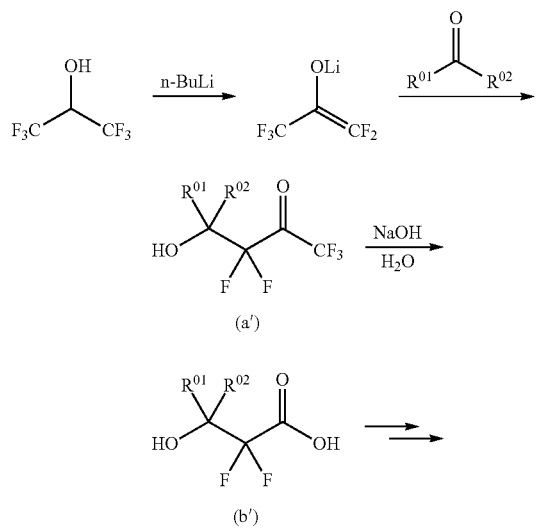

Herein $R^0$, $R^{01}$, $R^{02}$, $R^2$, $R^3$, and $R^4$ are as defined above.

In the first step, 1,1,1,3,3,3-hexafluoro-2-isopropanol is reacted with n-butyl lithium to form a fluoroenolate, which is, in turn, reacted with a carbonyl compound to synthesize a first intermediate (a'). Subsequently, the first intermediate (a') is subjected to haloform reaction in the presence of sodium hydroxide, to form a second intermediate (b'). After the corresponding carboxyl group is protected if necessary, this is followed by acylation of hydroxyl and salt exchange reaction by the same procedures as in Scheme 1, for thereby synthesizing the desired compound, carboxylic acid sulfonium salt (c). For the series of reactions according to Scheme 2, reference may be made to JP-A 2012-097256 (U.S. Pat. No. 8,697,903), for example.

Understandably, the synthesis methods according to Schemes 1 and 2 illustrated above are merely exemplary and the invention is not limited thereto. While Schemes 1 and 2 refer to the synthesis of ester compounds, those skilled artisans can synthesize sulfonium salts having an ether bond, sulfonate bond, carbonate bond or carbamate bond by using the chemical techniques within the common knowledge of organic chemistry.

Resist Composition

Another embodiment of the invention is directed to a resist composition comprising (A) the carboxylic acid sulfonium salt of formula (1) as an essential component, (B) a polymer as a base resin, and (E) an organic solvent. If necessary, the resist composition may further comprise (C) a photoacid generator having the general formula (4) to be defined below and (D) a nitrogen-containing compound. Optionally, the resist composition may further comprise (F) a surfactant which is insoluble or substantially insoluble in water and soluble in alkaline developer, and/or a surfactant which is insoluble or substantially insoluble in water and alkaline developer (hydrophobic resin), and (G) an organic acid derivative and/or fluorinated alcohol.

(B) Base Resin

The base resin used in the resist composition is preferably a polymer comprising recurring units having the general formula (2) and recurring units having the general formula (3).

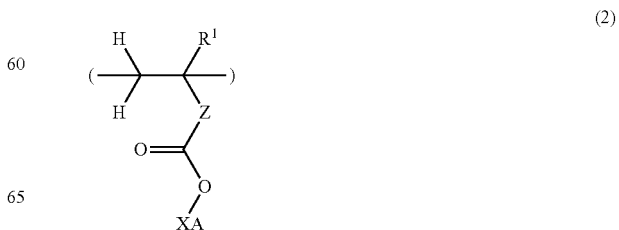

(2)

-continued

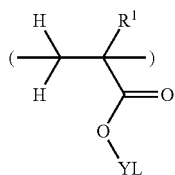

(3)

Herein R¹ is hydrogen, fluorine, methyl or trifluoromethyl. Z is a single bond, phenylene, naphthylene or (backbone)-C(=O)-O-Z'-, wherein Z' is a straight $C_1$-$C_{10}$ or branched or cyclic $C_3$-$C_{10}$ alkylene group which may contain a hydroxyl radical, ether bond, ester bond, or lactone ring, or a phenylene or naphthylene group. XA is an acid labile group. YL is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

Examples of the structure of formula (2) wherein Z is a variant are illustrated below.

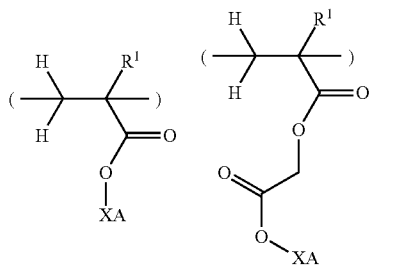

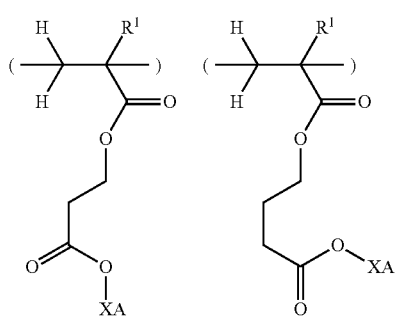

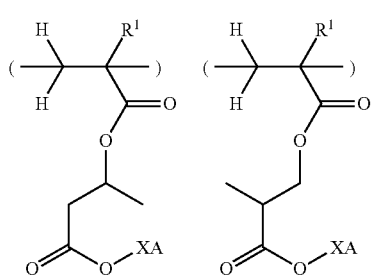

-continued

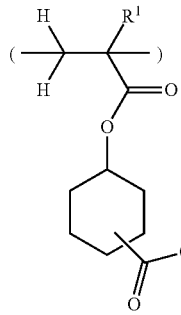 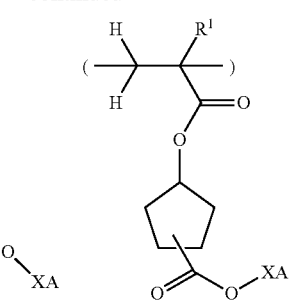

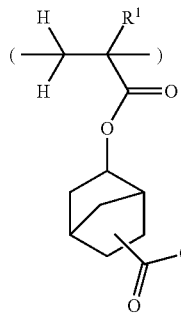 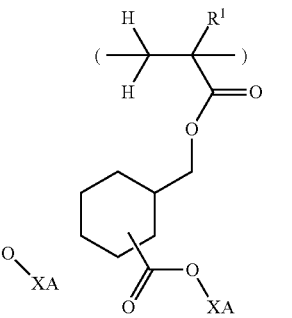

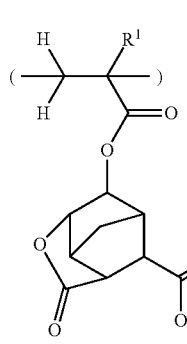 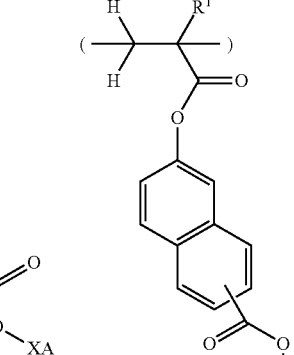

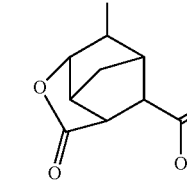 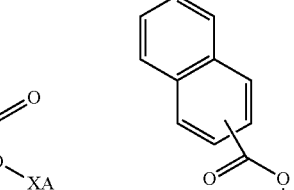

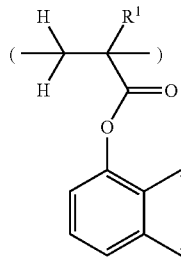 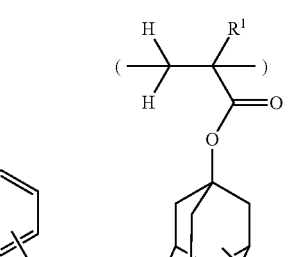

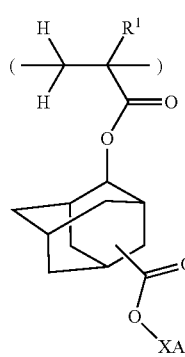 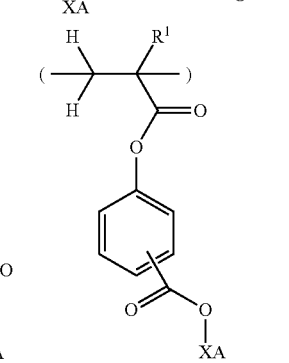

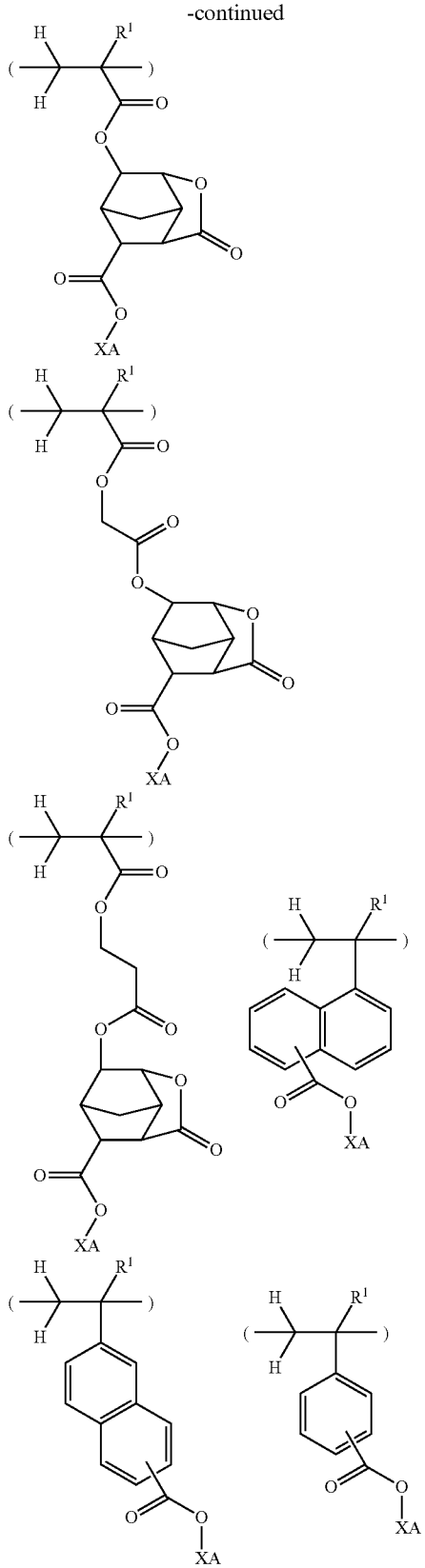

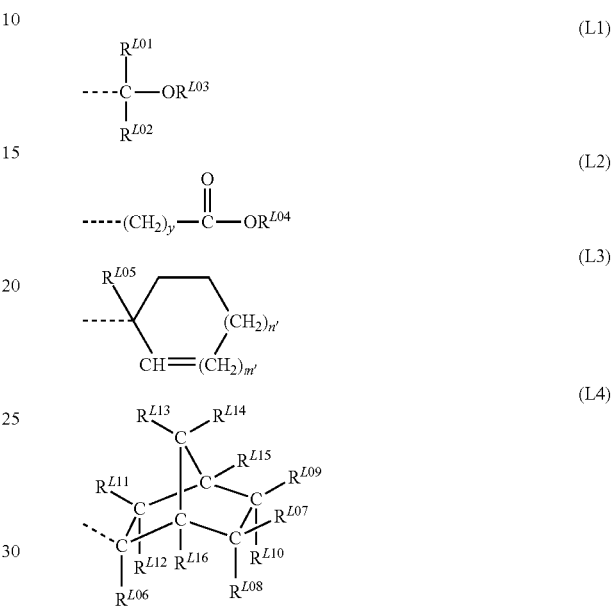

soluble. The acid labile group represented by XA may be selected from a variety of such groups. Examples of the acid labile group include groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

It is noted that the broken line denotes a valence bond.

In formula (L1), $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like, or in which an oxygen atom intervenes between carbon atoms. Exemplary straight, branched or cyclic alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. Illustrative examples of the substituted alkyl groups are shown below.

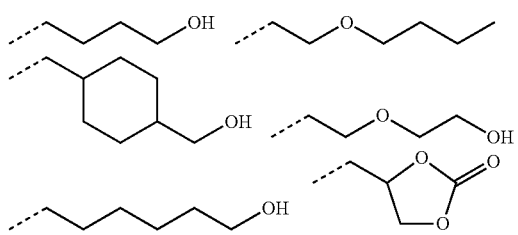

The polymer comprising recurring units having formula (2) functions such that it may be decomposed to generate carboxylic acid under the action of an acid and turn alkali A pair of $R^{L01}$ and $R^{L02}$, $R^{L01}$ and $R^{L03}$, or $R^{L02}$ and $R^{L03}$ may bond together to form a ring with the carbon and oxygen atom to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl.

Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is an optionally substituted, straight, branched or cyclic $C_1$-$C_8$ alkyl group or an optionally substituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl and cyclohexyl, and substituted forms of the foregoing in which some hydrogen atoms are substituted by hydroxyl, alkoxy, carboxyl, alkoxycarbonyl, oxo, amino, alkylamino, cyano, mercapto, alkylthio, sulfo or the like. Examples of the optionally substituted aryl groups include phenyl, methylphenyl, naphthyl, anthryl, phenanthryl, and pyrenyl. Letter m' is equal to 0 or 1, n' is equal to 0, 1, 2 or 3, and 2m'+n' is equal to 2 or 3.

In formula (L4), $R^{L06}$ is an optionally substituted, straight, branched or cyclic $C_1$-$C_8$ alkyl group or an optionally substituted $C_6$-$C_{20}$ aryl group. Examples of these groups are the same as exemplified for $R^{L05}$. $R^{L07}$ to $R^{L16}$ independently represent hydrogen or $C_1$-$C_{15}$ monovalent hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, $R^{L14}$ and $R^{L15}$, or a similar pair).

Of the acid labile groups of formula (L1), the straight and branched ones are exemplified by the following groups.

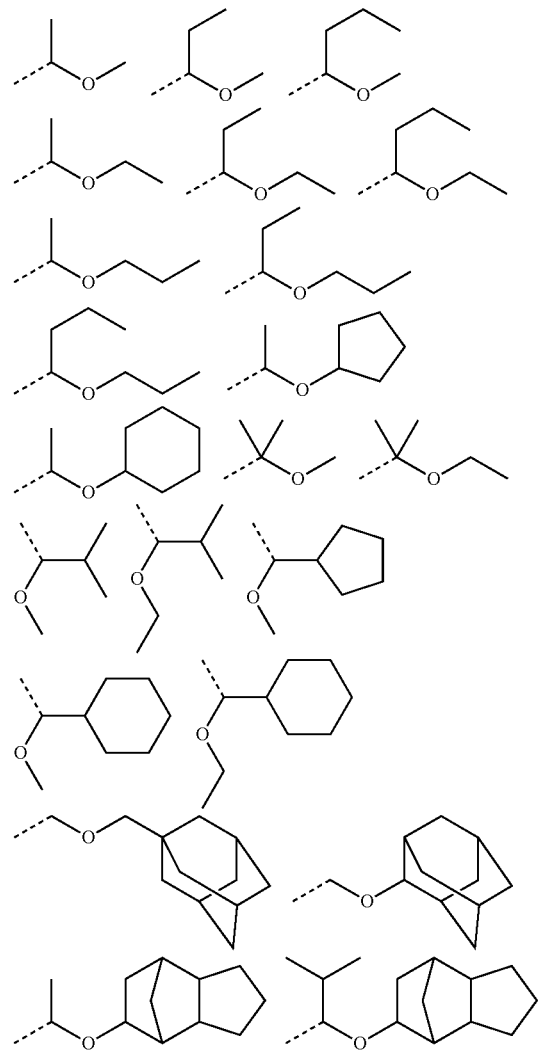

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

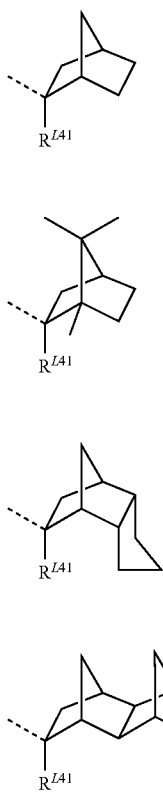

(L4-1)

(L4-2)

(L4-3)

(L4-4)

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

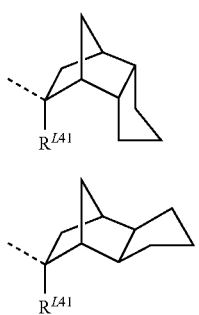

(L4-3-1)

(L4-3-2)

Similarly, the general formula (L4-4) represents one or a mixture of two or more selected from groups having the following general formulas (L4-4-1) to (L4-4-4).

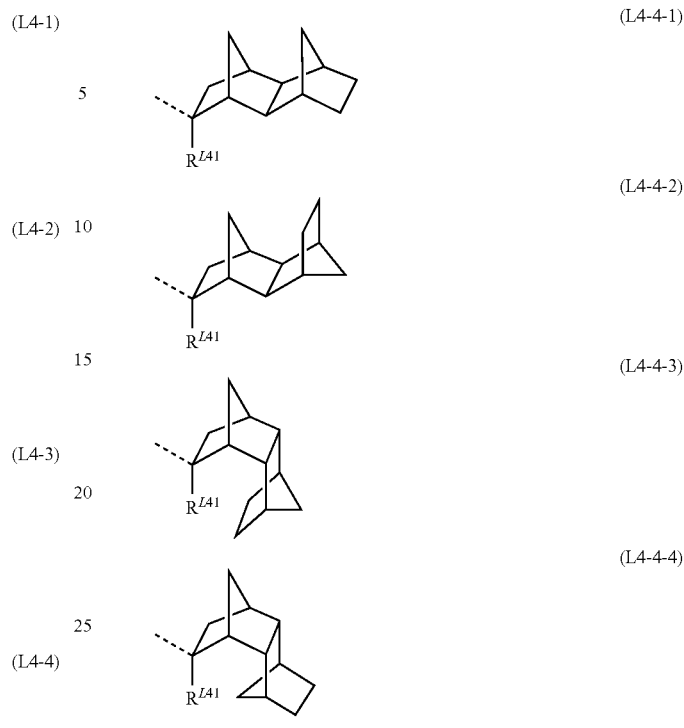

(L4-4-1)

(L4-4-2)

(L4-4-3)

(L4-4-4)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

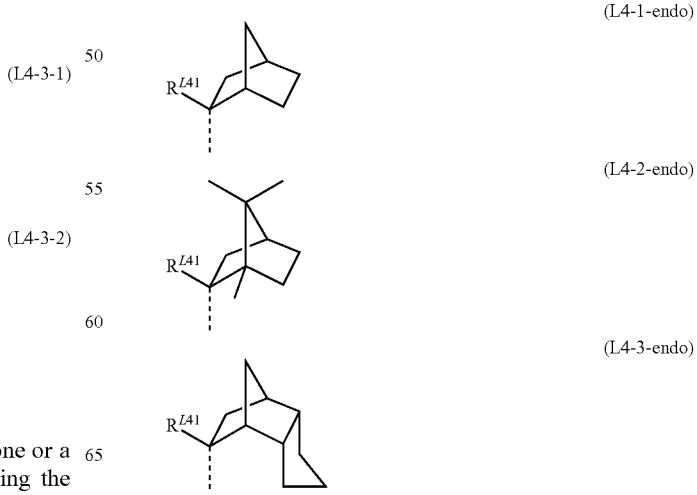

(L4-1-endo)

(L4-2-endo)

(L4-3-endo)

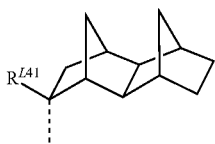
(L4-4-endo)
Illustrative examples of the acid labile group of formula (L4) are given below.
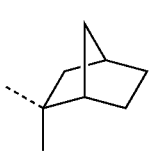 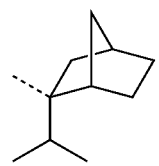
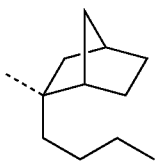 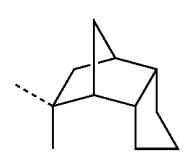
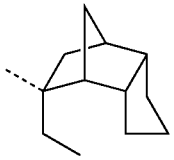 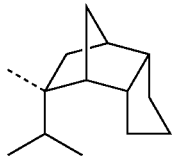
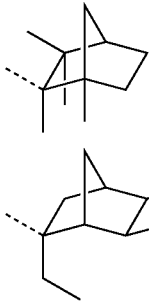 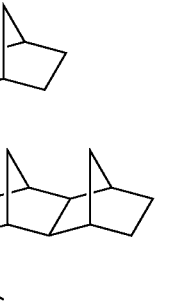
Examples of the tertiary $C_4$-$C_{20}$ alkyl groups, trialkylsilyl groups in which each alkyl moiety has 1 to 6 carbon atoms, and $C_4$-$C_{20}$ oxoalkyl groups are as exemplified for $R^{L04}$.
Illustrative examples of the recurring units of formula (2) are given below, but not limited thereto.
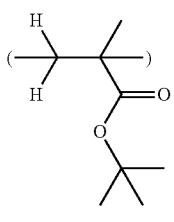 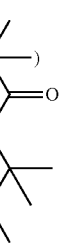
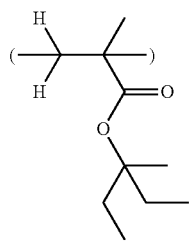 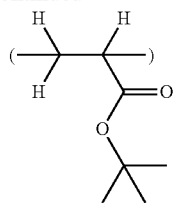
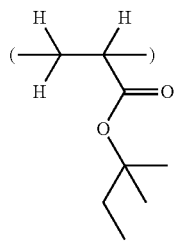 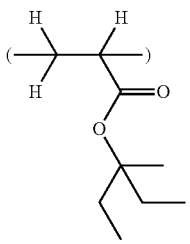
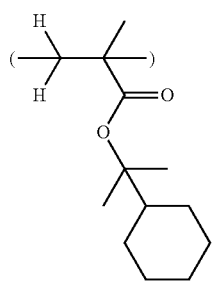 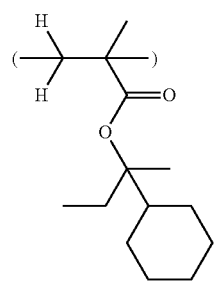
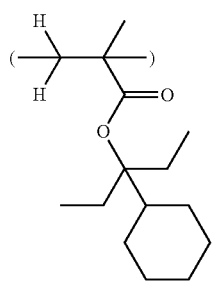 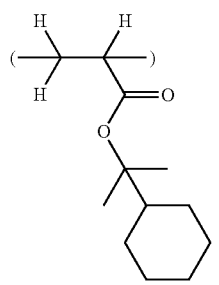
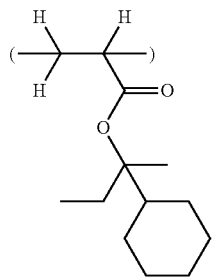 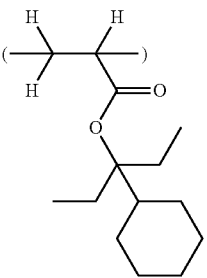
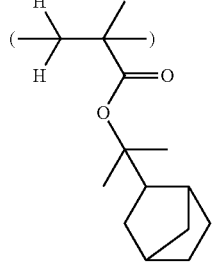 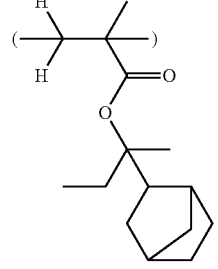

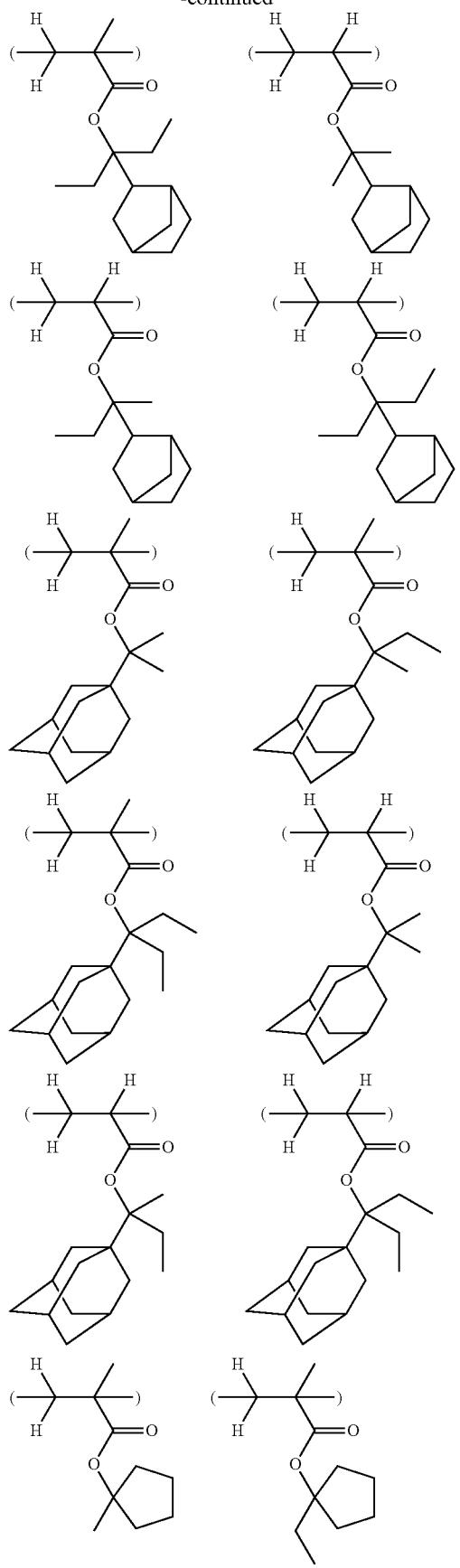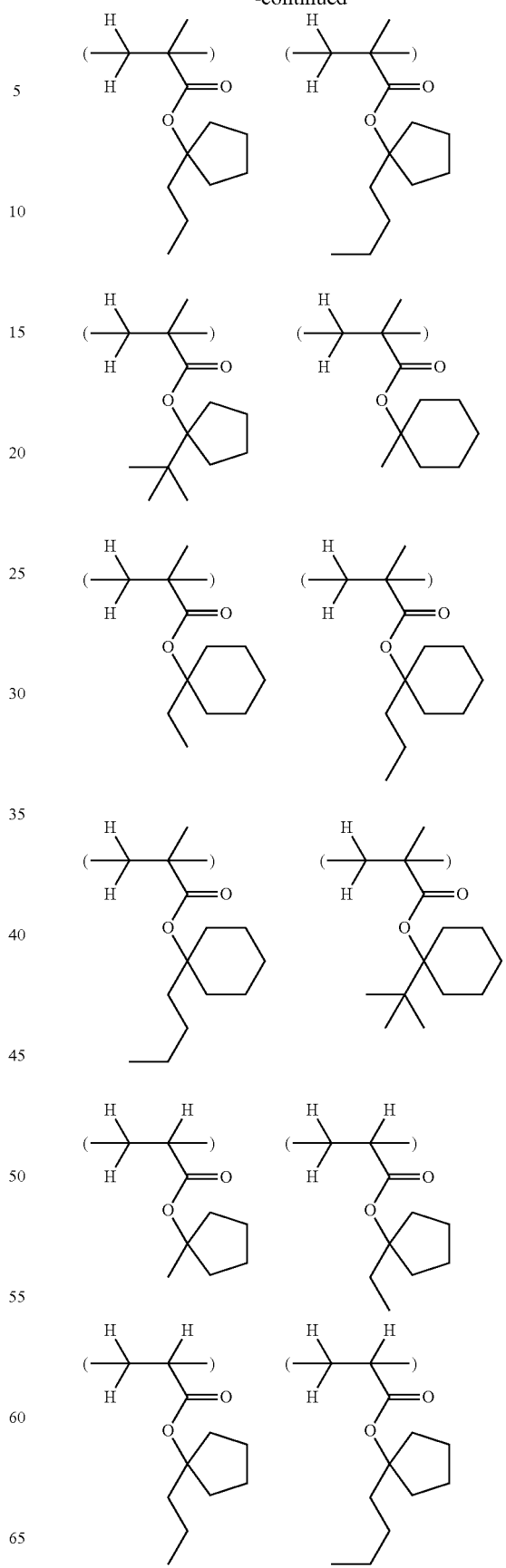

-continued

-continued
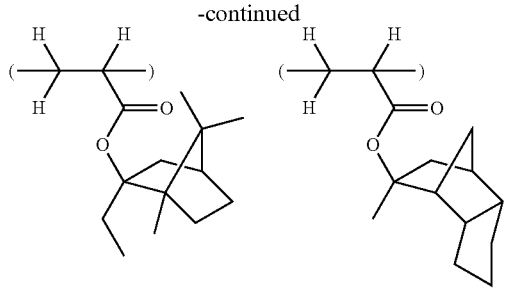
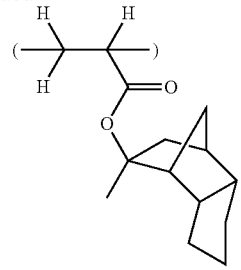
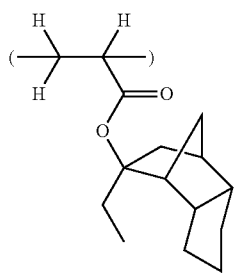
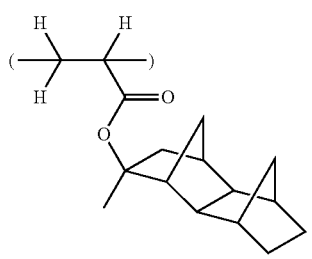
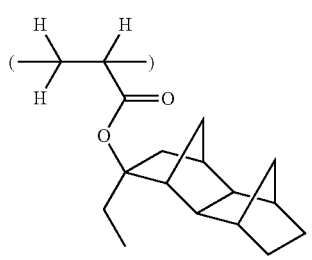
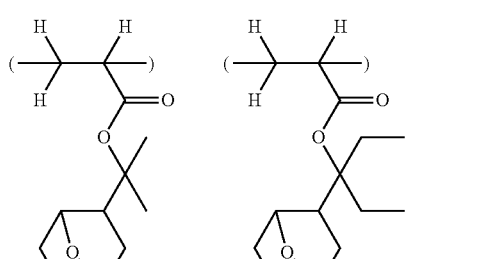
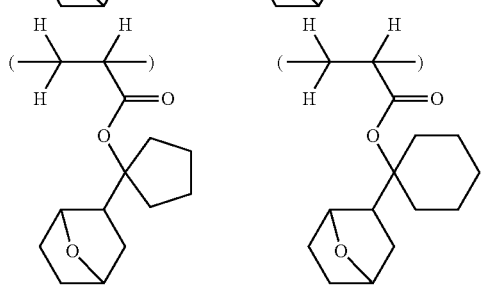
-continued
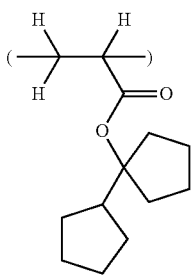
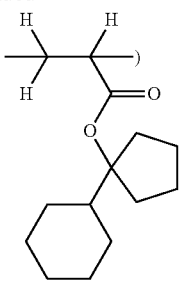
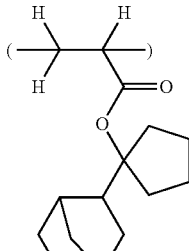
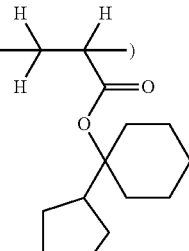
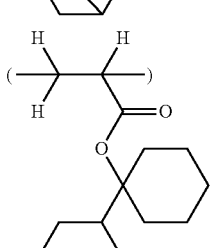
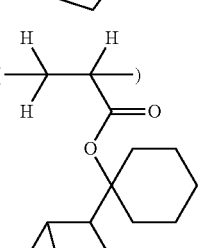
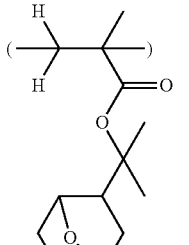
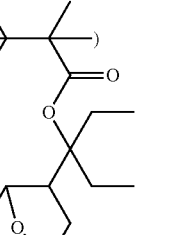
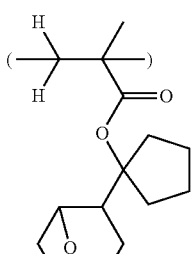
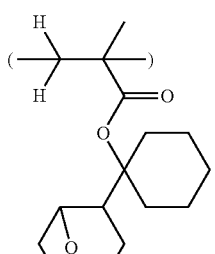
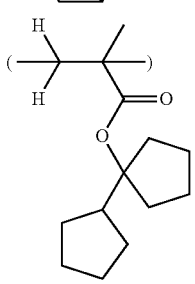
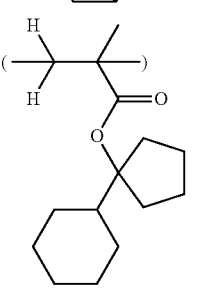

-continued
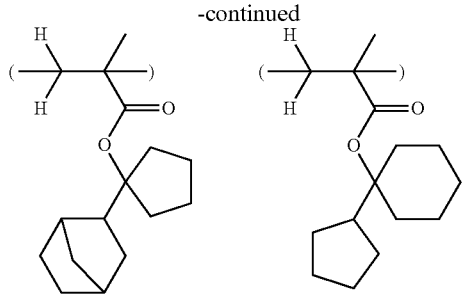
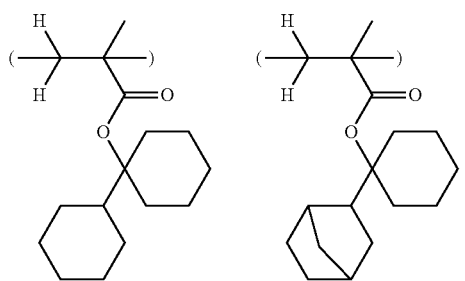
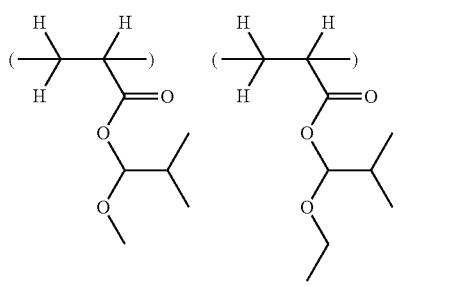
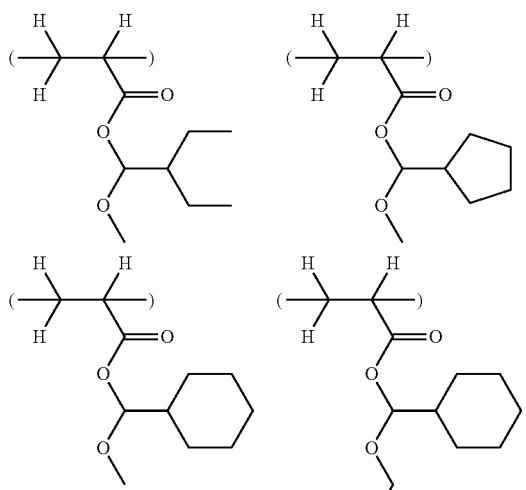
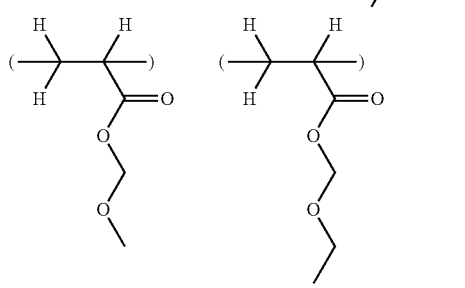
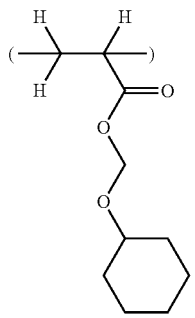
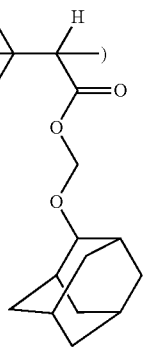
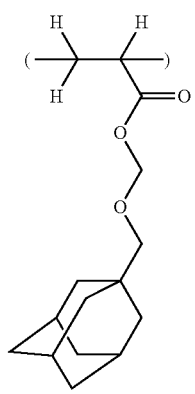
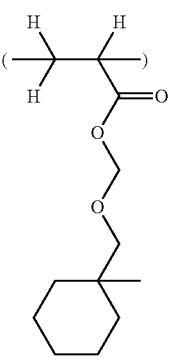
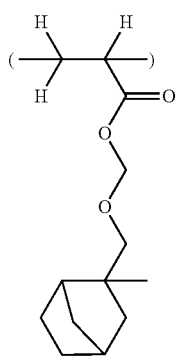
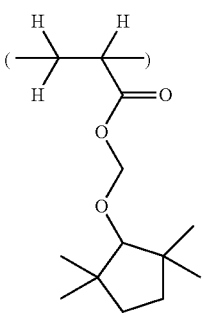
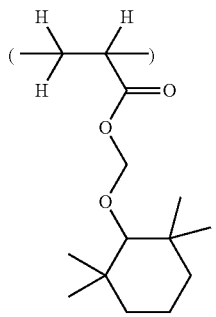
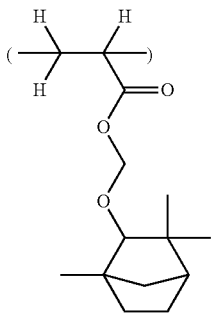

-continued
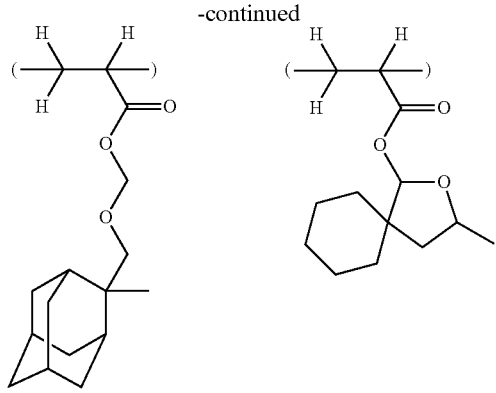
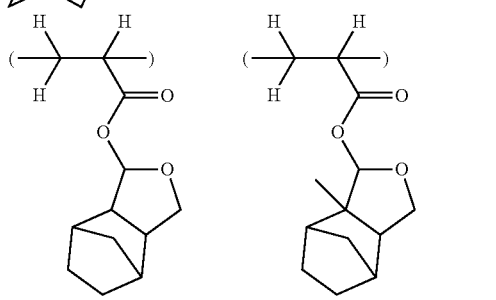
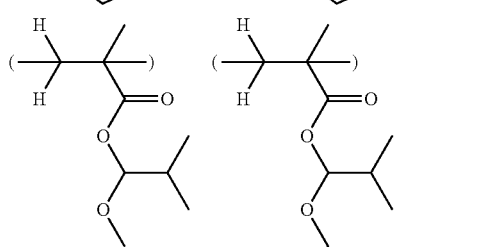
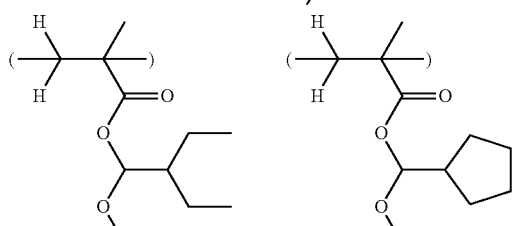
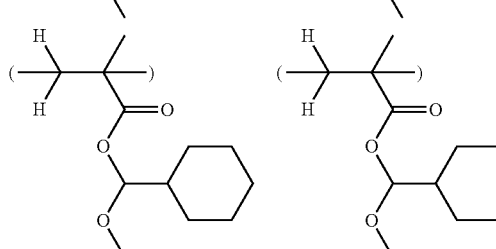
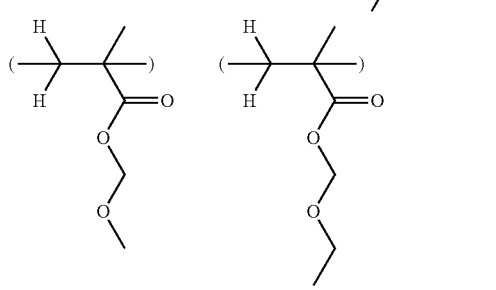
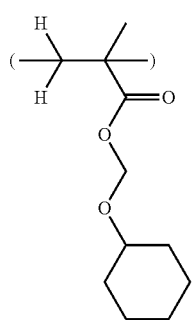
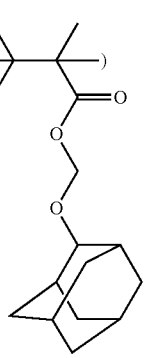
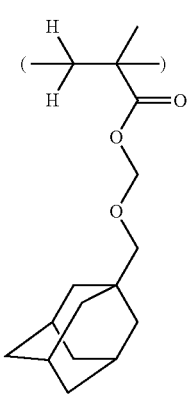
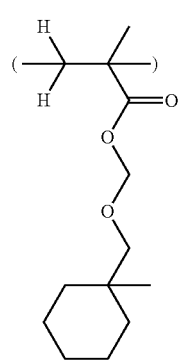
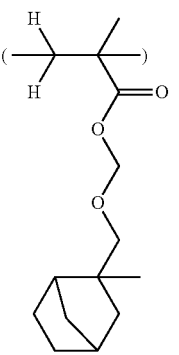
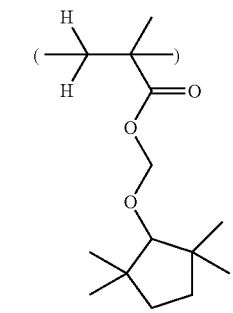
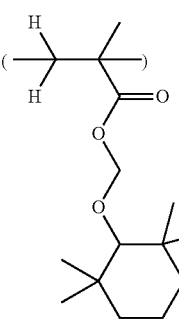
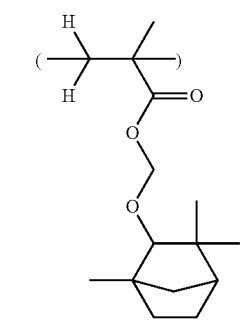

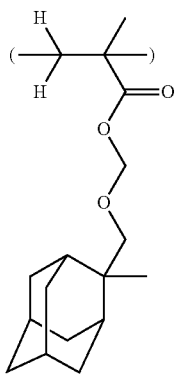
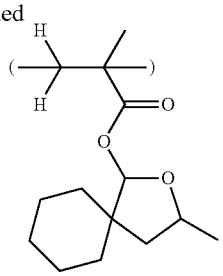
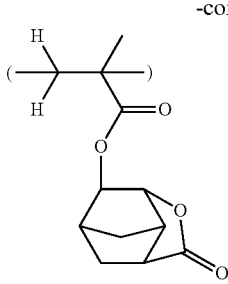
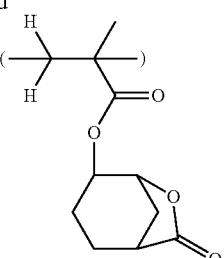

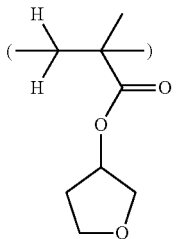
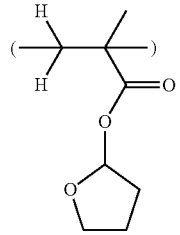

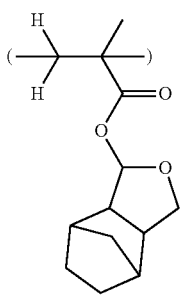
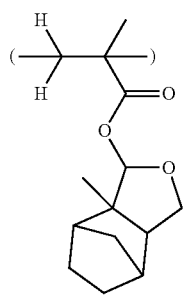

The above examples correspond to those units of formula (2) wherein Z is a single bond. Where Z is other than a single bond, a combination with a similar acid labile group is possible. Thus examples of the recurring units of formula (2) wherein Z is other than a single bond are as illustrated above.

In formula (3), YL is hydrogen, or YL is a polar group having one or more structures selected from the group consisting of hydroxyl, cyano, carbonyl, carboxyl, ether bond, ester bond, sulfonate (sulfonic acid ester) bond, carbonate bond, lactone ring, sultone ring, and carboxylic anhydride.

Illustrative examples of the recurring units of formula (3) are given below, but not limited thereto.

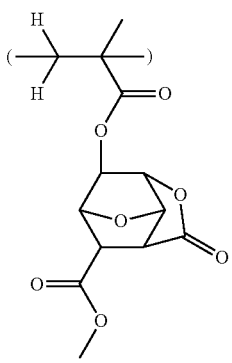
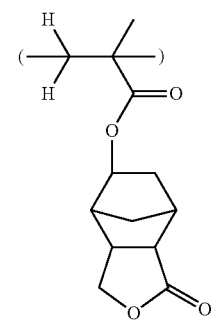

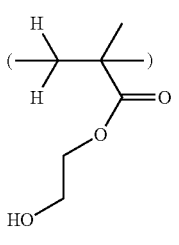
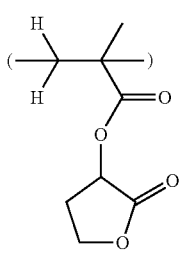

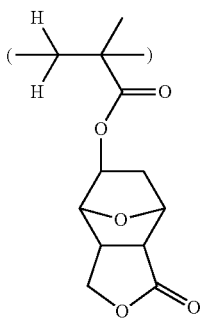
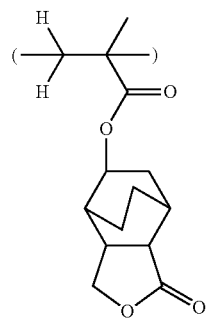

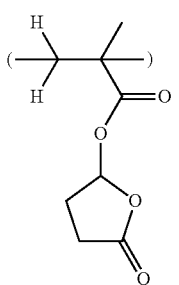
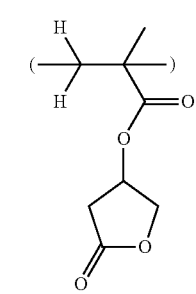
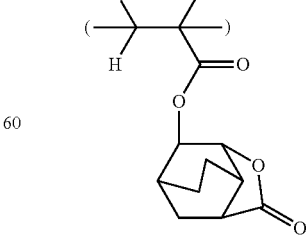
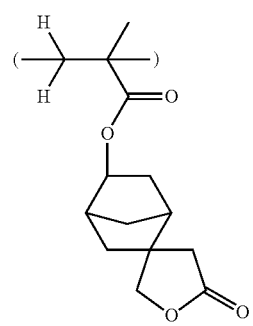

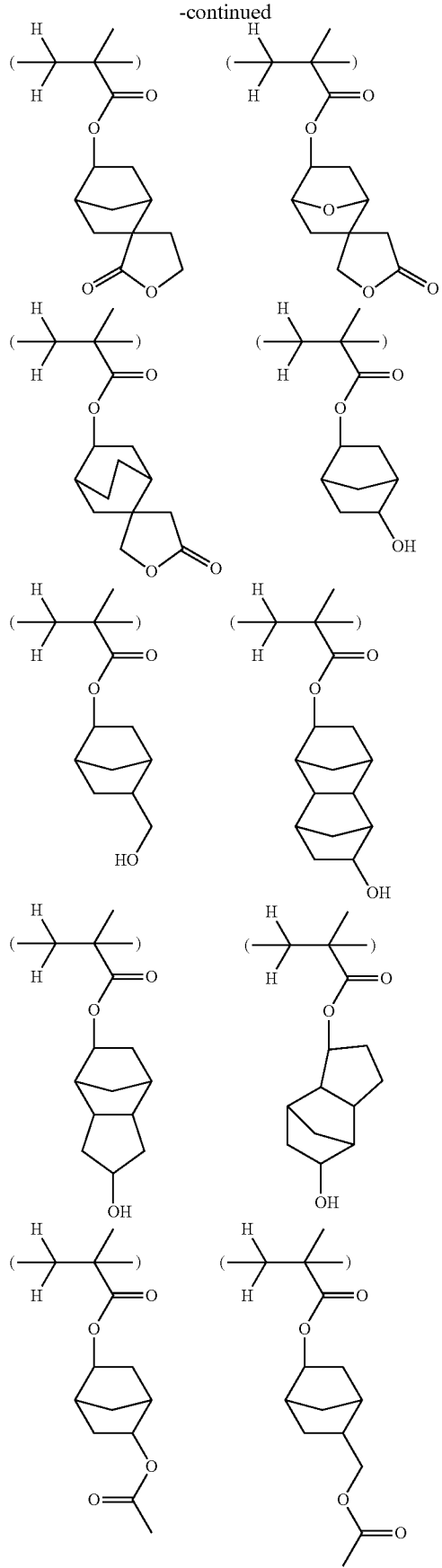
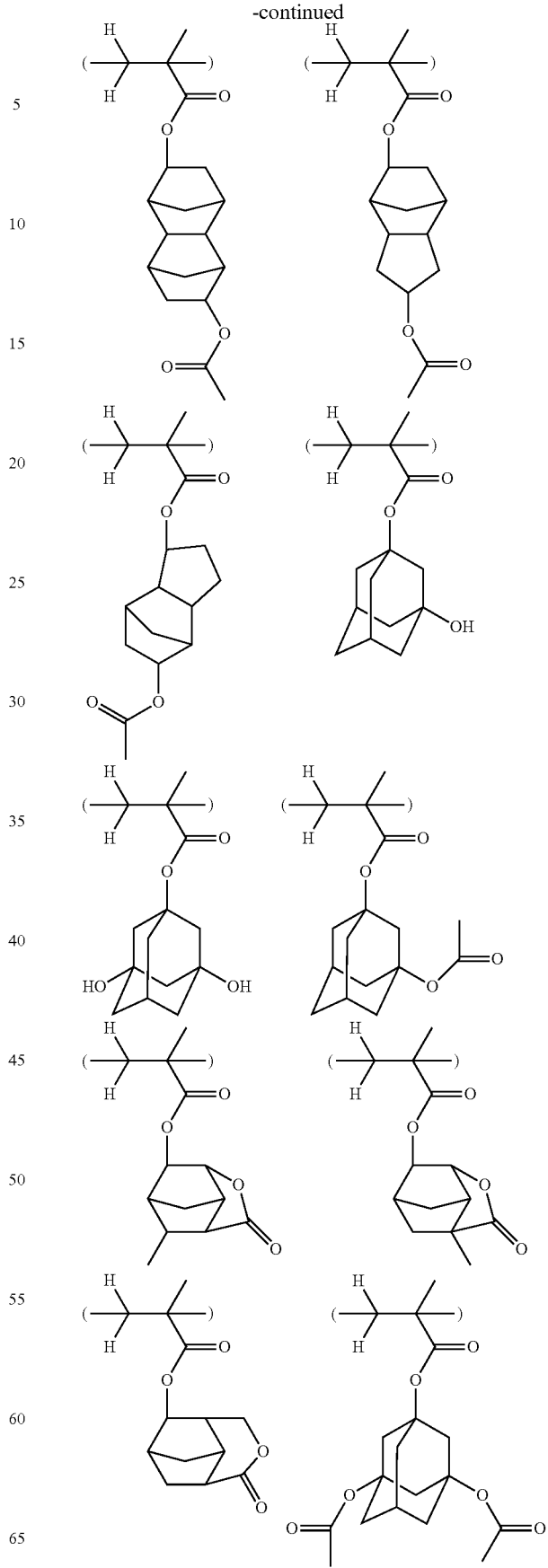

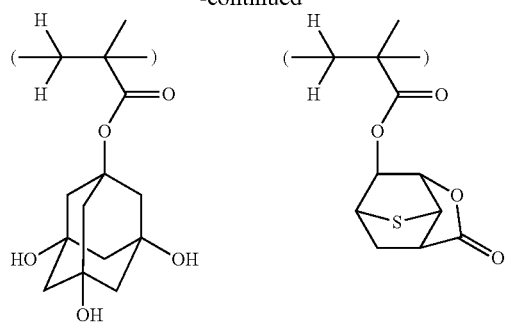
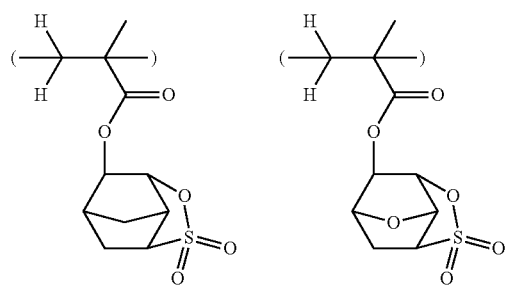
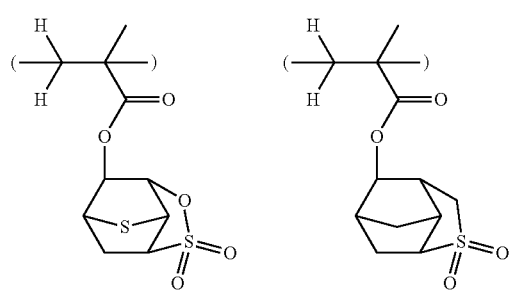
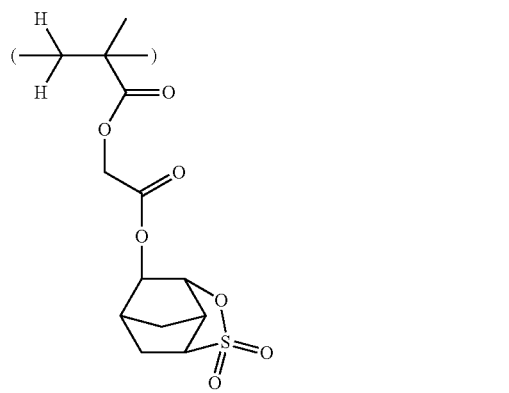
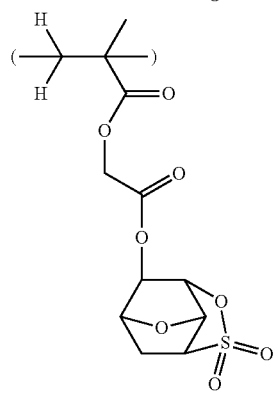
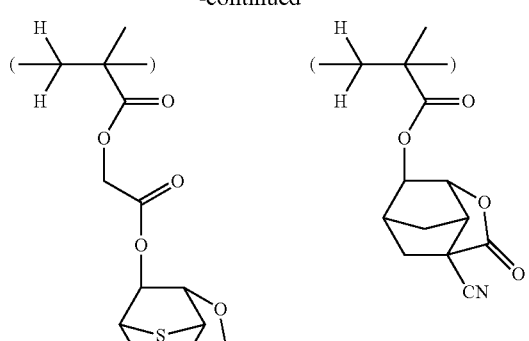
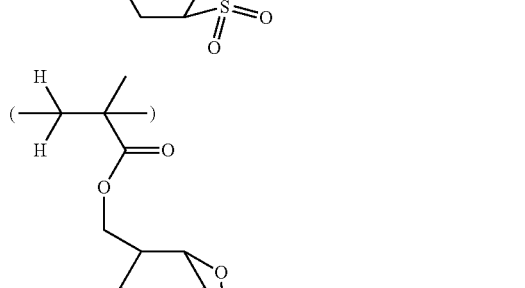
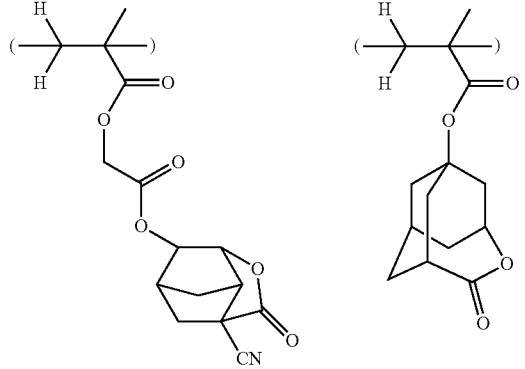
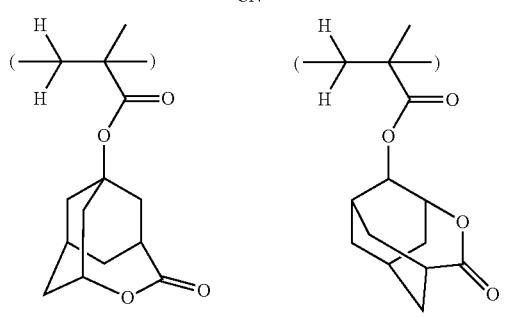
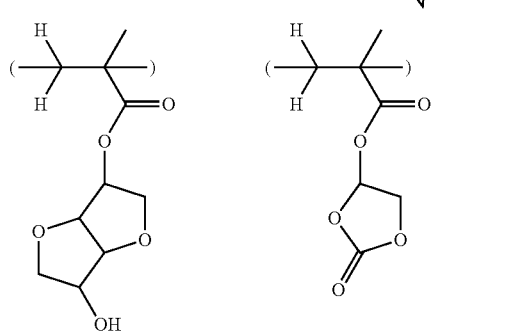

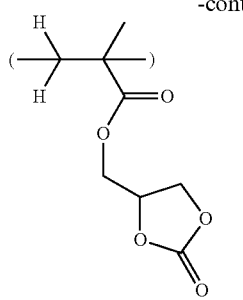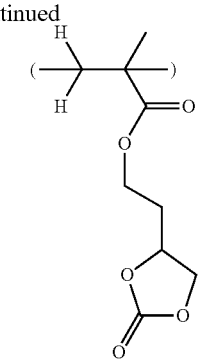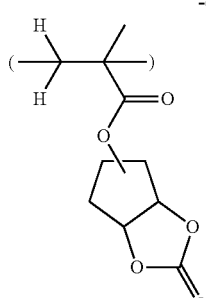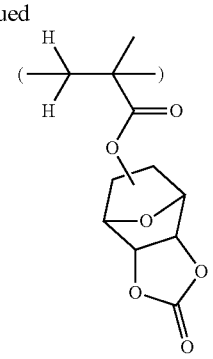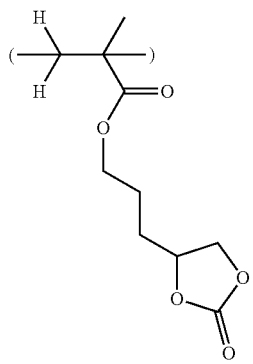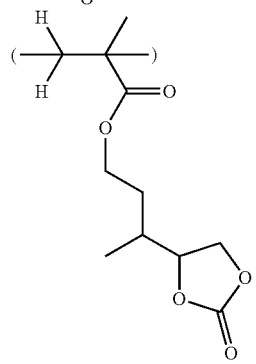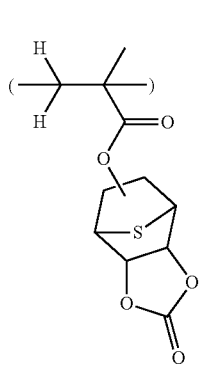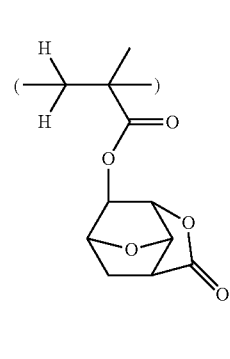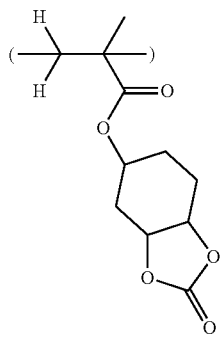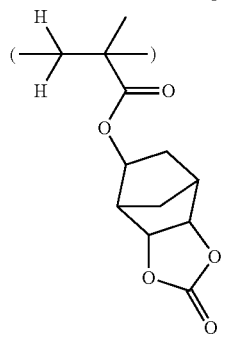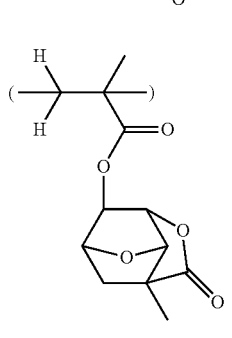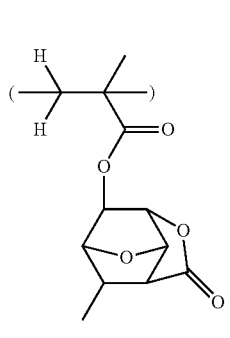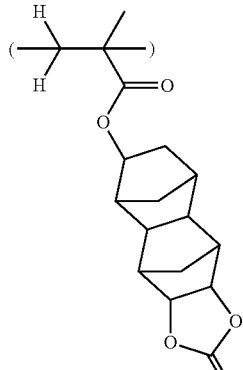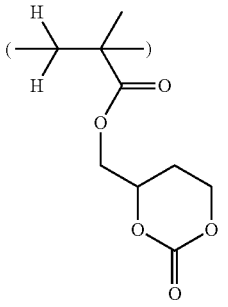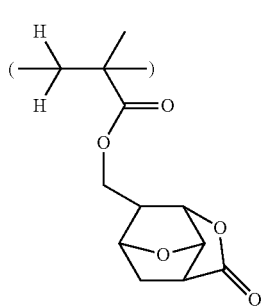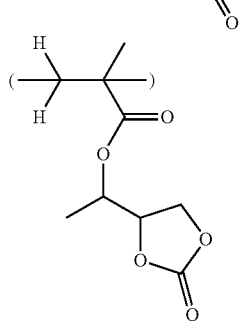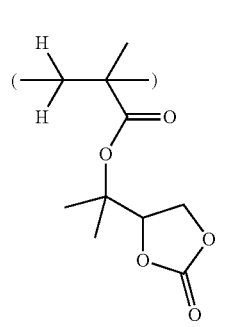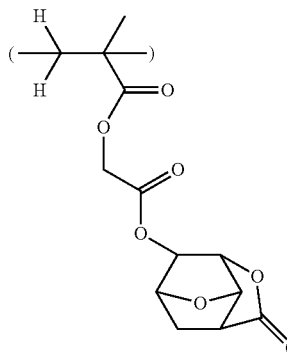

-continued
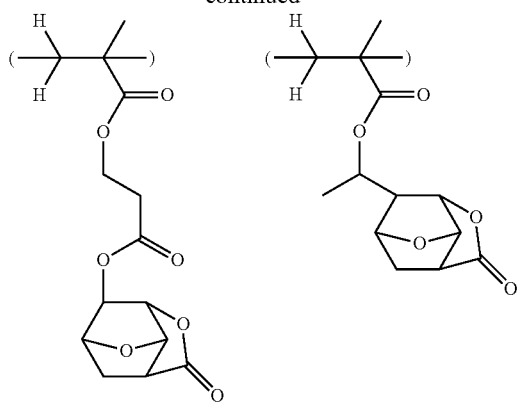
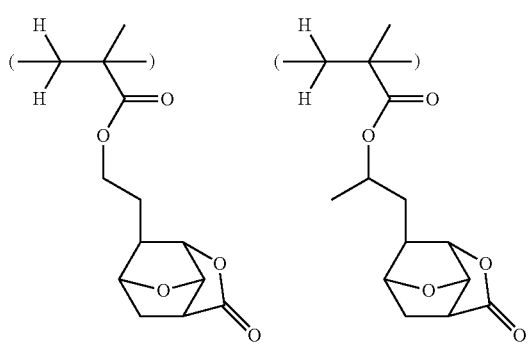
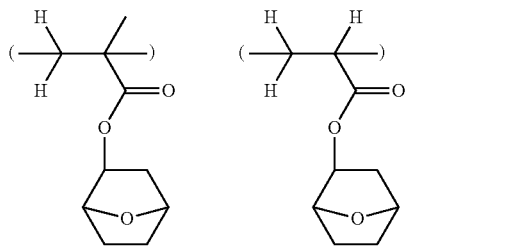
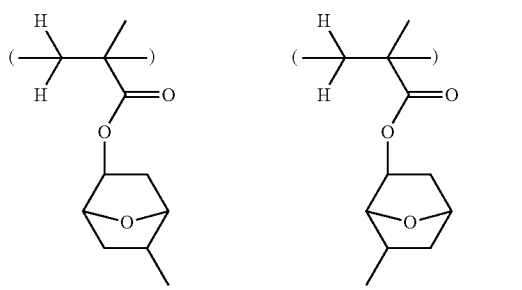
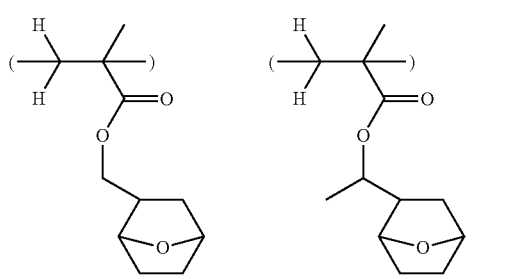
-continued
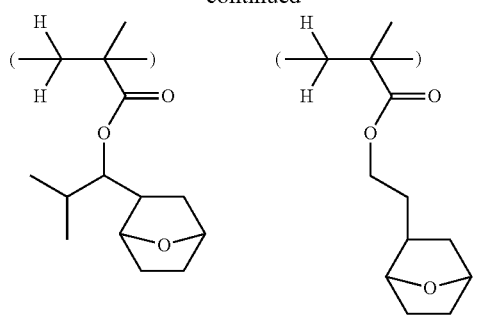
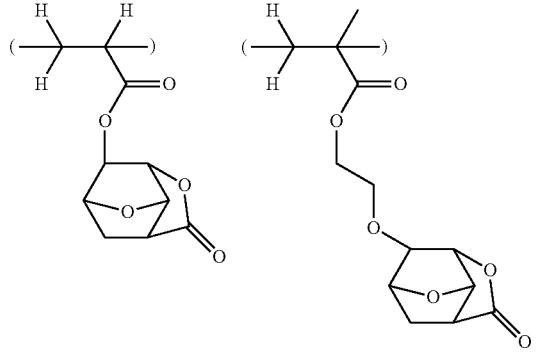
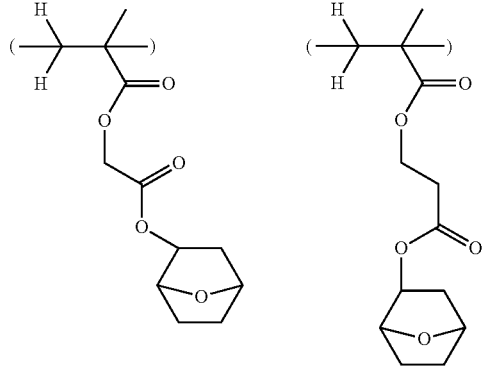
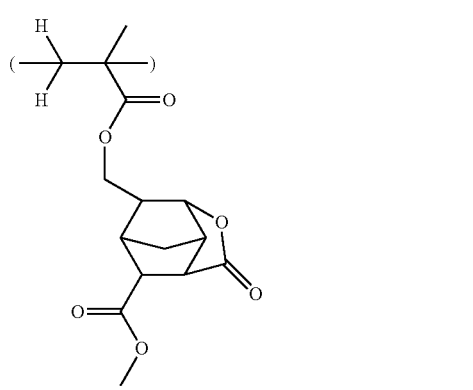

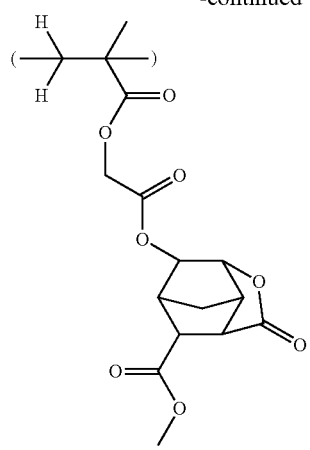
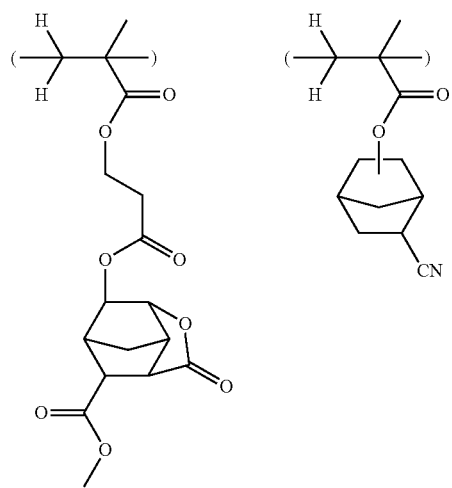
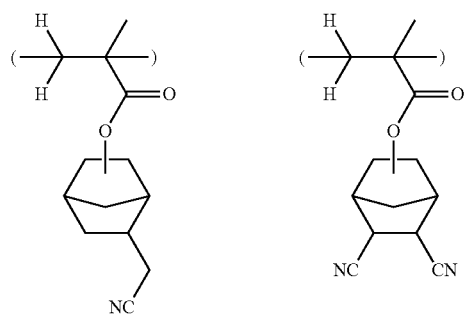
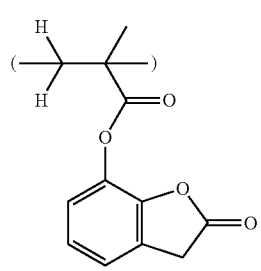
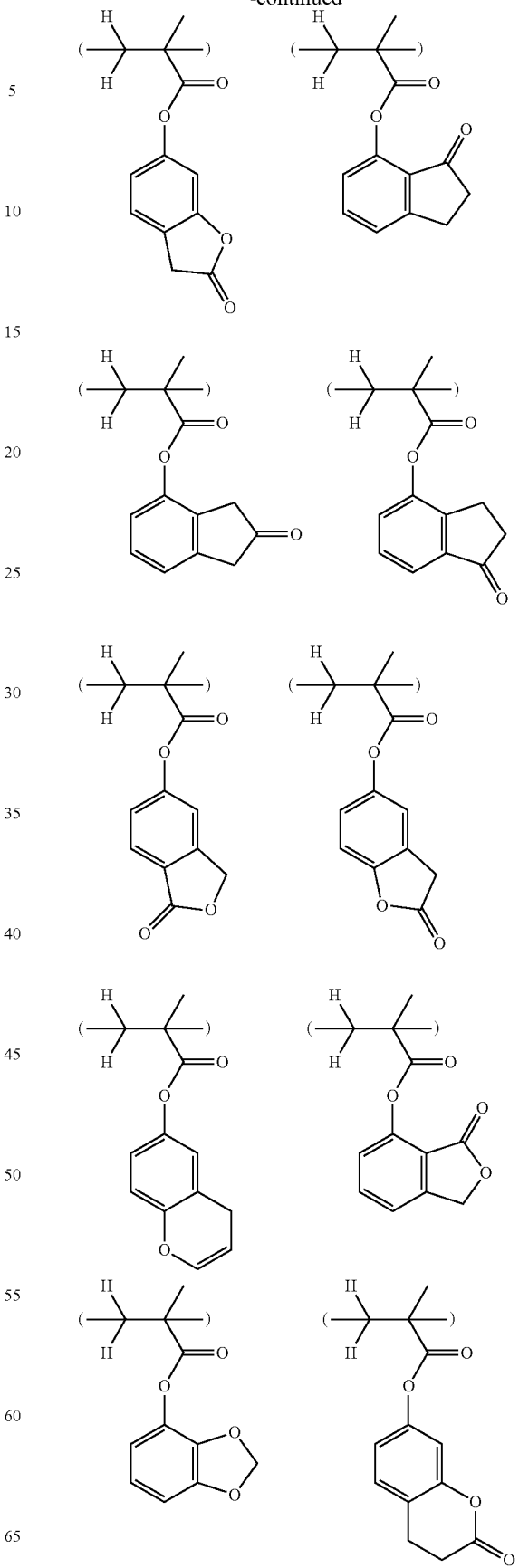

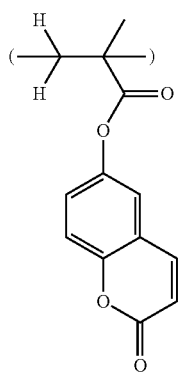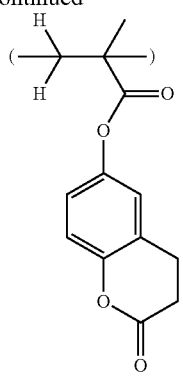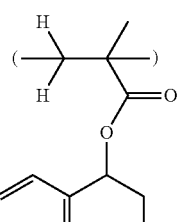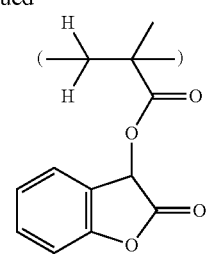
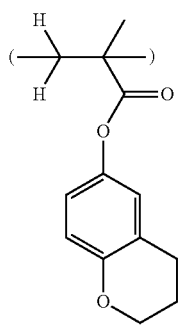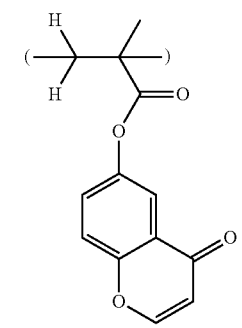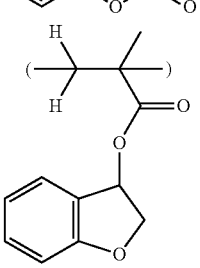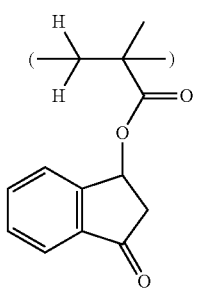
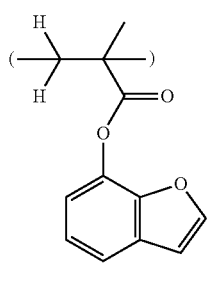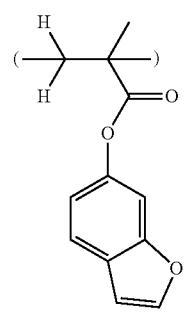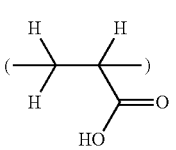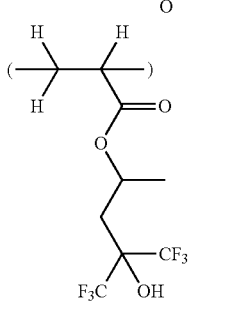
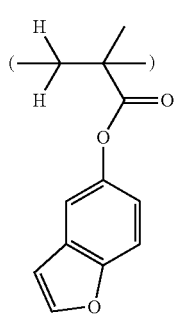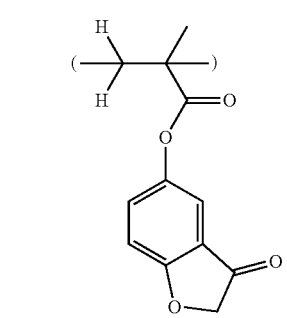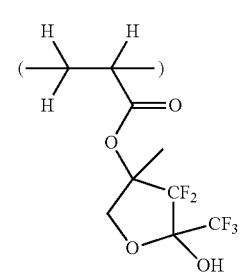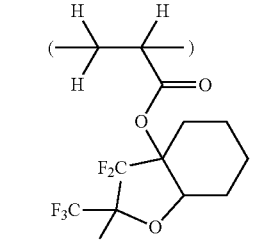
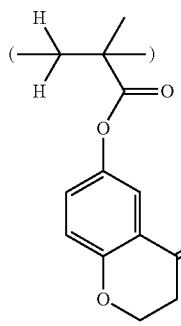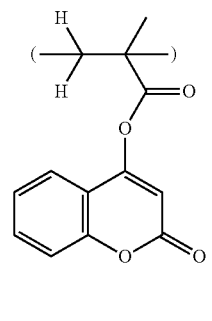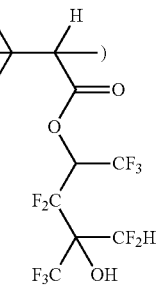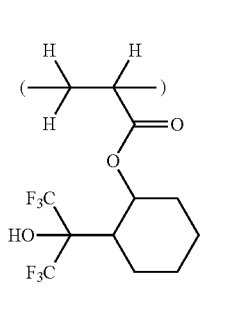

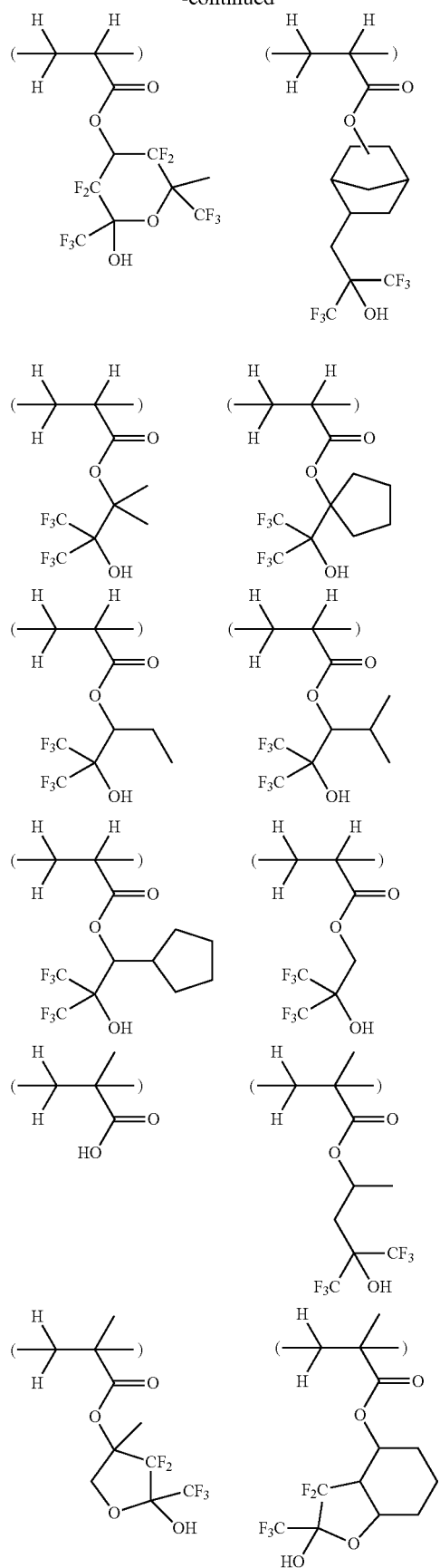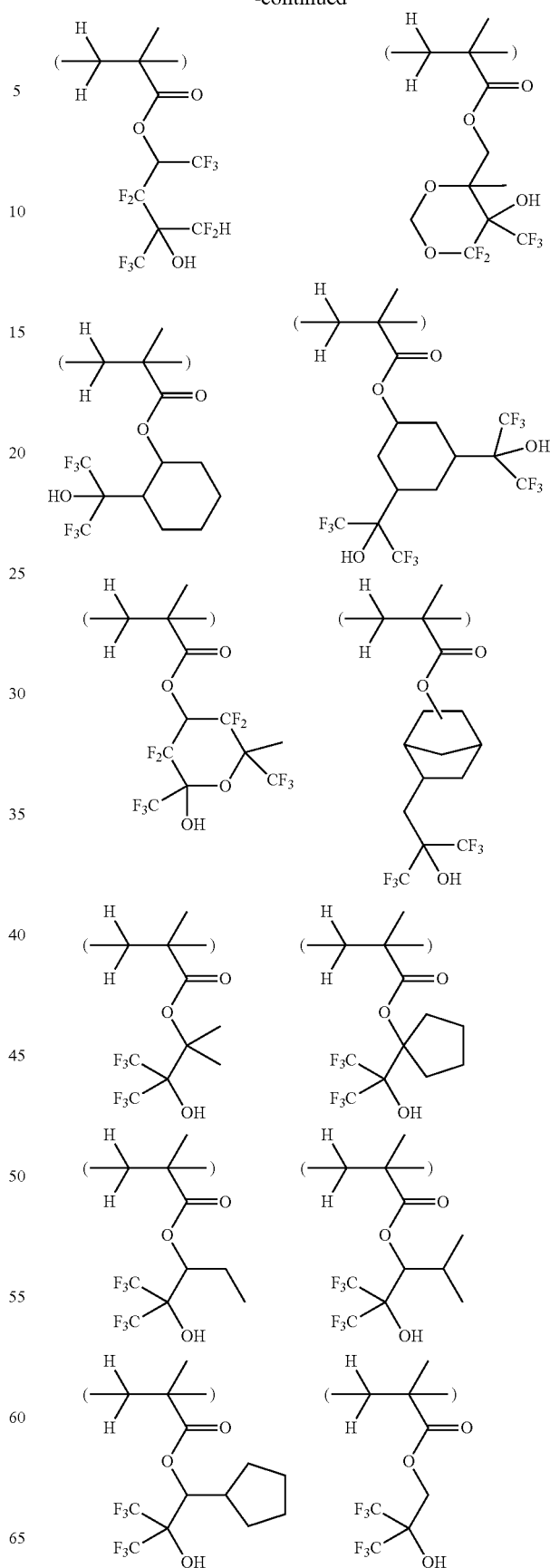

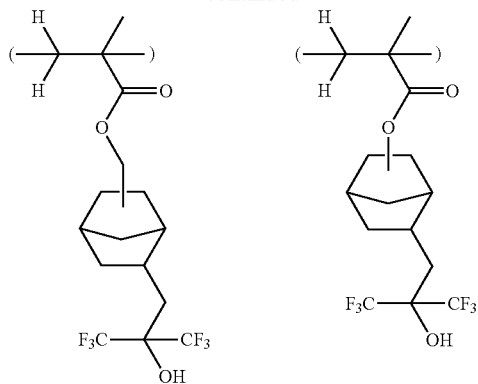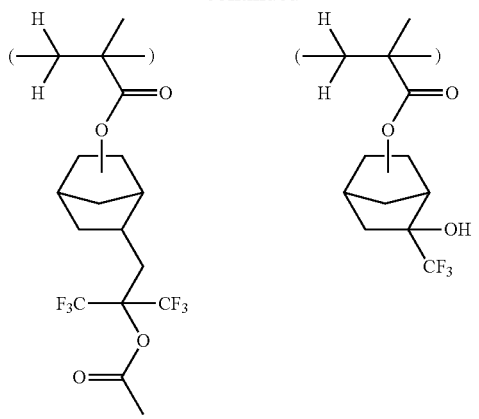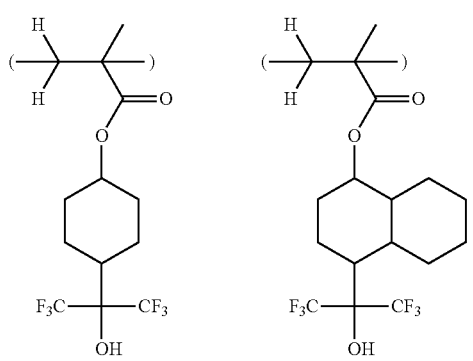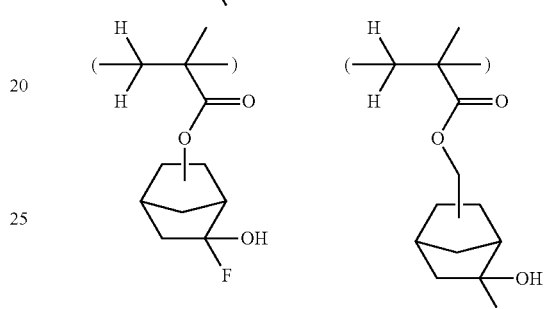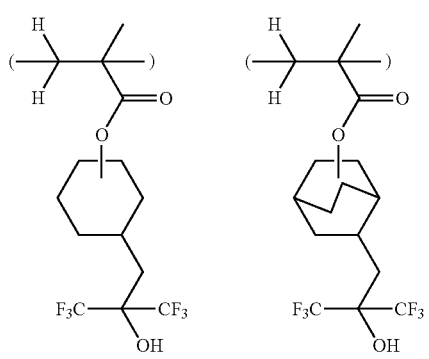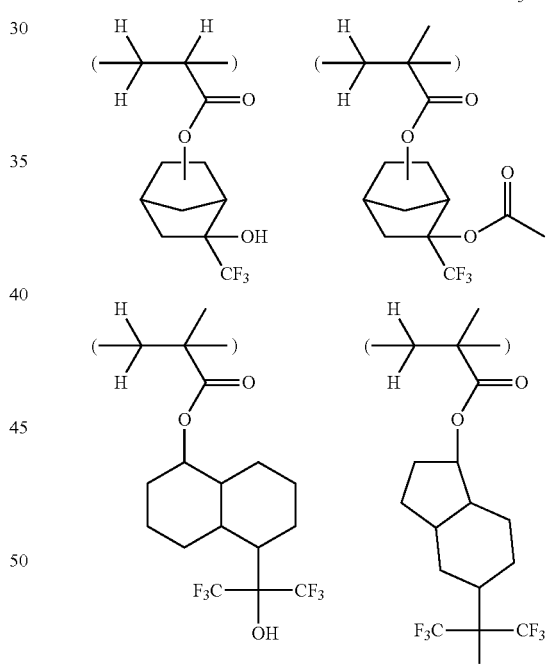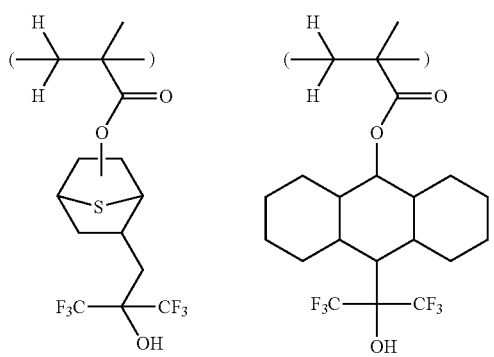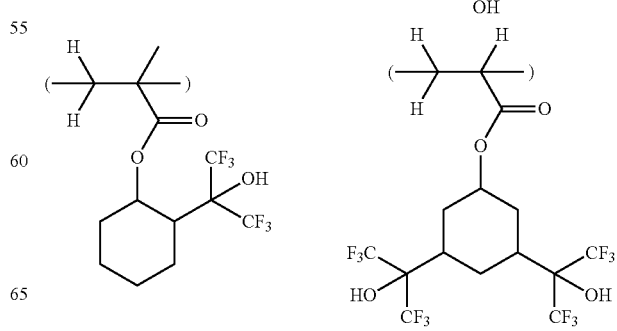

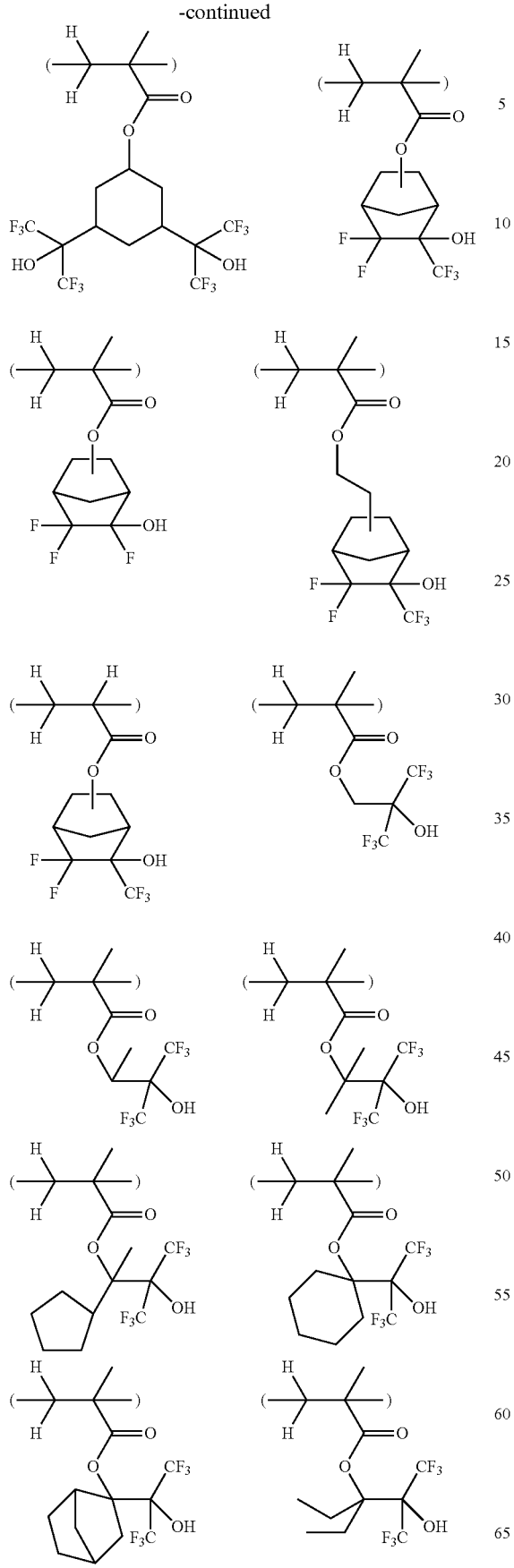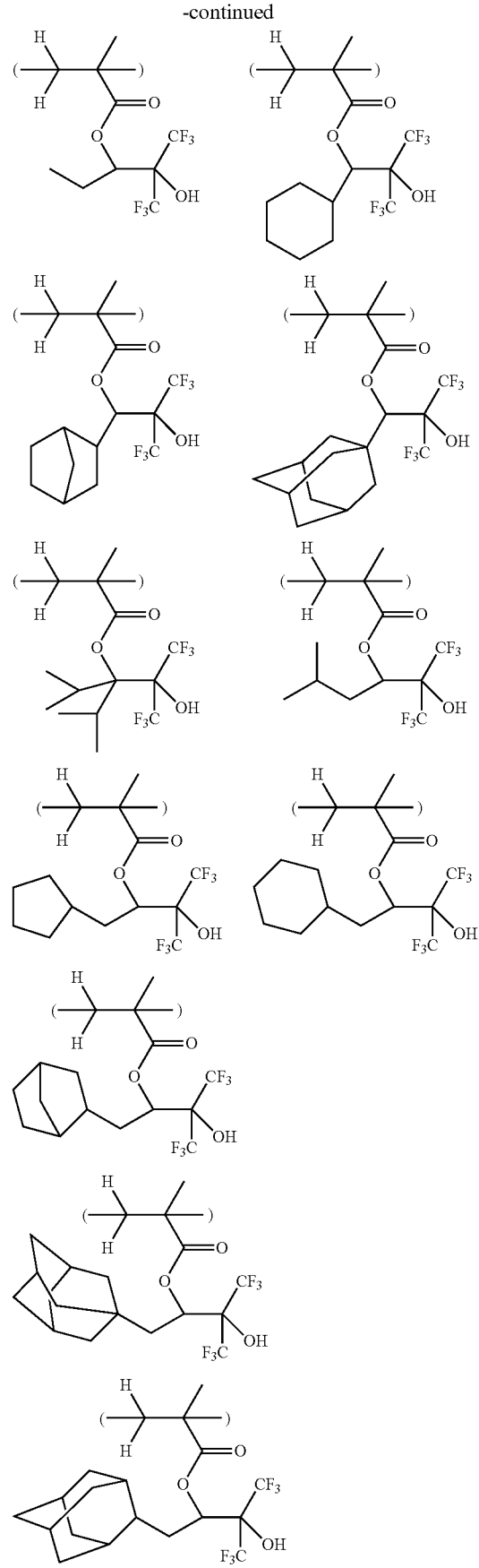

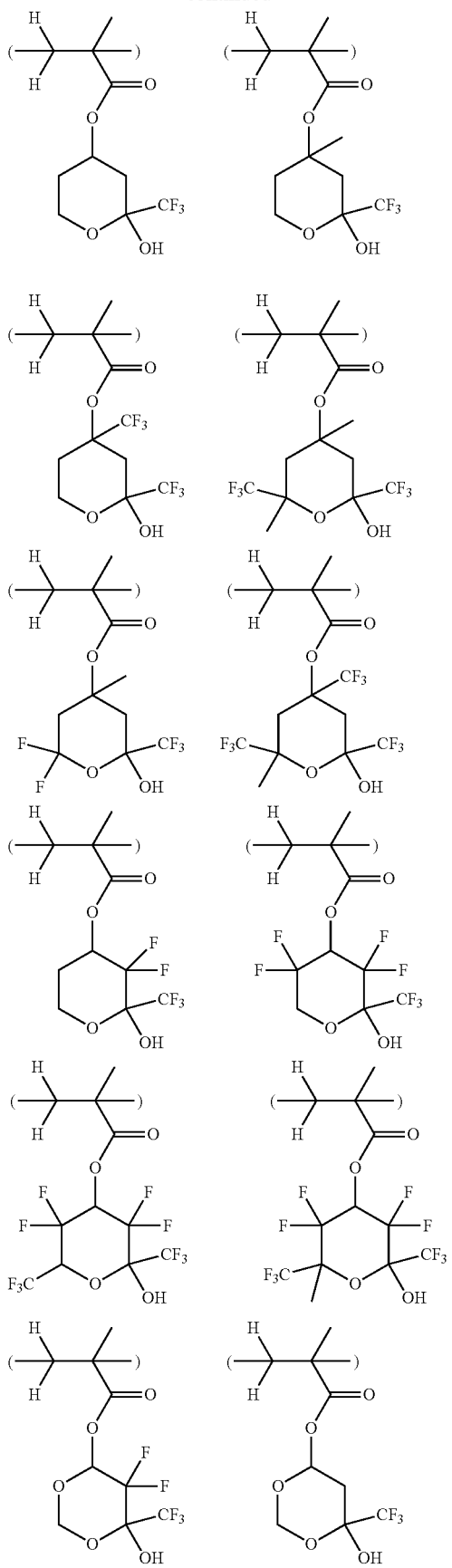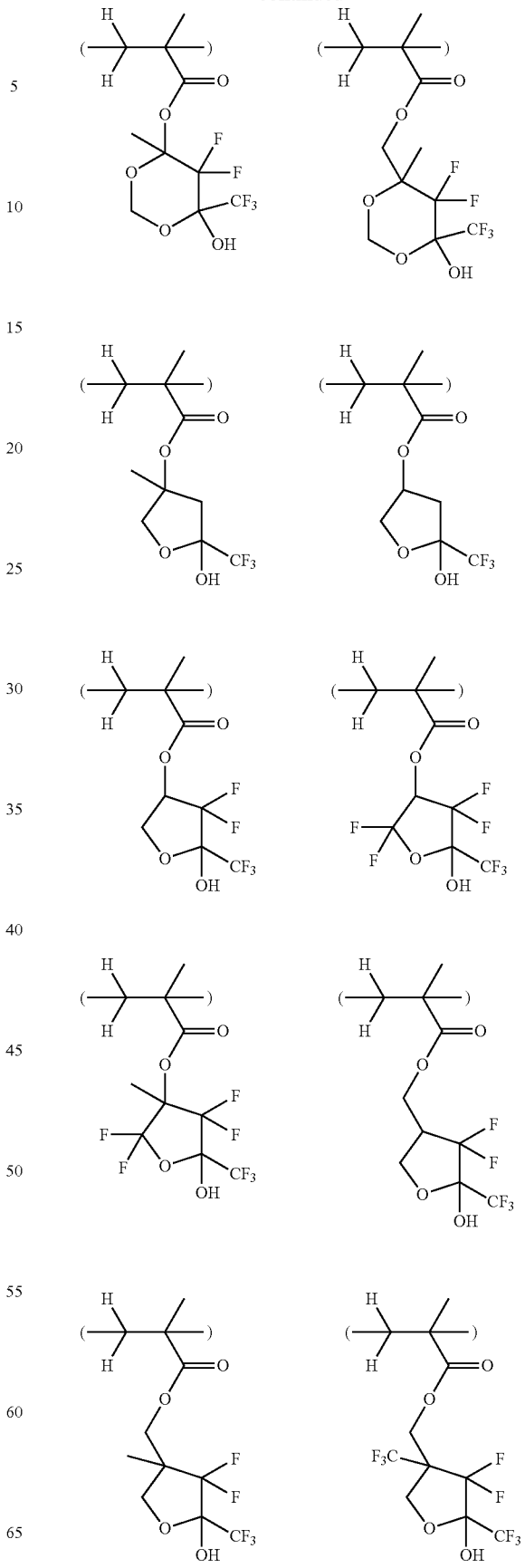

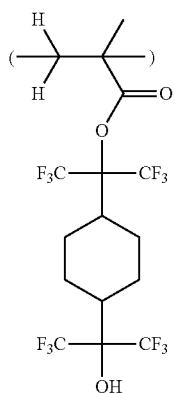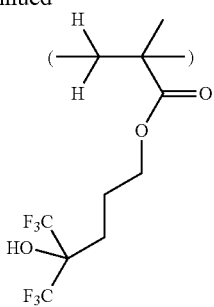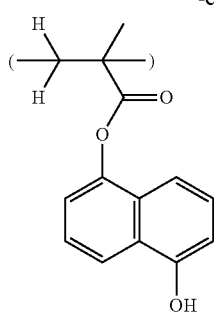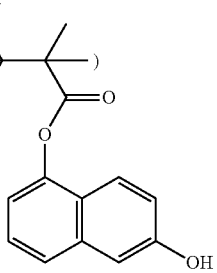
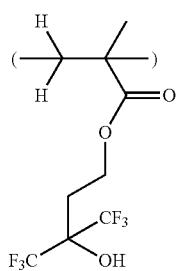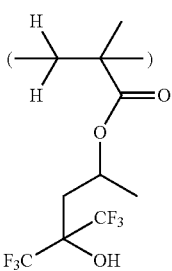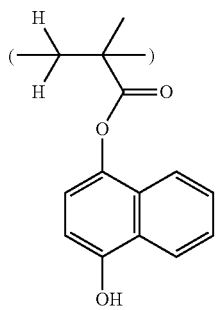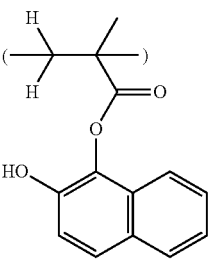
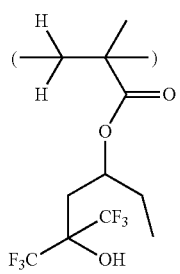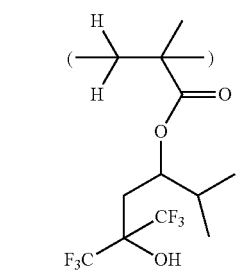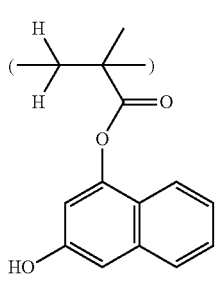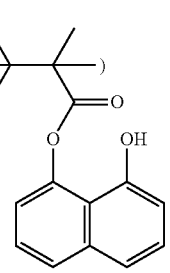
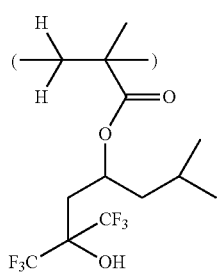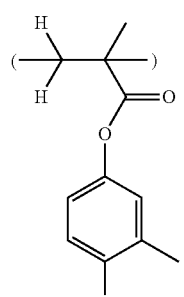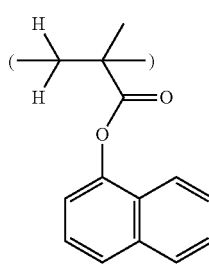
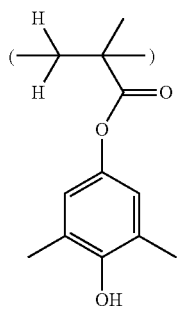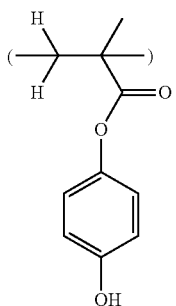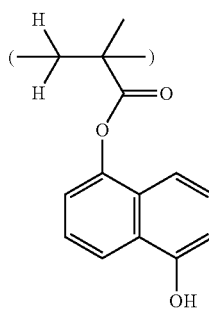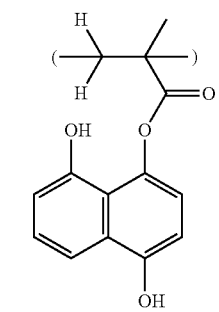

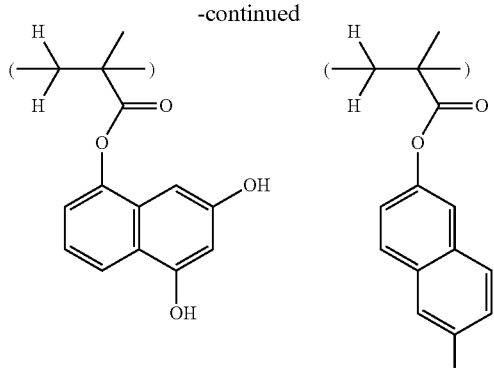
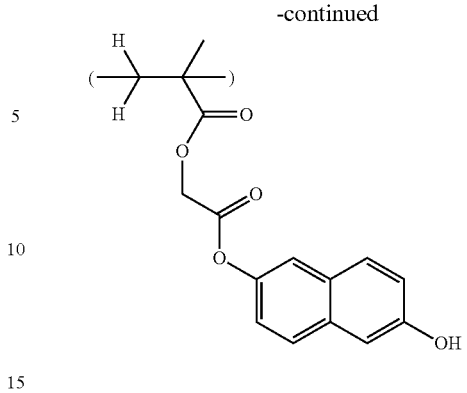
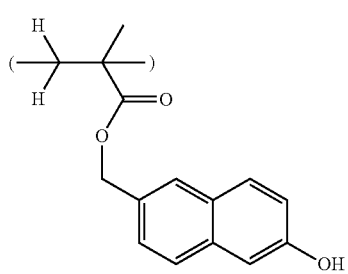
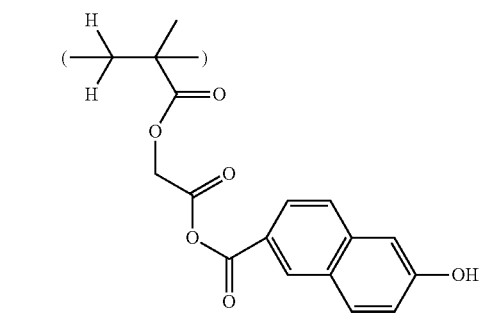
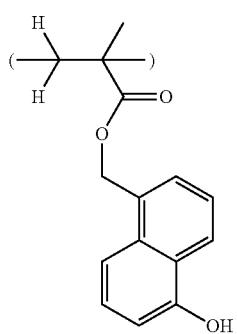
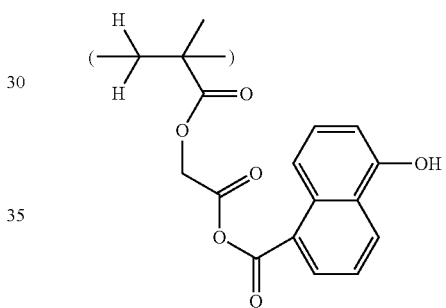
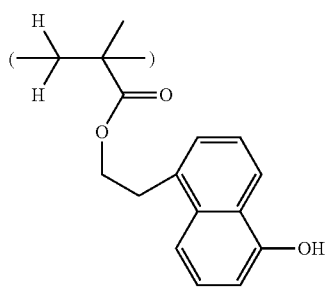
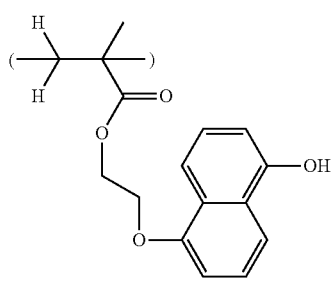
Where the recurring units of formula (3) are incorporated, units having lactone ring as the polar group are most preferably used.
While the polymer is characterized by comprising recurring units having formulae (2) and (3), optionally recurring units having the general formula (d1) or (d2) may also be incorporated.
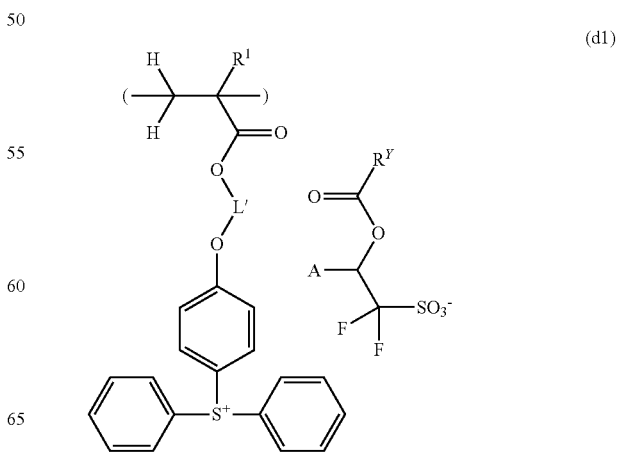
(d1)

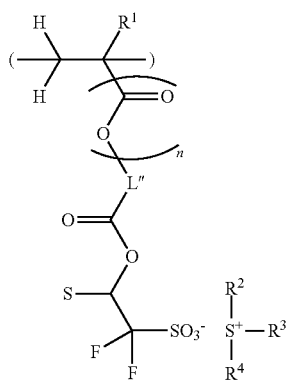

(d2)

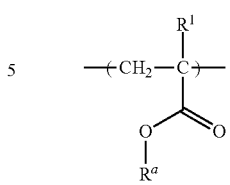

(1a)

In formula (1a), $R^1$ is as defined above; $R^a$ is a straight, branched or cyclic $C_1$-$C_{20}$ monovalent hydrocarbon group which may be substituted with or separated by a heteroatom, with the proviso that the monovalent hydrocarbon group of $R^a$ has 1, 2, 3 or 4 substituent groups having the general formula (1b).

----$OR^b$ (1b)

Herein $R^b$ is an acid labile group, and the broken line designates a valence bond.

Illustrative examples of the recurring units having formula (1a) are given below, but not limited thereto.

Herein $R^1$, $R^2$, $R^3$, and $R^4$ are as defined above. L' is a single bond or $C_2$-$C_5$ alkylene group. $R^Y$ is a straight $C_1$-$C_{20}$ or branched or cyclic $C_3$-$C_{20}$ monovalent hydrocarbon group which may be substituted with or separated by a heteroatom. A is hydrogen or trifluoromethyl. L" is a single bond or a straight $C_1$-$C_{20}$ or branched or cyclic $C_3$-$C_{20}$ divalent hydrocarbon group which may be substituted with or separated by a heteroatom, n is 0 or 1, with the proviso that n is 0 when L" is a single bond.

In formula (d1), $R^1$ is as defined and exemplified above. L' is a single bond or $C_2$-$C_5$ alkylene group, preferably ethylene, propylene or butylene. A is hydrogen or trifluoromethyl, preferably trifluoromethyl. $R^Y$ is a straight $C_1$-$C_{20}$ or branched or cyclic $C_3$-$C_{20}$ monovalent hydrocarbon group which may be substituted with or separated by a heteroatom, examples of which are as described above.

Illustrative structures of the anion moiety in formula (d1) include those described in JP-A 2010-113209 and JP-A 2007-145797.

In formula (d2), $R^1$, $R^2$, $R^3$, $R^4$, and A are as defined and exemplified above. L" is a single bond or a straight $C_1$-$C_{20}$ or branched or cyclic $C_3$-$C_{20}$ divalent hydrocarbon group which may be substituted with or separated by a heteroatom, n is 0 or 1, with the proviso that n must be 0 when L" is a single bond.

Illustrative structures of the anion moiety in formula (d1) wherein A is hydrogen include those described in JP-A 2010-116550. Illustrative structures of the anion moiety in formula (d1) wherein A is trifluoromethyl include those described in JP-A 2010-077404.

While the polymer is characterized by comprising recurring units having formulae (2) and (3), and optionally recurring units having the general formula (d1) or (d2), other recurring units, typically recurring units of the structure having a hydroxyl group protected with an acid labile group may be further copolymerized. The recurring units of the structure having a hydroxyl group protected with an acid labile group are not particularly limited as long as the unit has one or more structures each having protected hydroxyl wherein the protective group is decomposed under the action of acid to generate a hydroxyl group. Of these, recurring units of the structure having the general formula (1a) are preferred.

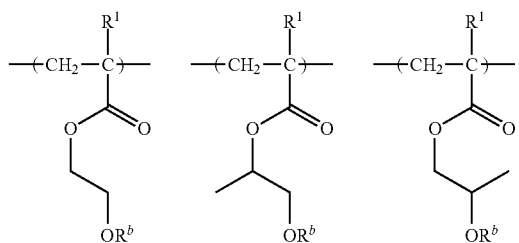

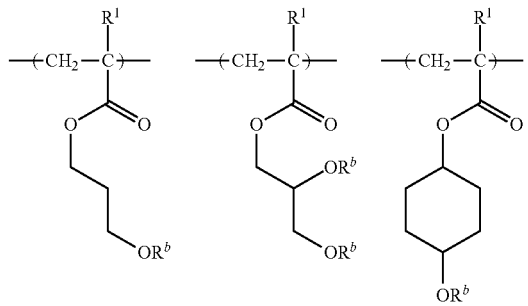

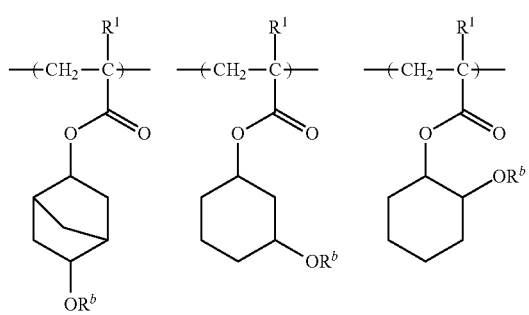

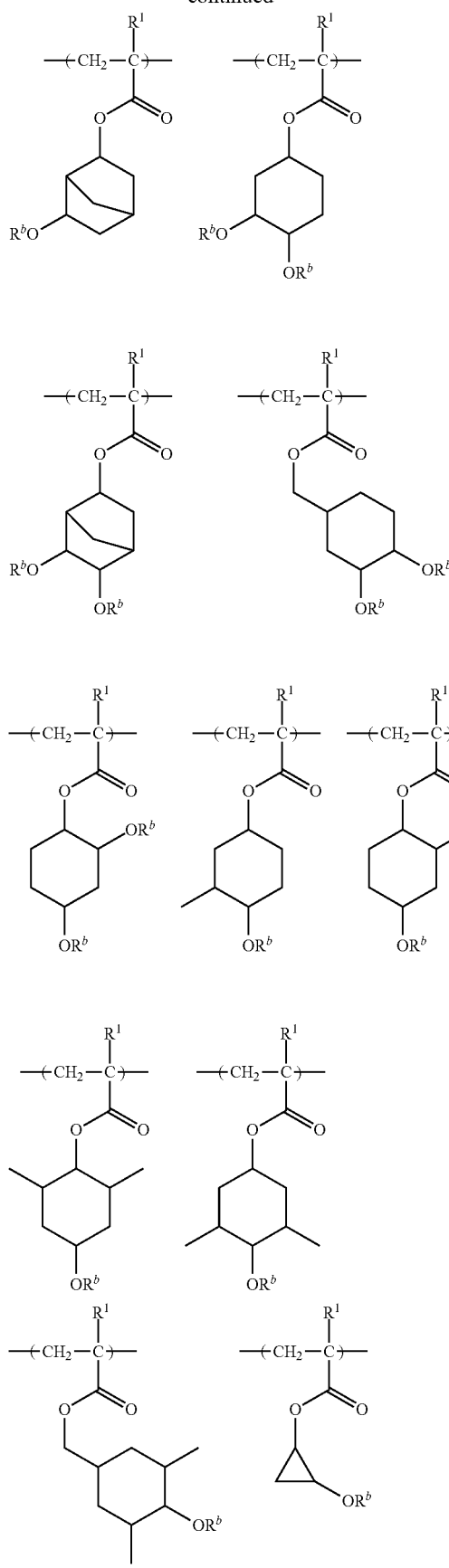
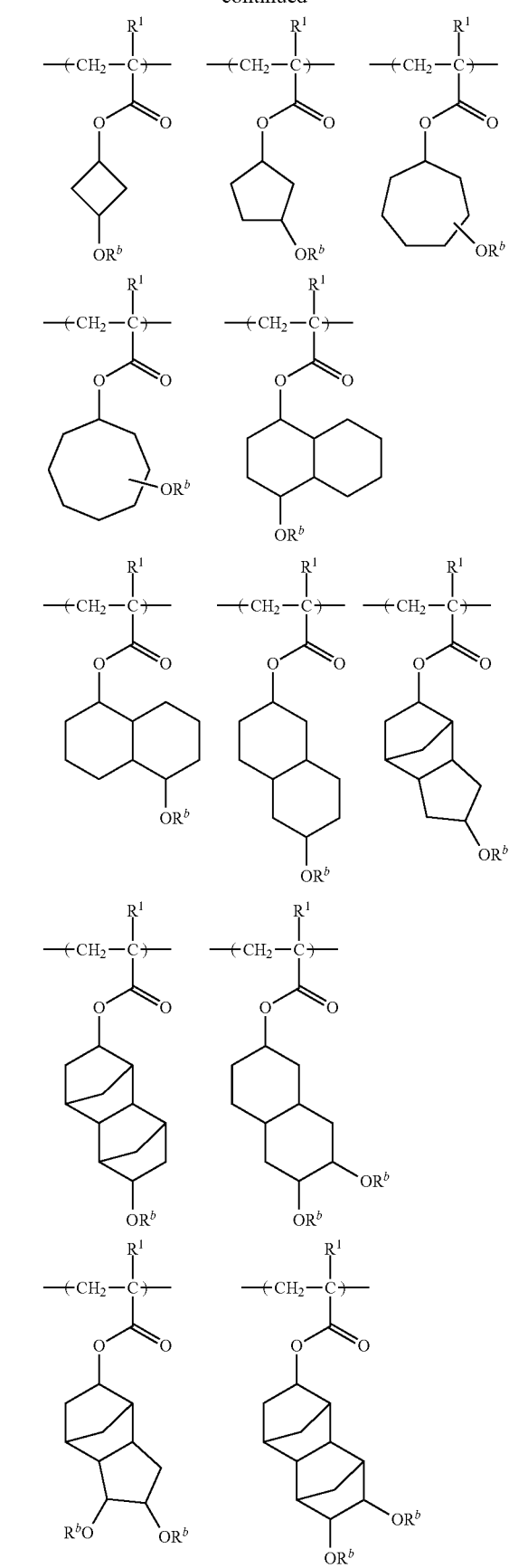

77
-continued
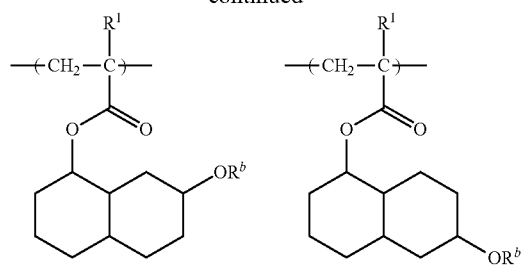
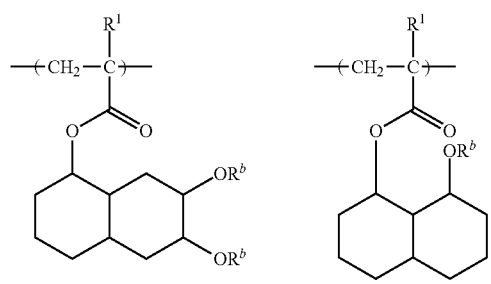
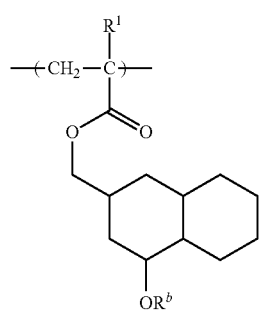
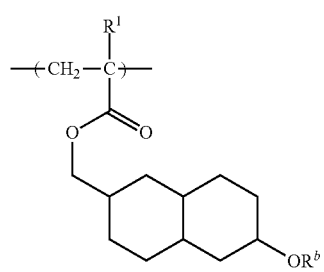
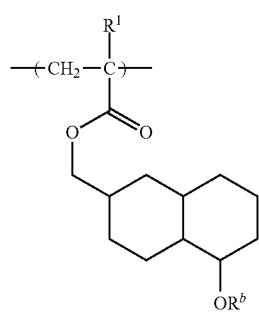
78
-continued
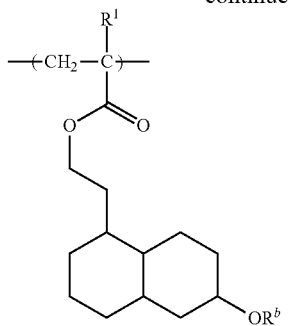
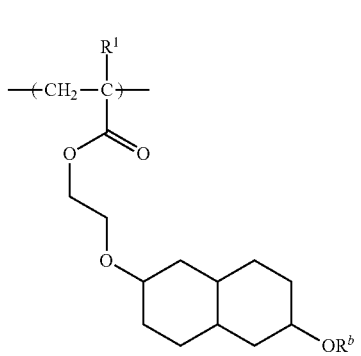
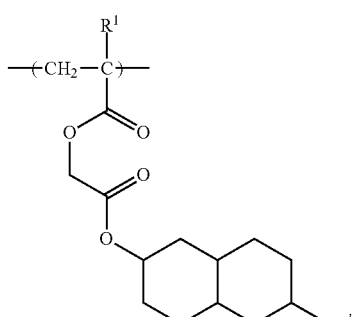
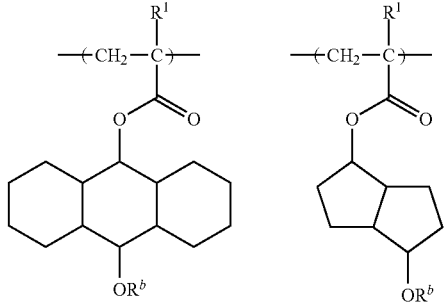
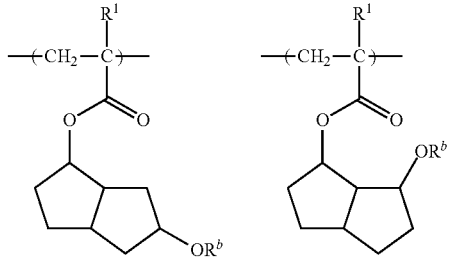

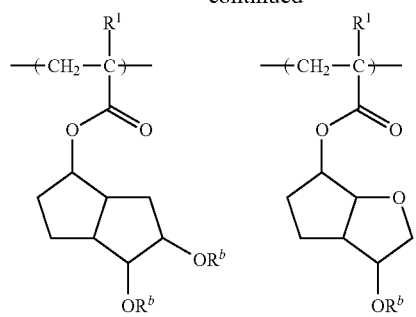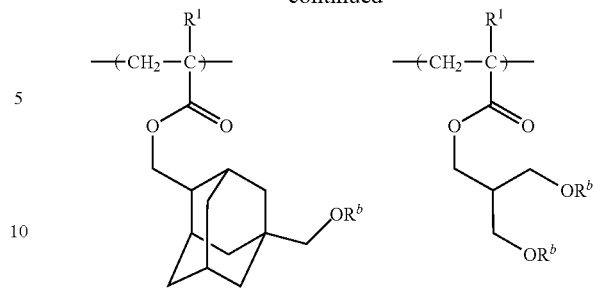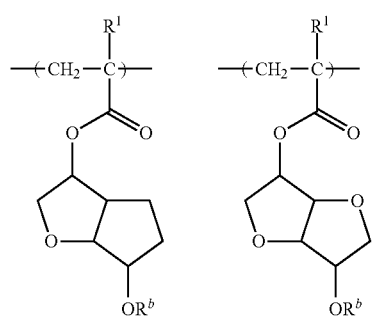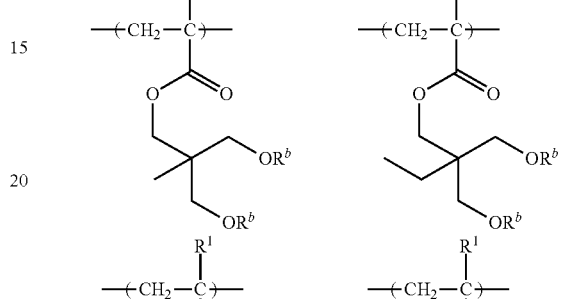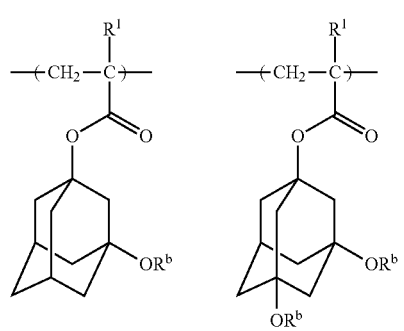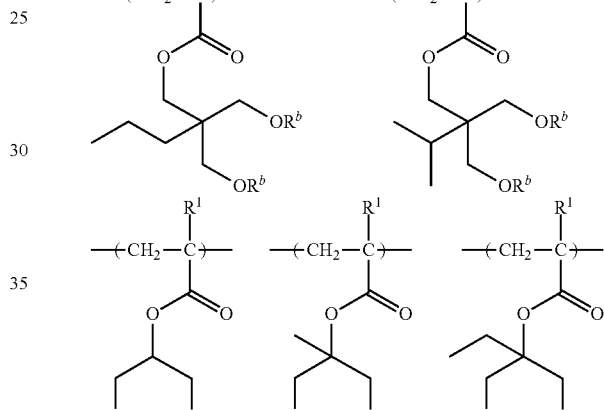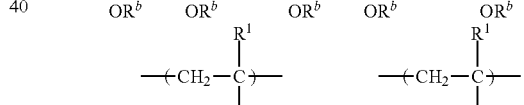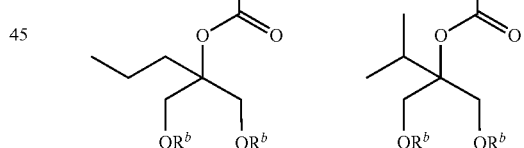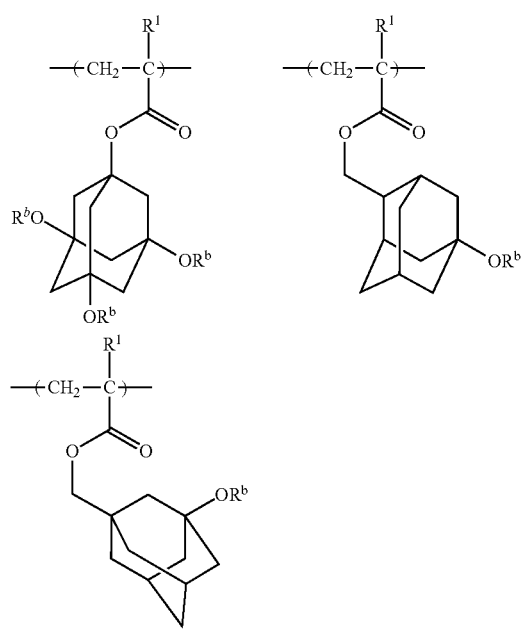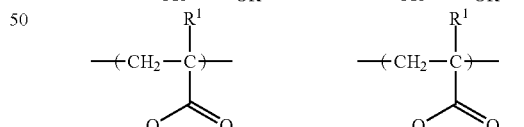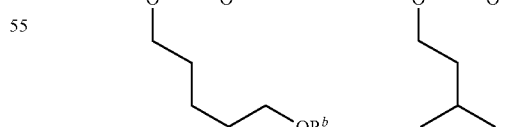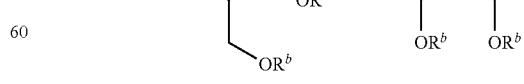
Herein, $R^1$ and $R^b$ are as defined above.
The acid labile group $R^b$ in formula (1b) is not particularly limited as long as it is deprotected under the action of acid to generate a hydroxyl group. Suitable acid labile groups include acetal structure groups, ketal structure groups, and alkoxycarbonyl groups, examples of which are shown below.

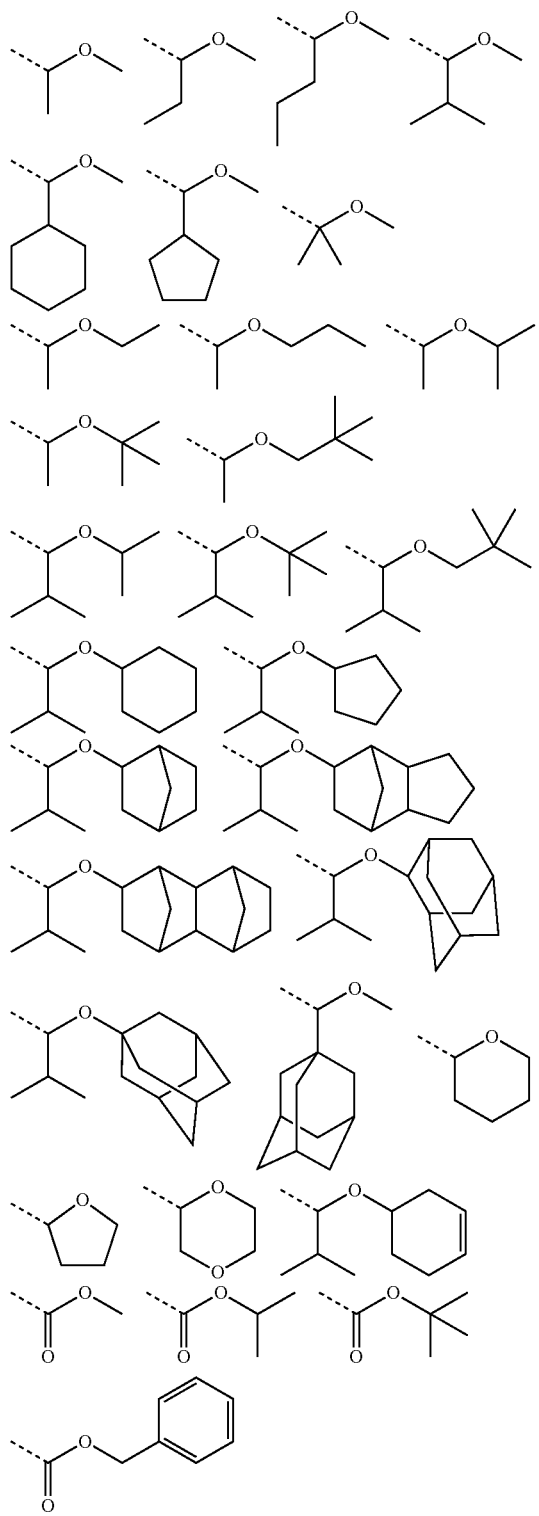

Herein the broken line designates a valence bond.

Of the acid labile groups represented by $R^b$ in formula (1b), alkoxymethyl groups having the general formula (1c) are most preferred.

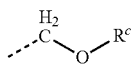

(1c)

Herein the broken line designates a valence bond. $R^c$ is a straight, branched or cyclic $C_1$-$C_{15}$ monovalent hydrocarbon group.

Illustrative examples of the acid labile group having formula (1c) are given below, but not limited thereto.

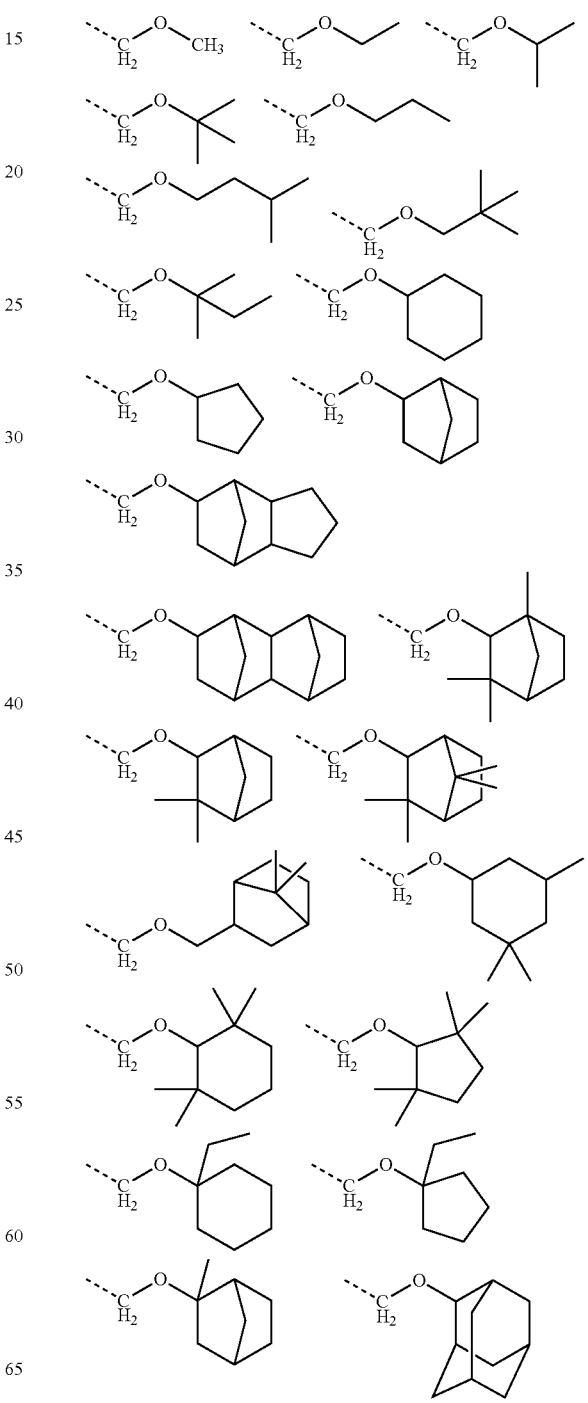

-continued

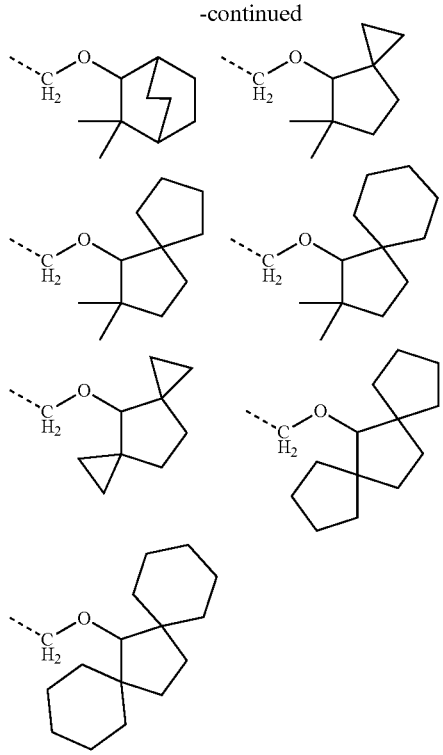

The polymer used herein may have additional recurring units further copolymerized therein. Suitable additional recurring units are derived from substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1.1$^{3,6}$.0$^{2,7}$]dodecene derivatives, unsaturated acid anhydrides such as itaconic anhydride, and other monomers. As the hydrogenated ROMP polymer, those described in JP-A 2003-066612 may be used.

The polymer used herein generally has a weight average molecular weight (Mw) of 1,000 to 500,000, and preferably 3,000 to 100,000, as measured by GPC using polystyrene standards. Outside the range, there may result an extreme drop of etch resistance, and a drop of resolution due to difficulty to gain a dissolution rate difference before and after exposure.

The polymer may be synthesized by any desired method, for example, by dissolving an unsaturated bond-containing monomer or monomers in an organic solvent, adding a radical initiator, and effecting heat polymerization. Suitable organic solvents used herein include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours. The acid labile group that has been incorporated in the monomer may be kept as such, or the polymer may be protected or partially protected therewith at the end of polymerization.

In the polymer (B), appropriate molar fractions (mol %) of the respective recurring units derived from the monomers are given below although the invention is not limited thereto. The polymer may comprise:

I) constituent units of at least one type having formula (2) in a fraction of 1 to 60 mol %, preferably 5 to 50 mol %, and more preferably 10 to 50 mol %, II) constituent units of at least one type having formula (3) in a fraction of 40 to 99 mol %, preferably 50 to 95 mol %, and more preferably 50 to 90 mol %, and optionally, III) constituent units of at least one type having formula (d1) or (d2) in a fraction of 0 to 30 mol %, preferably 0 to 20 mol %, and more preferably 0 to 10 mol %, and optionally, IV) constituent units of at least one type derived from another monomer in a fraction of 0 to 80 mol %, preferably 0 to 70 mol %, and more preferably 0 to 50 mol %.

(C) PAG of Formula (4)

While the resist composition of the invention essentially comprises the carboxylic acid sulfonium salt having formula (1), it preferably further comprises a photoacid generator (PAG) having the general formula (4).

Herein $R^2$, $R^3$, and $R^4$ are as defined above. $X^-$ is an anion of the general formula (5), (6), (7) or (8).

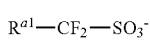

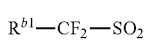

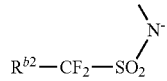

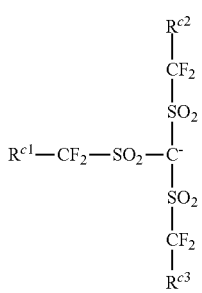

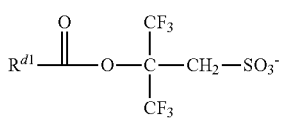

Herein $R^{a1}$, $R^{b1}$, $R^{b2}$, $R^{c1}$, $R^{c2}$, and $R^{c3}$ are each independently fluorine or a straight $C_1$-$C_{40}$ or branched or cyclic $C_3$-$C_{40}$ monovalent hydrocarbon group which may be substituted with or separated by a heteroatom. A pair of $R^{b1}$ and $R^{b2}$, or $R^{c1}$ and $R^{c2}$ may bond together to form a ring with —$CF_2$— $SO_2$— group to which they are attached. $R^{d1}$ is a straight $C_1$-$C_{40}$ or branched or cyclic $C_3$-$C_{40}$ monovalent hydrocarbon group which may be substituted with or separated by a heteroatom.

In formula (5), $R^{a1}$ is fluorine or a straight $C_1$-$C_{40}$ or branched or cyclic $C_3$-$C_{40}$ monovalent hydrocarbon group which may be substituted with or separated by a heteroatom.

Of the structures of formula (5), a structure having the general formula (5') is preferred.

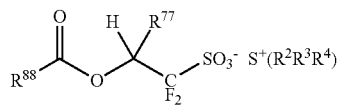

(5')

Herein $R^{77}$ is hydrogen or trifluoromethyl; $R^{88}$ is a straight $C_1$-$C_{30}$ or branched or cyclic $C_3$-$C_{30}$ monovalent hydrocarbon group which may be substituted with or separated by a heteroatom; $R^2$, $R^3$ and $R^4$ are as defined above.

In formula (5'), $R^{77}$ is hydrogen or trifluoromethyl, preferably trifluoromethyl. $R^2$, $R^3$ and $R^4$ are as defined above. $R^{88}$ is a straight $C_1$-$C_{30}$ or branched or cyclic $C_3$-$C_{30}$ monovalent hydrocarbon group which may be substituted with or separated by a heteroatom. Of the heteroatoms contained in $R^{88}$, oxygen, nitrogen, sulfur and halogen atoms are preferred, with oxygen being most preferred. Of the monovalent hydrocarbon groups represented by $R^{88}$, those groups of 6 to 30 carbon atoms are preferred from the aspect of achieving a high resolution in forming a micro-pattern. Suitable monovalent hydrocarbon groups represented by $R^{88}$ include, but are not limited to, methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoromethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of sulfonium salts having formula (5'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the preferred PAG are shown below.

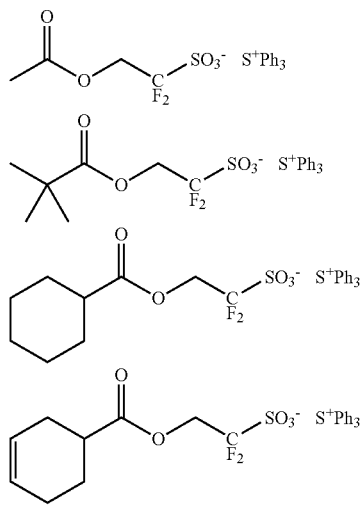

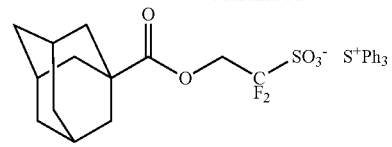

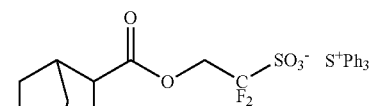

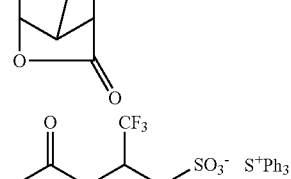

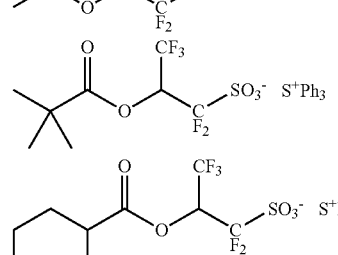

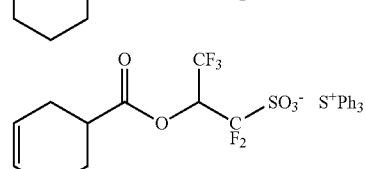

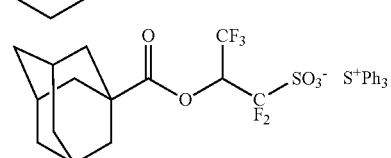

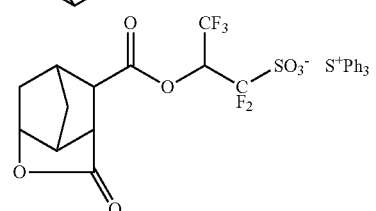

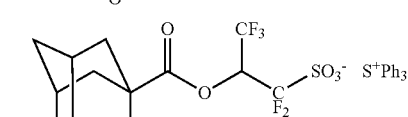

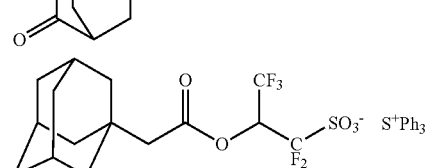

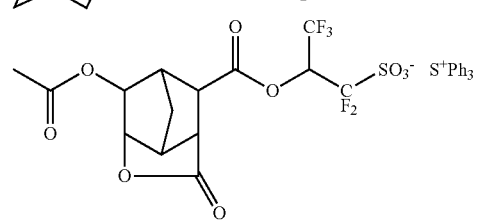

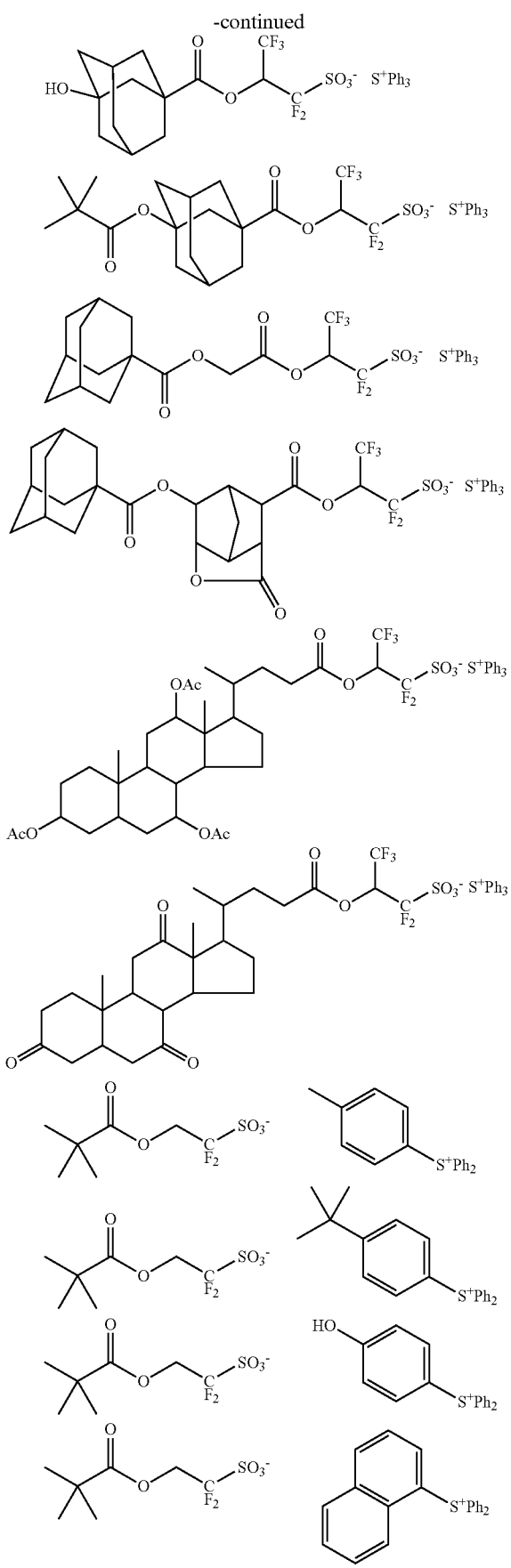
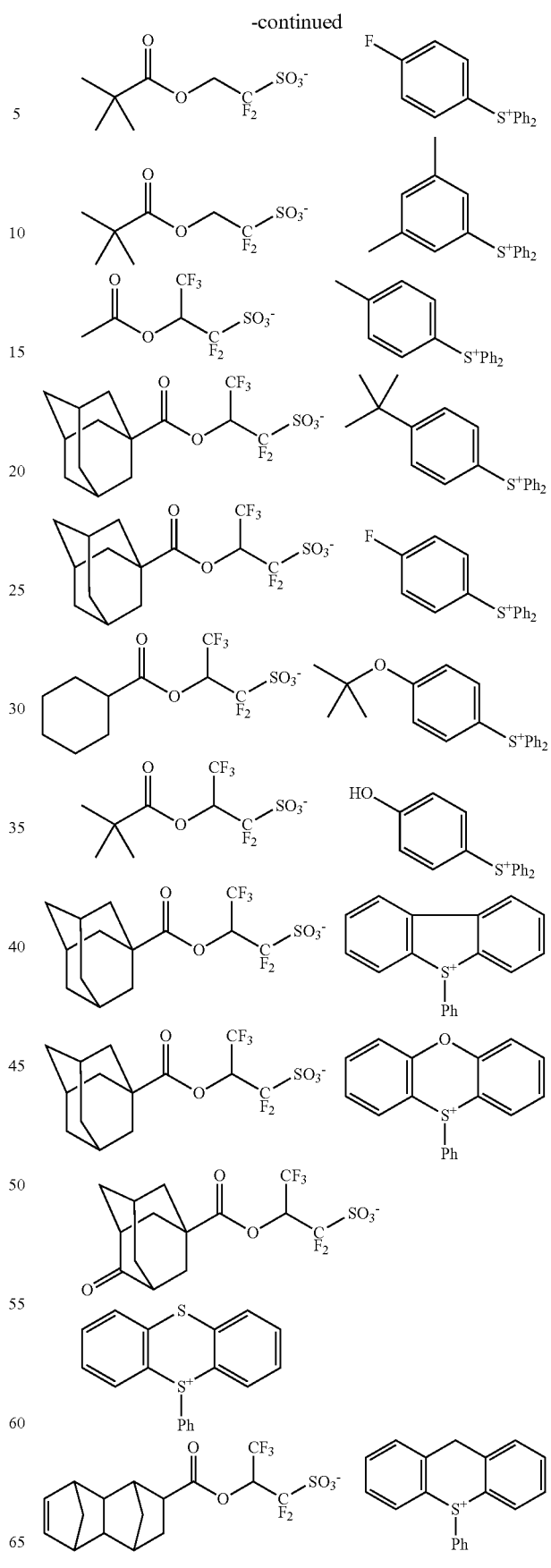

In formula (6), $R^{b1}$ and $R^{b2}$ are each independently fluorine or a straight $C_1$-$C_{40}$ or branched or cyclic $C_3$-$C_{40}$ monovalent hydrocarbon group which may be substituted with or separated by a heteroatom. Illustrative examples of the monovalent hydrocarbon group are as exemplified for $R^{a1}$. Preferably $R^{b1}$ and $R^{b2}$ are fluorine or $C_1$-$C_4$ straight fluorinated alkyl groups. Also, $R^{b1}$ and $R^{b2}$ may bond together to form a ring with the linkage: —$CF_2$—$SO_2$—$N^-$—$SO_2$—$CF_2$— to which they are attached. It is preferred to form a ring structure via a fluorinated ethylene or fluorinated propylene group.

In formula (7), $R^{c1}$, $R^{c2}$ and $R^{c3}$ are each independently fluorine or a straight $C_1$-$C_{40}$ or branched or cyclic $C_3$-$C_{40}$ monovalent hydrocarbon group which may be substituted with or separated by a heteroatom. Illustrative examples of the monovalent hydrocarbon group are as exemplified for $R^{a1}$. Preferably $R^{c1}$, $R^{c2}$ and $R^{c3}$ are fluorine or $C_1$-$C_4$ straight fluorinated alkyl groups. Also, $R^{c1}$ and $R^{c2}$ may bond together to form a ring with the linkage: —$CF_2$—$SO_2$—$C^-$—$SO_2$—$CF_2$— to which they are attached. It is preferred to form a ring structure via a fluorinated ethylene or fluorinated propylene group.

In formula (8), $R^{d1}$ is a straight $C_1$-$C_{40}$ or branched or cyclic $C_3$-$C_{40}$ monovalent hydrocarbon group which may be substituted with or separated by a heteroatom. Of the heteroatoms contained in $R^{d1}$, oxygen, nitrogen, sulfur and halogen atoms are preferred, with oxygen being most preferred. Of the monovalent hydrocarbon groups represented by $R^{d1}$, those groups of 6 to 30 carbon atoms are preferred from the aspect of achieving a high resolution in forming a micro-pattern. Suitable monovalent hydrocarbon groups represented by $R^{d1}$ include, but are not limited to, methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of sulfonium salts having the anion of formula (8), reference may be made to JP-A 2010-215608.

Examples of the preferred PAG are shown below.

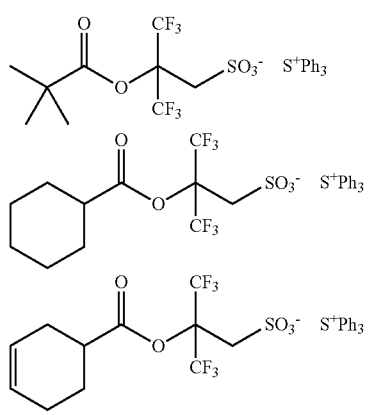

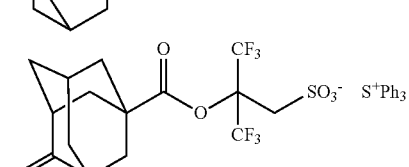

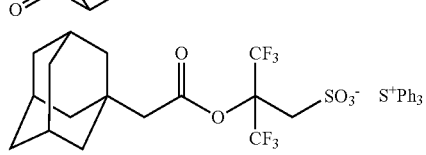

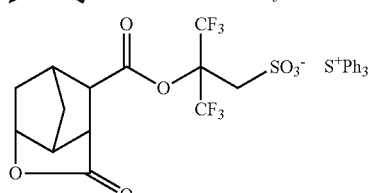

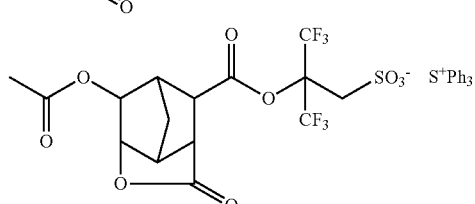

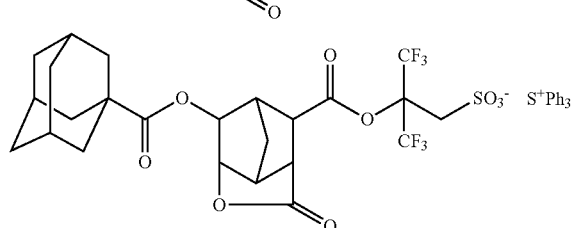

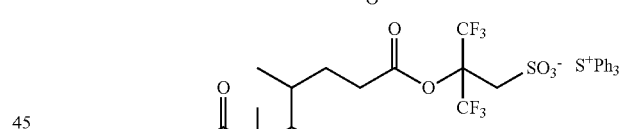

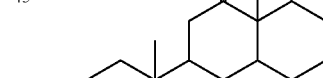

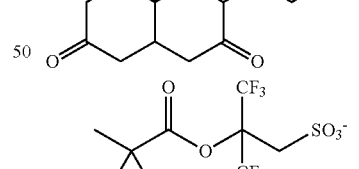

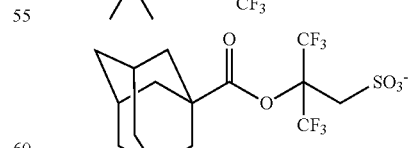

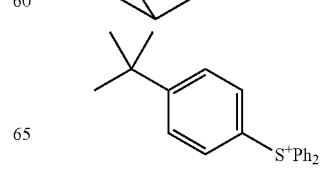

-continued

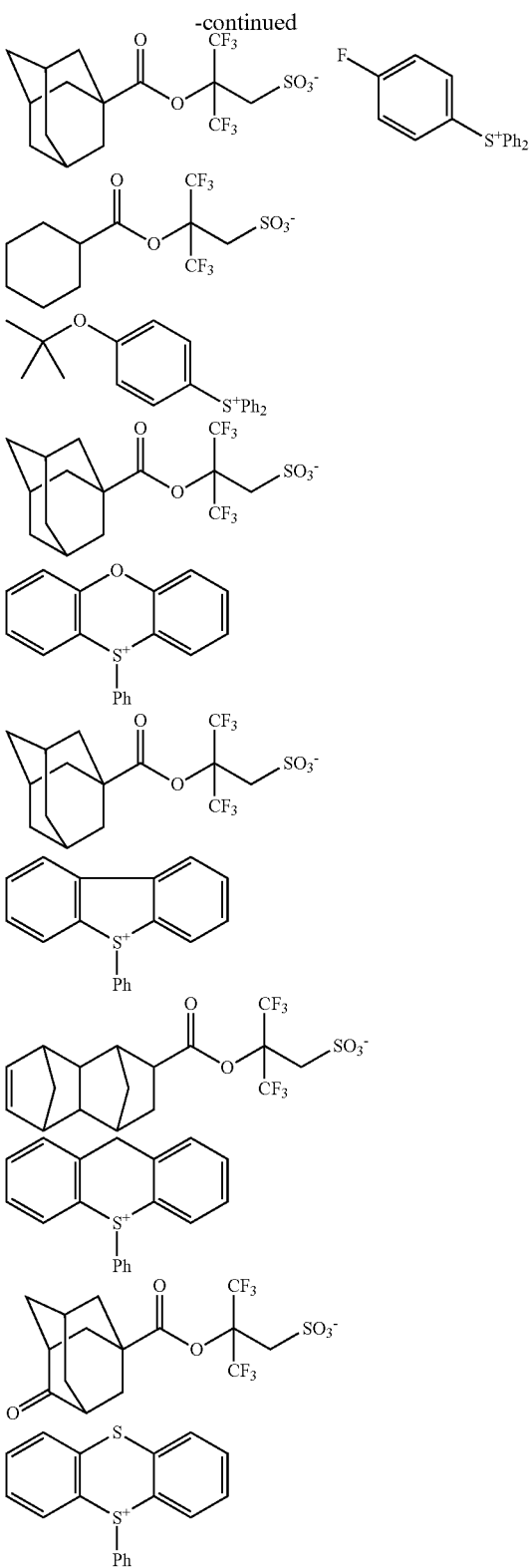

Notably, the compound having the anion of formula (8) does not have fluorine at the α-position relative to the sulfo group, but two trifluoromethyl groups at the β-position. For this reason, it has a sufficient acidity to sever the acid labile groups in the resist polymer. Thus the compound is an effective PAG.

Of the foregoing PAG's, those compounds having the structure of formula (5') or formula (8) are preferred because of suppressed acid diffusion and high solubility in the resist solvent.

The amount of the PAG (C) added is preferably 0 to 40 parts, specifically 0.1 to 40 parts if used, more preferably 0.1 to 20 parts by weight per 100 parts by weight of the base resin. Too large an amount of the PAG may give rise to problems such as degraded resolution and foreign particles during development and resist film stripping.

(D) Nitrogen-Containing Compound

To the resist composition, a nitrogen-containing compound may be added as the quencher. The inclusion of the nitrogen-containing compound holds down the diffusion rate at which the acid generated by PAG diffuses within the resist film. Suitable nitrogen-containing compounds include primary, secondary and tertiary amine compounds, specifically amine compounds having a hydroxyl group, ether bond, ester bond, lactone ring, cyano group or sulfonate bond, as described in JP-A 2008-111103, paragraphs [0146] to [0164] (U.S. Pat. No. 7,537,880). Also useful are compounds whose primary or secondary amine is protected in carbamate form as described in JP 3790649.

The quenchers may be used alone or in admixture of two or more. The quencher is preferably used in an amount of 0.001 to 12 parts, more preferably 0.01 to 8 parts by weight per 100 parts by weight of the base resin. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of quencher is also effective for improving adhesion to the substrate.

Also, a PAG having a nitrogen-containing substituent may be used in combination. This compound functions as quencher in the unexposed region and as so-called photo-degradable base, which loses quencher ability through neutralization with the acid generated by itself, in the exposed region. The use of photo-degradable base is effective for enhancing the contrast between exposed and unexposed regions. With respect to the photo-degradable base, reference may be made to JP-A 2009-109595 and JP-A 2012-046501, for example.

(E) Organic Solvent

The organic solvent (E) used herein may be any organic solvent in which the polymer (base resin), PAG, quencher, and other components are soluble. Examples of the organic solvent include ketones such as cyclohexanone and methyl 2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, and mixtures thereof, as described in JP-A 2008-111103, paragraphs [0144] to [0145]. Where an acid labile group of acetal type is used, a high-boiling alcohol solvent may be added for accelerating deprotection reaction of acetal, for example, diethylene glycol, propylene glycol, glycerol, 1,4-butanediol, or 1,3-butanediol. Of the above organic solvents, it is recommended to use 1-ethoxy-2-propanol, PGMEA, cyclohexanone, γ-butyrolactone, and mixtures thereof because the acid generator is most soluble therein.

An appropriate amount of the organic solvent used is 200 to 5,000 parts, more preferably 400 to 3,000 parts by weight per 100 parts by weight of the base resin.

(F) Surfactant which is Insoluble or Substantially Insoluble in Water and Soluble in Alkaline Developer, and/or a Surfactant which is Insoluble or Substantially Insoluble in Water and Alkaline Developer (Hydrophobic Resin)

To the resist composition, the surfactant (F) may be added. Reference should be made to those compounds defined as component (S) in JP-A 2010-215608 and JP-A 2011-16746.

While many examples of the surfactant which is insoluble or substantially insoluble in water and alkaline developer are described in these patent documents, preferred examples are FC-4430, Surflon S-381, Surfynol E1004, KH-20 and KH-30, which may be used alone or in admixture. Partially fluorinated oxetane ring-opened polymers having the structural formula (surf-1) are also useful.

the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage. Suitable polymeric surfactants are shown below.

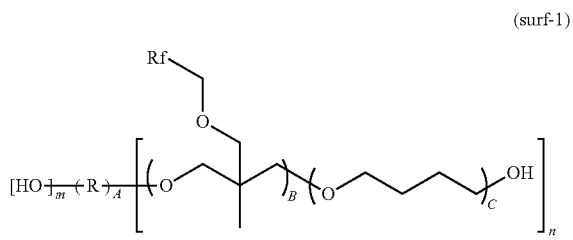

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

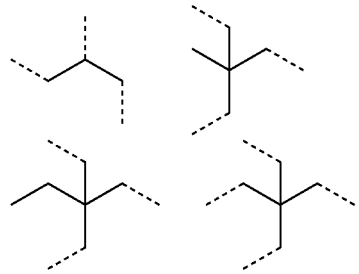

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in

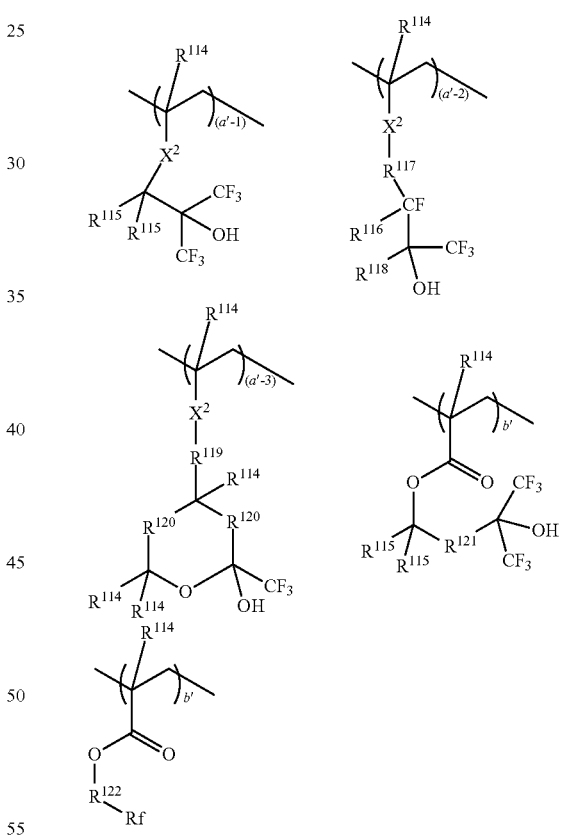

Herein $R^{114}$ is each independently hydrogen, fluorine, methyl or trifluoromethyl. $R^{115}$ is each independently hydrogen or a straight, branched or cyclic $C_1$-$C_{20}$ alkyl or fluoroalkyl group, or two $R^{115}$ in a common monomer may bond together to form a ring with the carbon atom to which they are attached, and in this event, they together represent a straight, branched or cyclic $C_2$-$C_{20}$ alkylene or fluoroalkylene group. $R^{116}$ is fluorine or hydrogen, or $R^{116}$ may bond with $R^{117}$ to form a non-aromatic ring of 3 to 10 carbon atoms in total with the carbon atom to which they are attached. $R^{117}$ is a straight, branched or cyclic $C_1$-$C_6$ alkylene group in which at least one hydrogen atom may be substituted by a fluorine atom. $R^{118}$ is a straight or branched $C_1$-$C_{10}$ alkyl group in which at least one hydrogen atom is substituted by a fluorine atom. Alternatively, $R^{117}$ and $R^{118}$ may bond together to form a non-aromatic ring with the carbon atoms to which they are attached. In this event, $R^{117}$, $R^{112}$ and the carbon atoms to which they are attached together represent a trivalent organic group of 2 to 12 carbon atoms in total. $R^{119}$ is a single bond or a $C_1$-$C_4$ alkylene. $R^{120}$ is each independently a single bond, —O—, or —$CR^{114}R^{114}$—. $R^{121}$ is a straight or branched $C_1$-$C_4$ alkylene group, or may bond with $R^{115}$ within a common monomer to form a $C_3$-$C_6$ non-aromatic ring with the carbon atom to which they are attached. $R^{122}$ is 1,2-ethylene, 1,3-propylene, or 1,4-butylene. Rf is a linear perfluoroalkyl group of 3 to 6 carbon atoms, typically 3H-perfluoropropyl, 4H-perfluorobutyl, 5H-perfluoropentyl, or 6H-perfluorohexyl. $X^2$ is each independently —C(=O)—O—, —O—, or —C(=O)—$R^{123}$—C(=O)—O—. $R^{123}$ is a straight, branched or cyclic $C_1$-$C_{10}$ alkylene group. The subscripts are in the range:

$0 \leq (a'\text{-}1) < 1$, $0 \leq (a'\text{-}2) < 1$, $0 \leq (a'\text{-}3) < 1$, $0 < (a'\text{-}1)+(a'\text{-}2)+(a'\text{-}3) < 1$, $0 \leq b' < 1$, $0 \leq c' < 1$, and $0 < (a'\text{-}1)+(a'\text{-}2)+(a'\text{-}3)+b'+c' \leq 1$.

Exemplary units are shown below.

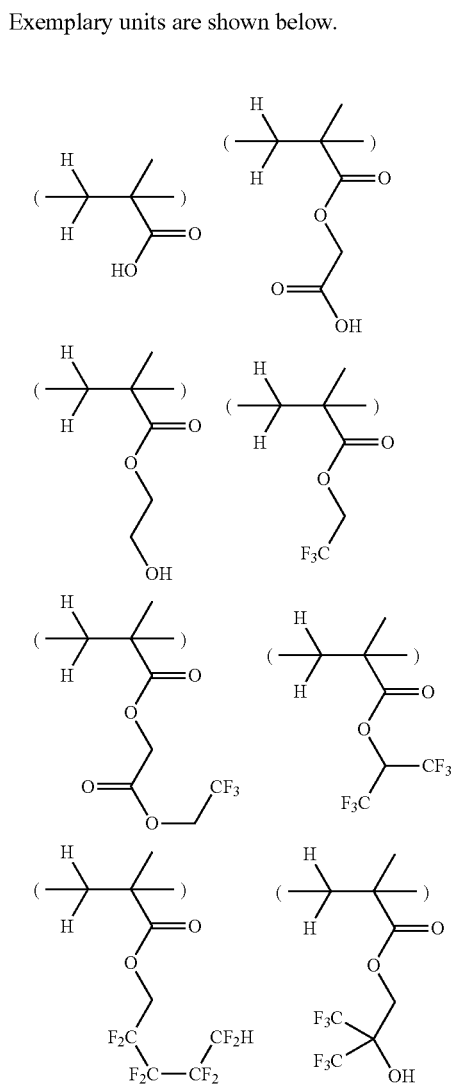

-continued

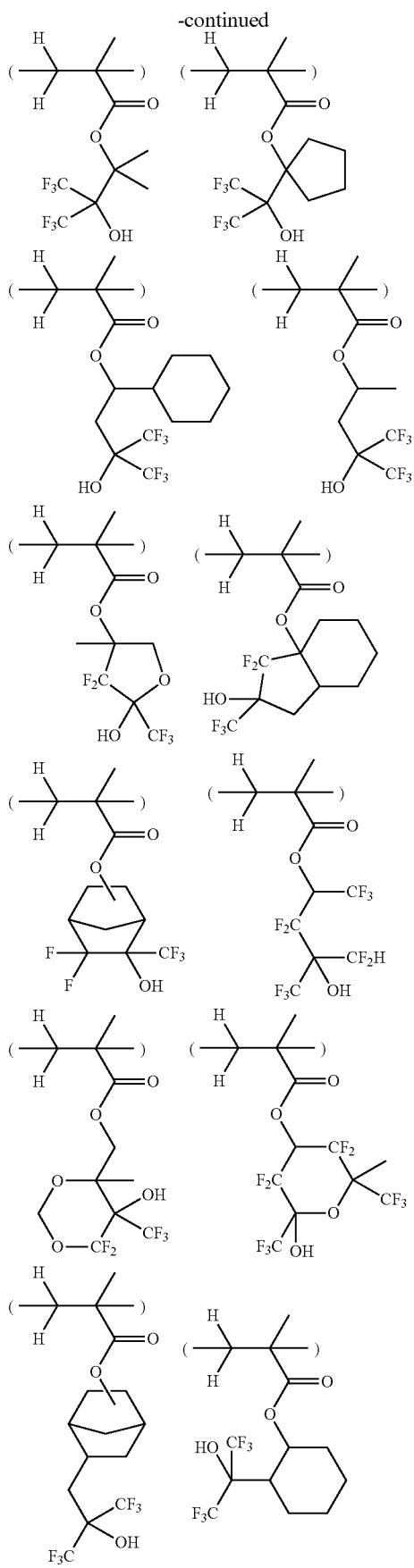

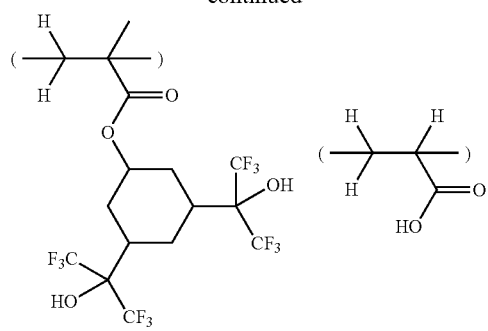
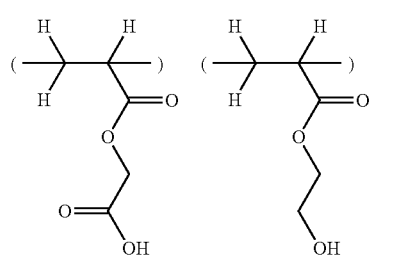
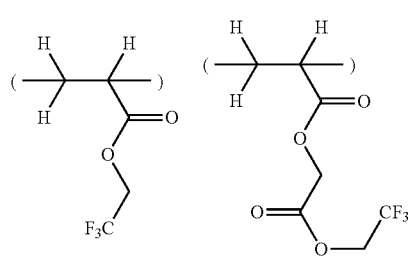
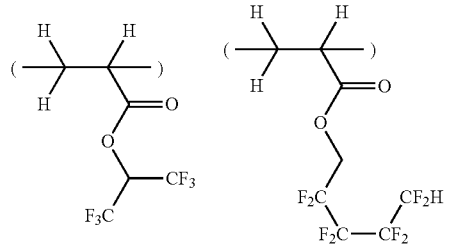
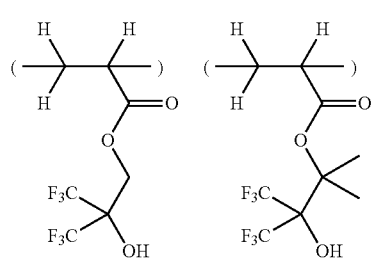
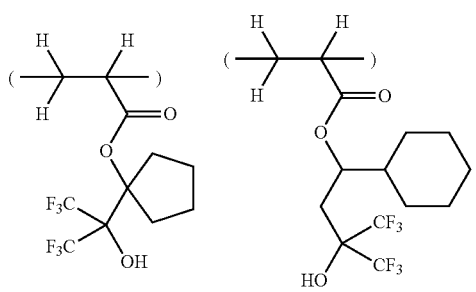
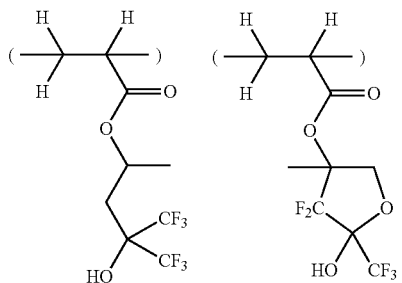
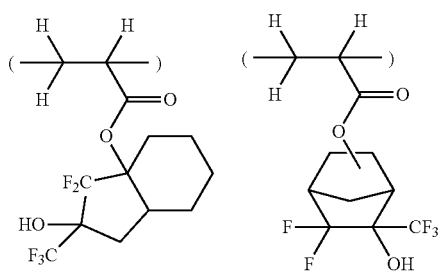
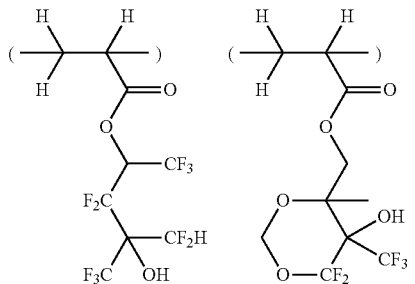
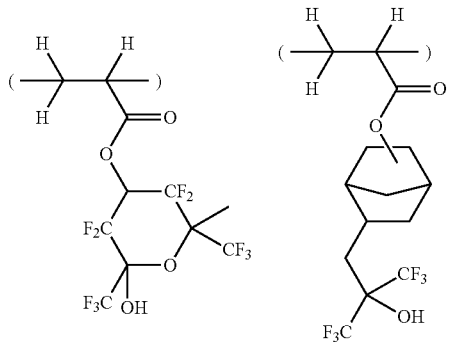

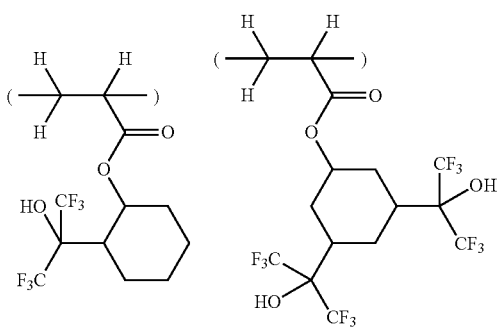

For the surfactant which is insoluble or substantially insoluble in water and soluble in alkaline developer, reference may be made to JP-A 2008-122932, 2010-134012, 2010-107695, 2009-276363, 2009-192784, 2009-191151, 2009-098638, 2011-250105, and 2011-042789.

The polymeric surfactant preferably has a Mw of 1,000 to 50,000, more preferably 2,000 to 20,000 as measured by GPC versus polystyrene standards. A surfactant with a Mw outside the range may be less effective for surface modification and cause development defects. The polymeric surfactant is preferably formulated in an amount of 0.001 to 20 parts, and more preferably 0.01 to 10 parts by weight per 100 parts by weight of the base resin. Reference should also be made to JP-A 2010-215608.

To the resist composition, a compound which is decomposed with an acid to generate another acid, that is, acid amplifier compound may be added. For these compounds, reference should be made to JP-A 2009-269953 and 2010-215608. In the resist composition, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

(G) Organic Acid Derivative and/or Fluorinated Alcohol

Optionally, an organic acid derivative or a compound having a Mw of up to 3,000 which changes its solubility in alkaline developer under the action of an acid, also referred to as dissolution inhibitor, may be added. Reference may be made to JP-A 2009-269953 and 2010-215608.

Process

A further embodiment of the invention is a pattern forming process using the resist composition defined above. A pattern may be formed from the resist composition using any well-known lithography process. The preferred process includes at least the steps of forming a resist film on a substrate, exposing it to high-energy radiation, and developing it in a developer.

The resist composition is applied onto a substrate for integrated circuit fabrication (e.g., Si, $SiO_2$, SiN, SiON, TiN, WSi, BPSG, SOG or organic antireflective coating) or substrate for mask circuit fabrication (e.g., Cr, CrO, CrON or MoSi) by a suitable coating technique such as spin coating. The coating is prebaked on a hot plate at a temperature of 60 to 150° C. for 1 to 10 minutes, preferably 80 to 140° C. for 1 to 5 minutes, to form a resist film of 0.05 to 2.0 μm thick. Through a mask with the desired pattern placed over the resist film, the resist film is exposed to high-energy radiation, typically KrF excimer laser, ArF excimer laser or EUV radiation in a dose of 1 to 200 $mJ/cm^2$, and preferably 10 to 100 $mJ/cm^2$. The exposure may be performed by conventional lithography whereas the immersion lithography of holding a liquid between the mask and the resist film may be employed if desired. In this case, a protective film which is insoluble in water may be applied on the resist film. The resist film is then baked (PEB) on a hot plate at 60 to 150° C. for 1 to 5 minutes, preferably 80 to 140° C. for 1 to 3 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

The water-insoluble protective film which is used in the immersion lithography is to prevent any components from being leached out of the resist film and to improve water slippage at the film surface and is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

The technique enabling the ArF lithography to survive to the 32-nm node is a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, an alkaline aqueous solution, typically an aqueous solution of 0.1 to 5 wt %, more typically 2 to 3 wt % of tetramethylammonium hydroxide (TMAH) is often used as the developer. The negative tone development technique wherein the unexposed region is developed and dissolved in an organic solvent is also applicable.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Examples of the invention are given below by way of illustration and not by way of limitation.

Synthesis Example 1

Synthesis of Carboxylic Acid Sulfonium Salts

Several carboxylic acid sulfonium salts were synthesized according to the following formulation.

Synthesis Example 1-1

Synthesis of 1-(difluoromethoxycarbonylmethyl)-2-methyl-propyl 1-adamantanecarboxylate (Intermediate 1)

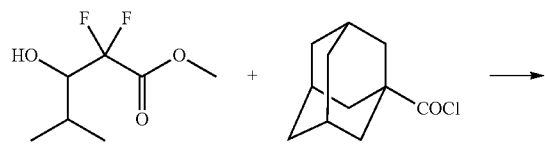

-continued

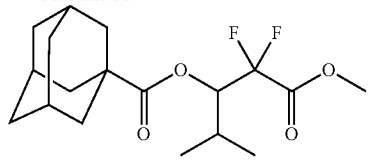

In 100 g of methylene chloride were dissolved 16 g of methyl 2,2-difluoro-3-hydroxy-4-methylpentanoate, synthesized according to the method described in JP-A 2012-097256, and 19 g of 1-adamantanecarbonyl chloride. Under ice cooling, a mixture of 11 g of triethylamine, 1 g of 4-dimethylaminopyridine, and 20 g of methylene chloride were added dropwise to the solution. The reaction solution was aged overnight, after which it was quenched with 5 wt % hydrochloric acid, washed with water, and concentrated. Methyl isobutyl ketone was added to the concentrate, which was concentrated again. On distillation of the concentrate, there was obtained 20 g of the target compound, 1-(difluoromethoxycarbonylmethyl)-2-methyl-propyl 1-adamantanecarboxylate as colorless oily matter (yield 67%).

Synthesis Example 1-2

Synthesis of triphenylsulfonium 3-(adamantane-1-carbonyloxy)-2,2-difluoro-4-methylpentanoate (Q-1)

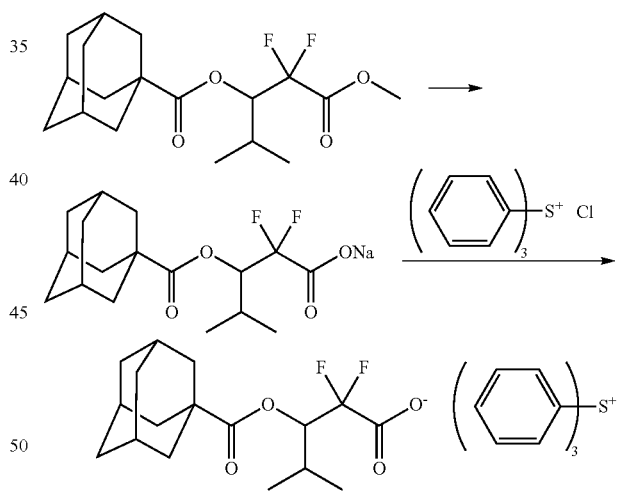

To a mixture of 10 g of 1-(difluoromethoxycarbonylmethyl)-2-methyl-propyl 1-adamantanecarboxylate, prepared in Synthesis Example 1-1, 50 g of 1,4-dioxane, and 20 g of water was added 4.8 g of 25 wt % sodium hydroxide. The reaction solution was stirred for 2 hours, after which it was washed with n-hexane, obtaining an aqueous solution of sodium 3-(adamantane-1-carbonyloxy)-2,2-difluoro-4-methylpentanoate. To this solution, 48 g of an aqueous solution of triphenylsulfonium chloride and 200 g of methylene chloride were added. After stirring for 30 minutes, the organic layer was taken out, washed with water, and concentrated under reduced pressure. Methyl isobutyl ketone was added to the concentrate, which was concentrated again. Diisopropyl ether was added to the concentrate for crystallization. The resulting solid was dried in vacuum, obtaining 15 g of the target compound, triphenylsulfonium 3-(adamantane-1-carbonyloxy)-2,2-difluoro-4-methylpentanoate as white crystals (yield 86%).

Figure 2:
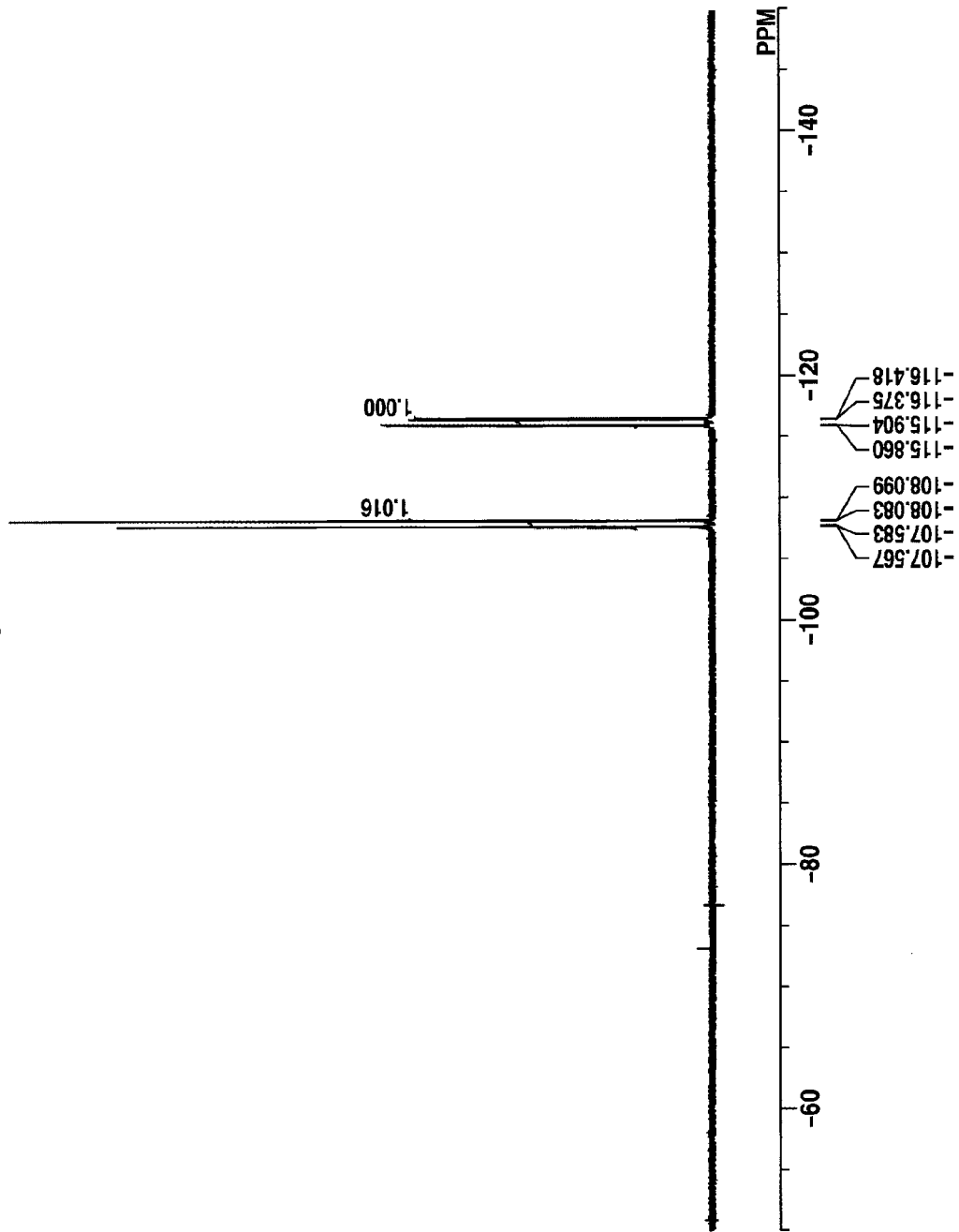
FIG. 2 is a diagram of $^{19}$F-NMR spectrum of the compound obtained in Synthesis Example 1-2.

The target compound was analyzed by spectroscopy. The NMR spectra, $^1$H and $^{19}$F-NMR in DMSO-$d_6$, are shown in FIGS. 1 and 2. In $^1$H-NMR analysis, minute amounts of residual solvents (diisopropyl ether, methyl isobutyl ketone, water) were observed.

Infrared absorption spectrum (IR (D-ATR): cm$^{-1}$)
  3064, 2963, 2906, 2852, 1727, 1662, 1578, 1477, 1453, 1445, 1384, 1344, 1326, 1268, 1236, 1210, 1184, 1103, 1091, 1076, 1028, 997, 843, 797, 763, 746, 730, 685 cm$^{-1}$ Time-of-flight mass spectrometry (TOFMS; MALDI)
  Positive M$^+$ 263 (corresponding to $(C_6H_5)_3S^+$)
  Negative M$^-$ 329 (corresponding to $C_{15}H_{23}O_2$—$CF_2CO_2^-$)

Synthesis Example 1-3

Synthesis of 4-tert-butylphenyldiphenylsulfonium 3-(adamantane-1-carbonyloxy)-2,2-difluoro-4-methylpentanoate (Q-2)

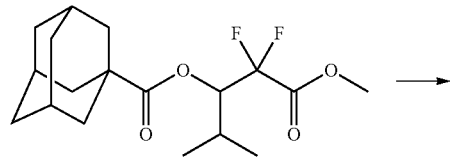

To a mixture of 7 g of 1-(difluoromethoxycarbonylmethyl)-2-methyl-propyl 1-adamantanecarboxylate, prepared in Synthesis Example 1-1, 50 g of 1,4-dioxane, and 20 g of water was added 3.2 g of 25 wt % sodium hydroxide. The reaction solution was stirred for 2 hours, after which it was washed with n-hexane, obtaining an aqueous solution of sodium 3-(adamantane-1-carbonyloxy)-2,2-difluoro-4-methylpentanoate. To this solution, 95 g of an aqueous solution of 4-tert-butylphenyldiphenylsulfonium methylsulfate and 150 g of methylene chloride were added. After stirring for 30 minutes, the organic layer was taken out, washed with water, and concentrated under reduced pressure. Methyl isobutyl ketone was added to the concentrate, which was concentrated again. Diisopropyl ether was added to the concentrate for crystallization. The resulting solid was dried in vacuum, obtaining 10 g of the target compound, 4-tert-butylphenyldiphenylsulfonium 3-(adamantane-1-carbonyloxy)-2,2-difluoro-4-methylpentanoate as white crystals (yield 82%).

Figure 3:
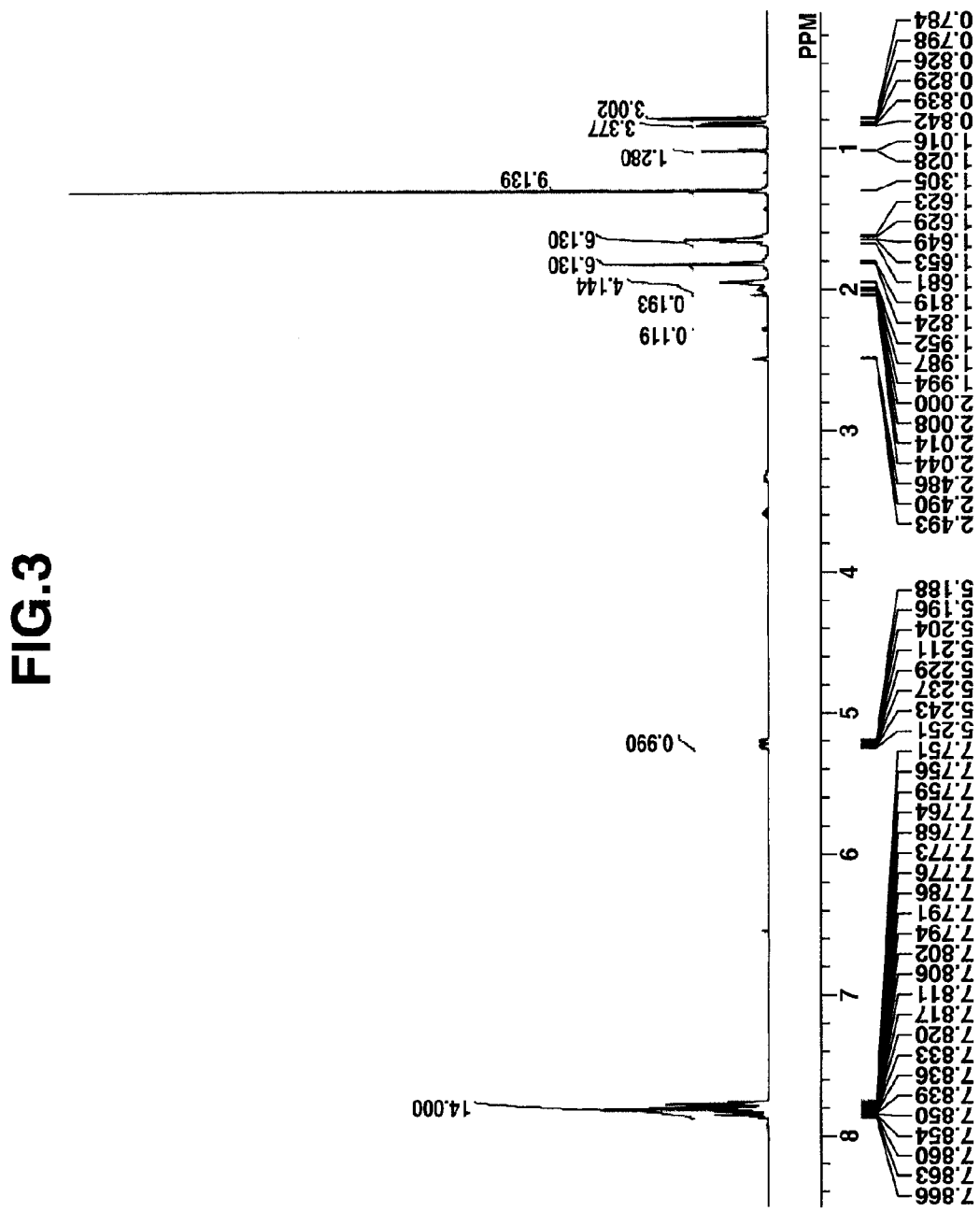
FIGS. 3 and 4 are diagrams of $^1$H- and $^{19}$F-NMR spectra of the compound obtained in Synthesis Example 1-3, respectively.
Figure 4:
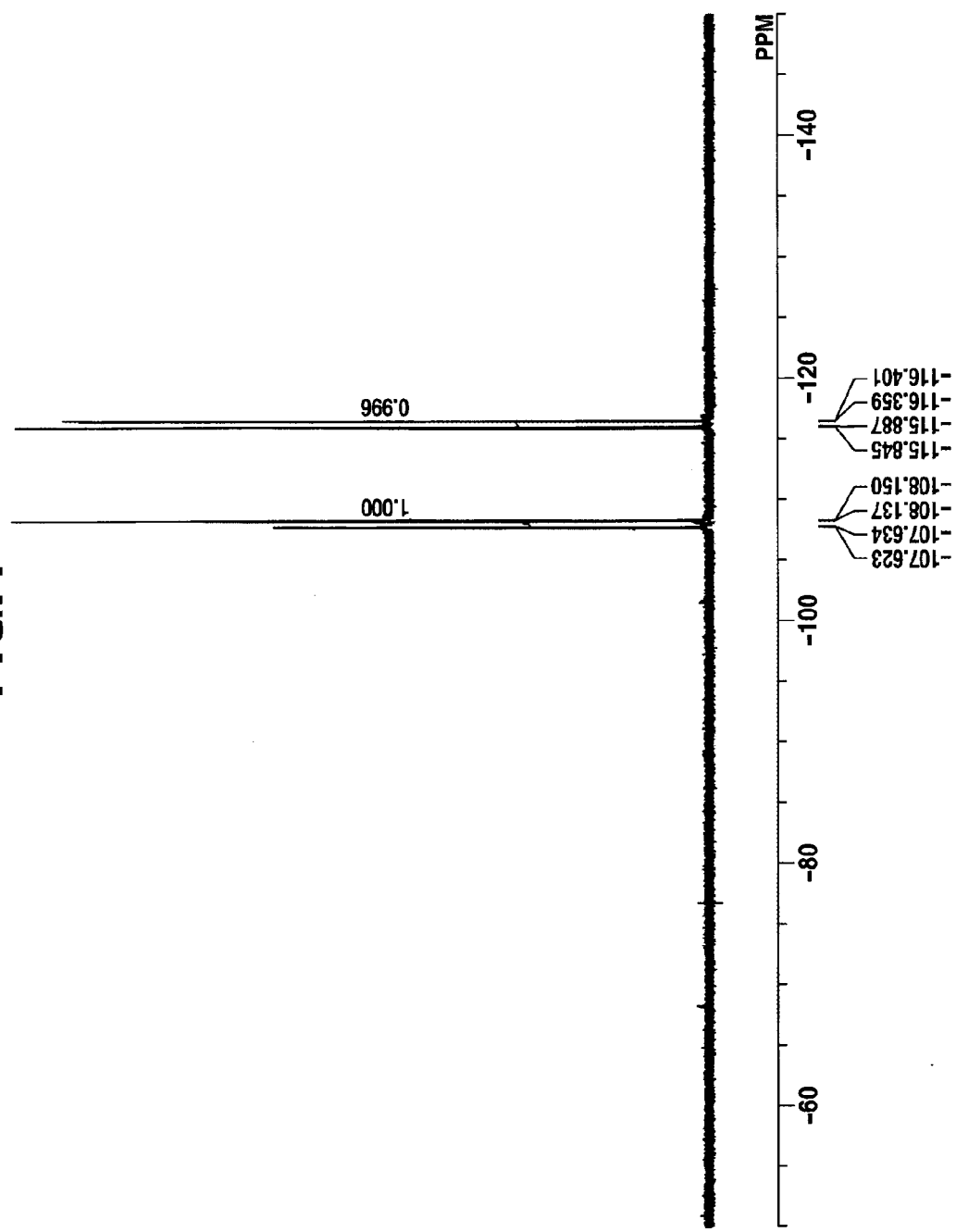

The target compound was analyzed by spectroscopy. The NMR spectra, $^1$H and $^{19}$F-NMR in DMSO-$d_6$, are shown in FIGS. 3 and 4. In $^1$H-NMR analysis, minute amounts of residual solvents (diisopropyl ether, methyl isobutyl ketone, water) were observed.

IR (D-ATR): cm$^{-1}$
  2964, 2904, 2853, 1731, 1660, 1445, 1387, 1231, 1206, 1182, 1087, 1075, 1039, 1000, 799, 765, 739, 730, 689, 682, 560 cm$^{-1}$

TOFMS; MALDI
  Positive M$^+$ 319 (corresponding to $(C_{10}H_{13})(C_6H_5)_2S^+$)
  Negative M$^-$ 329 (corresponding to $C_{15}H_{23}O_2$—$CF_2CO_2^-$)

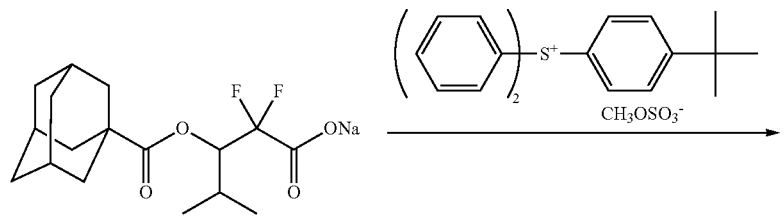

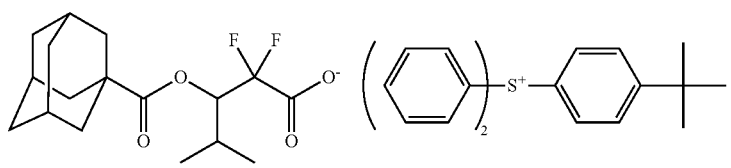

Synthesis Example 1-4

Synthesis of ethyl 2,2-difluoro-3-hydroxy-3-phenylpropionate (Intermediate 2)

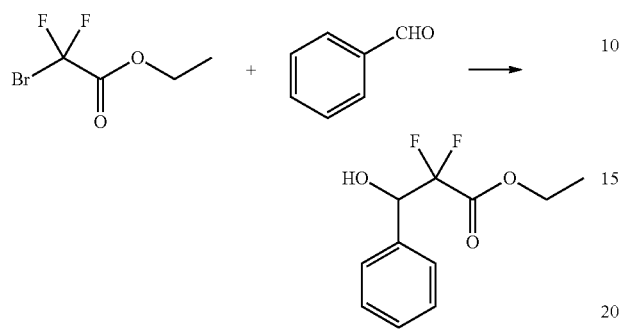

A mixture of 48 g of ethyl bromodifluoroacetate, 4.5 g of dibromoethane and 50 g of tetrahydrofuran was added dropwise to a mixture of 15 g of zinc, 21 g of benzaldehyde, 60 mL of trimethyl borate, and 50 g of tetrahydrofuran at a temperature of 60° C., followed by stirring for 10 hours at 90° C. Thereafter, 100 g of 10 wt % hydrochloric acid was added to quench the reaction. By filtration, the insoluble was removed, and the filtrate was washed with saturated sodium chloride water. The reaction solution after washing was concentrated under reduced pressure. The concentrate was purified by distillation, obtaining 28 g of the target compound, ethyl 2,2-difluoro-3-hydroxy-3-phenylpropionate as colorless oily matter (yield 60%).

Synthesis Example 1-5

Synthesis of 2-ethoxycarbonyl-2,2-difluoro-1-phenylethyl 1-adamantanecarboxylate (Intermediate 3)

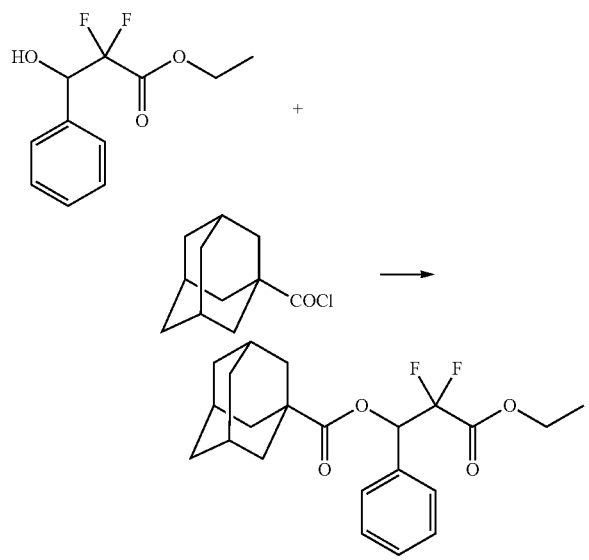

In 60 g of methylene chloride were dissolved 9 g of ethyl 2,2-difluoro-3-hydroxy-3-phenylpropionate, prepared in Synthesis Example 1-4, and 9.5 g of 1-adamantanecarbonyl chloride. Under ice cooling, a mixture of 6 g of triethylamine, 0.5 g of 4-dimethylaminopyridine and 20 g of methylene chloride was added dropwise to the solution. The reaction solution was aged overnight, after which it was quenched with 5 wt % hydrochloric acid, washed with water, and concentrated. Methyl isobutyl ketone was added to the concentrate, which was concentrated again. There was obtained 15 g of the target compound, 2-ethoxycarbonyl-2,2-difluoro-1-phenylethyl 1-adamantanecarboxylate as colorless oily matter (yield 68%).

Synthesis Example 1-6

Synthesis of triphenylsulfonium 3-(adamantane-1-carbonyloxy)-2,2-difluoro-3-phenylpropionate (Q-3)

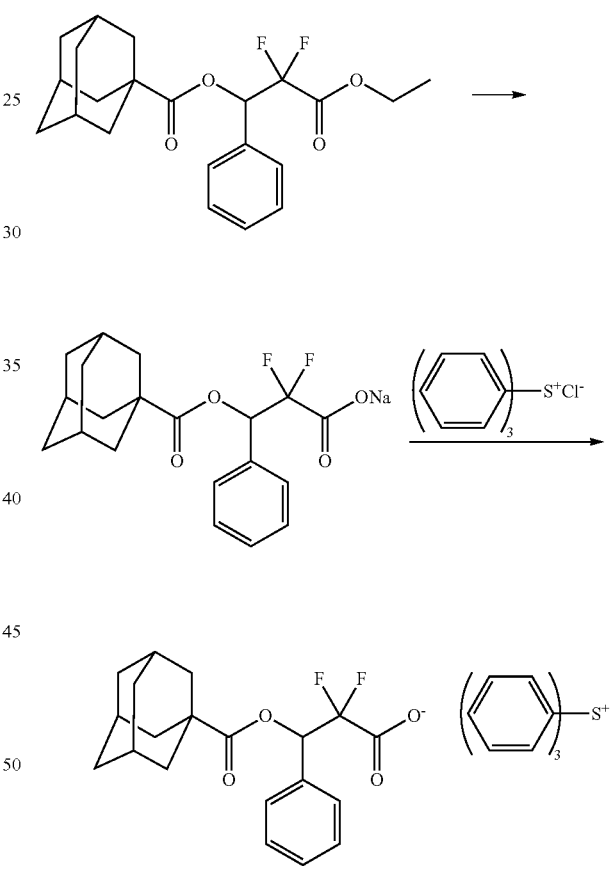

A mixture of 6.6 g of 2-ethoxycarbonyl-2,2-difluoro-1-phenylethyl 1-adamantanecarboxylate, prepared in Synthesis Example 1-5, 20 g of 1,4-dioxane, and 2.5 g of 25 wt % sodium hydroxide was stirred for 2 hours. Water, 30 g, was added to the reaction solution. The reaction solution was washed with n-hexane, obtaining an aqueous solution of sodium 3-(adamantane-1-carbonyloxy)-2,2-difluoro-3-phenylpropionate. To this solution, 32 g of an aqueous solution of triphenylsulfonium chloride and 100 g of methylene chloride were added. After stirring for 30 minutes, the organic layer was taken out, washed with water, and concentrated under reduced pressure. Methyl isobutyl ketone was added to the concentrate, which was concentrated again. Diisopropyl ether was added to the concentrate for crystallization. The resulting solid was dried in vacuum, obtaining 5.5 g of the target compound, triphenylsulfonium 3-(adamantane-1-carbonyloxy)-2,2-difluoro-3-phenylpropionate as white crystals (yield 58%).

Figure 5:
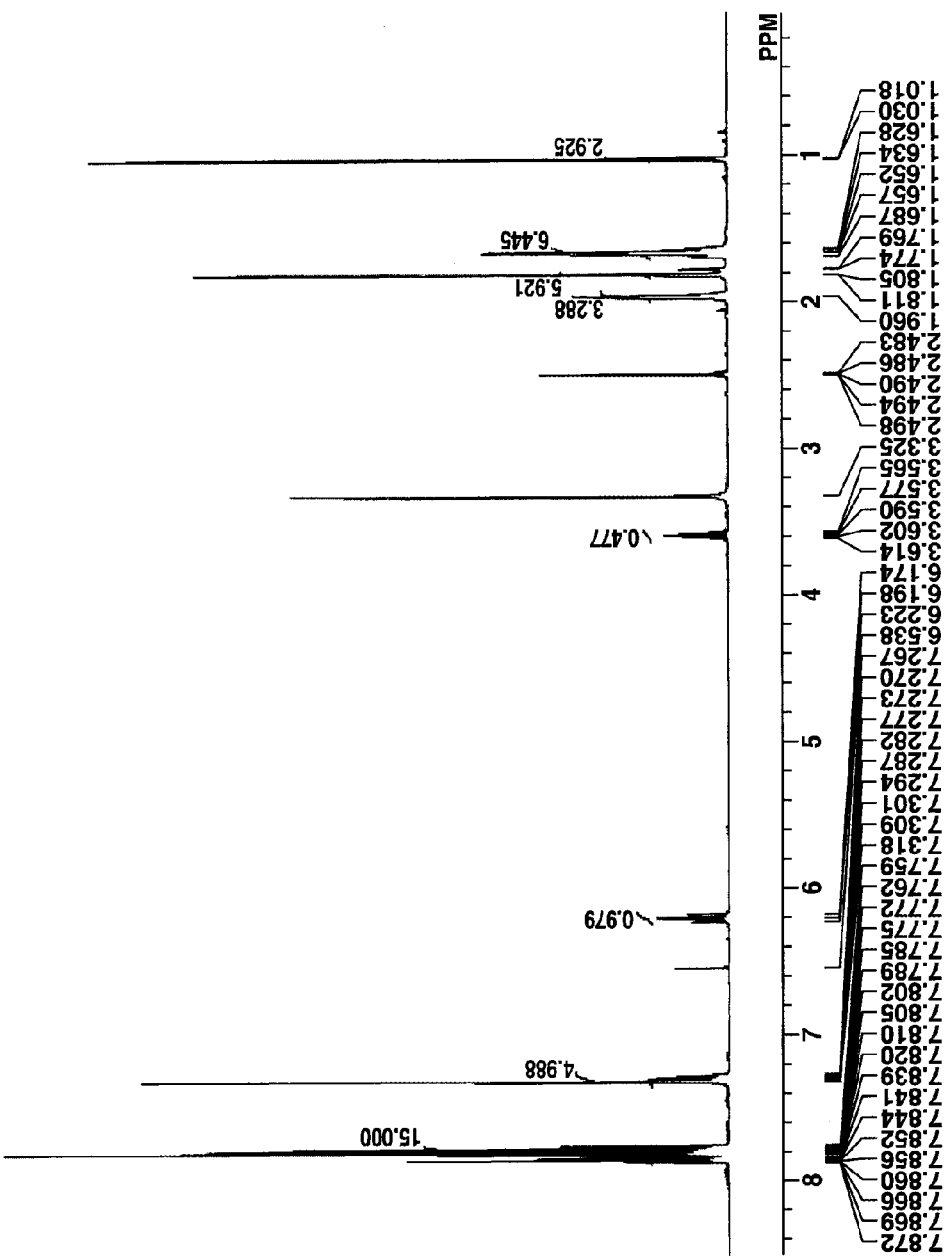
FIGS. 5 and 6 are diagrams of $^1$H- and $^{19}$F-NMR spectra of the compound obtained in Synthesis Example 1-6, respectively.
Figure 6:
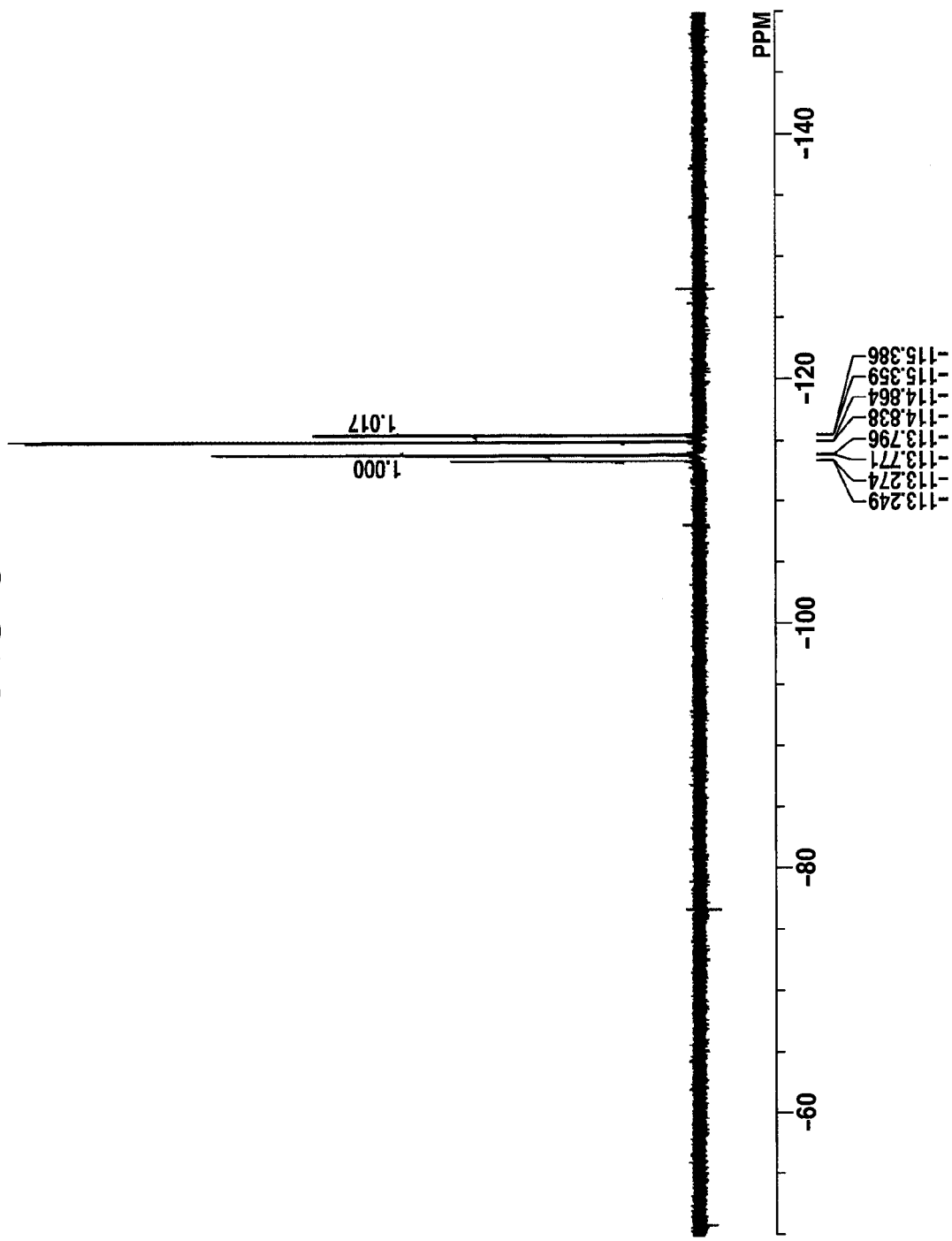

The target compound was analyzed by spectroscopy. The NMR spectra, $^1$H and $^{19}$F-NMR in DMSO-$d_6$, are shown in FIGS. 5 and 6. In $^1$H-NMR analysis, minute amounts of residual solvents (diisopropyl ether, water) were observed.
IR (D-ATR): cm$^{-1}$
  2905, 2851, 1729, 1659, 1476, 1447, 1379, 1326, 1267, 1228, 1184, 1111, 1073, 1049, 996, 800, 751, 723, 684 cm$^{-1}$
TOFMS; MALDI
  Positive M$^+$ 263 (corresponding to $(C_6H_5)_3S^+$)
  Negative M$^-$ 363 (corresponding to $C_{18}H_{21}O_2$—$CF_2CO_2^-$)

Synthesis Example 1-7

Synthesis of 4-tert-butylphenyldiphenylsulfonium 3-(adamantane-1-carbonyloxy)-2,2-difluoro-3-phenylpropionate (Q-4)

A mixture of 6.6 g of 2-ethoxycarbonyl-2,2-difluoro-1-phenylethyl 1-adamantanecarboxylate, prepared in Synthesis Example 1-5, 20 g of 1,4-dioxane, and 2.5 g of 25 wt % sodium hydroxide was stirred for 2 hours. Water, 30 g, was added to the reaction solution, which was washed with n-hexane, obtaining an aqueous solution of sodium 3-(adamantane-1-carbonyloxy)-2,2-difluoro-3-phenylpropionate. To this solution, 95 g of an aqueous solution of 4-tert-butylphenyldiphenylsulfonium methylsulfate and 100 g of methylene chloride were added. After stirring for 30 minutes, the organic layer was taken out, washed with water, and concentrated under reduced pressure. Methyl isobutyl ketone was added to the concentrate, which was concentrated again. Diisopropyl ether was added to the concentrate for crystallization. The resulting solid was dried in vacuum, obtaining 5.4 g of the target compound, 4-tert-butylphenyldiphenylsulfonium 3-(adamantane-1-carbonyloxy)-2,2-difluoro-3-phenylpropionate as white crystals (yield 52%).

Figure 7:
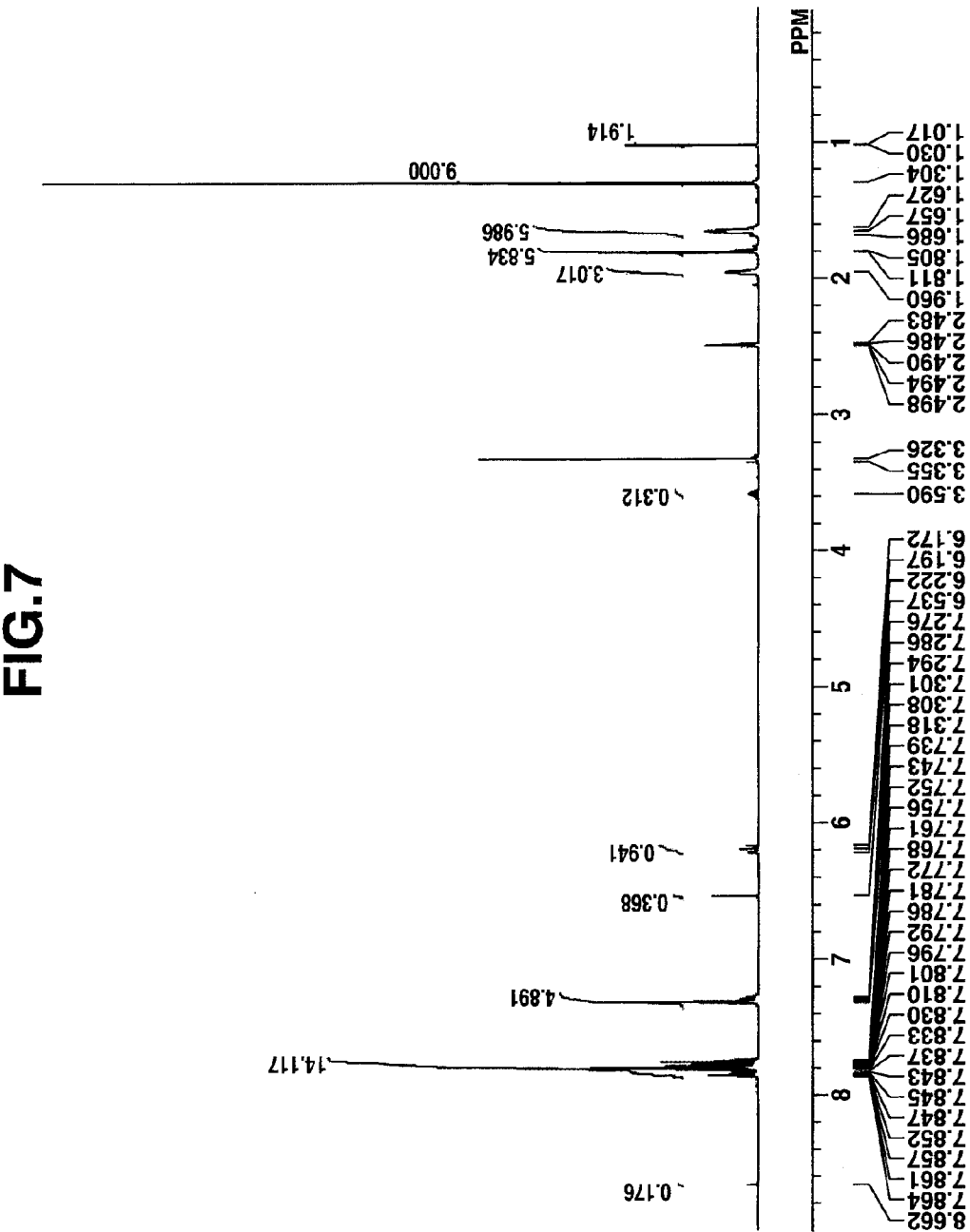
FIGS. 7 and 8 are diagrams of $^1$H- and $^{19}$F-NMR spectra of the compound obtained in Synthesis Example 1-7, respectively.
Figure 8:
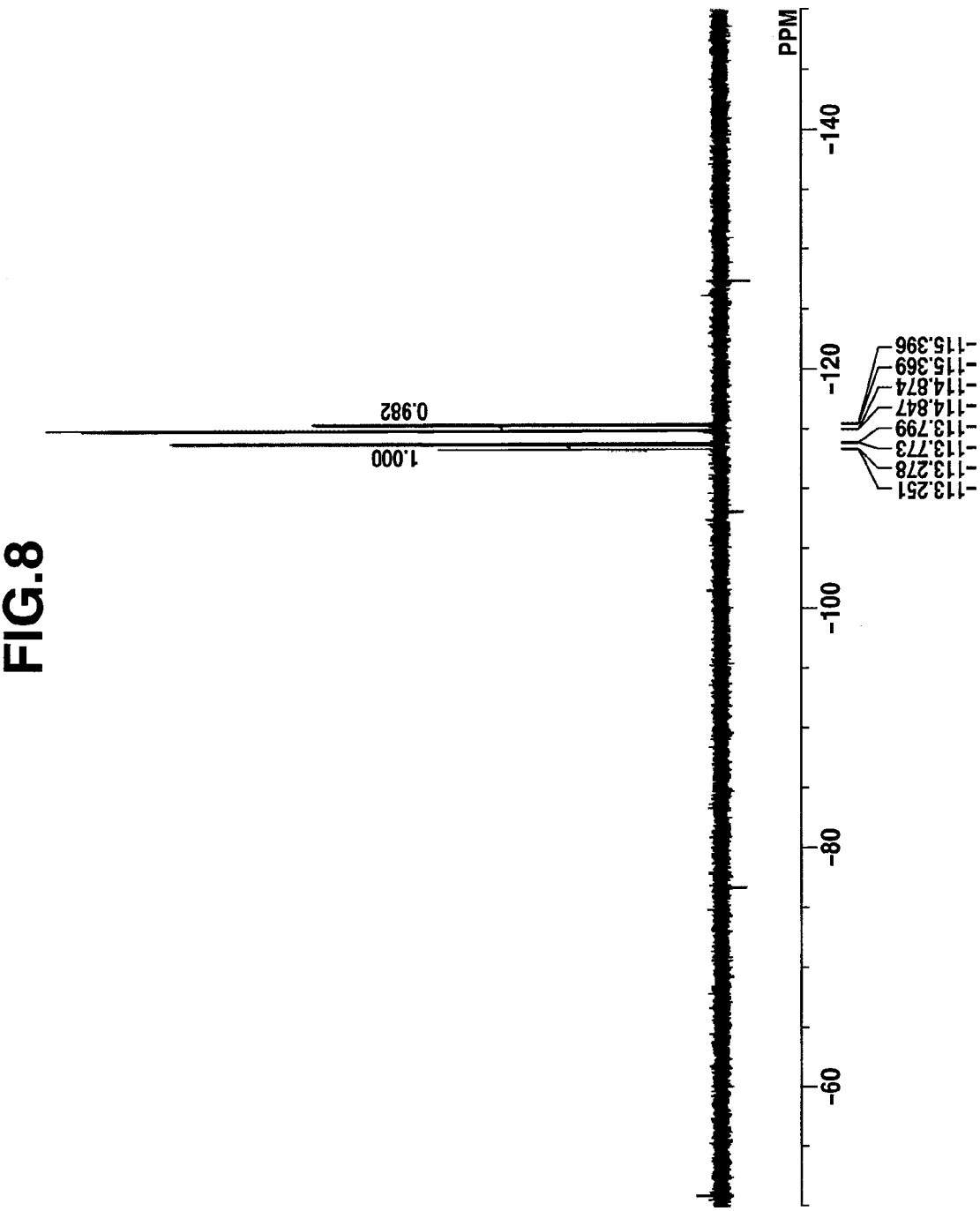

The target compound was analyzed by spectroscopy. The NMR spectra, $^1$H and $^{19}$F-NMR in DMSO-$d_6$, are shown in FIGS. 7 and 8. In $^1$H-NMR analysis, minute amounts of residual solvents (diisopropyl ether, water) were observed.
IR (D-ATR): cm$^{-1}$

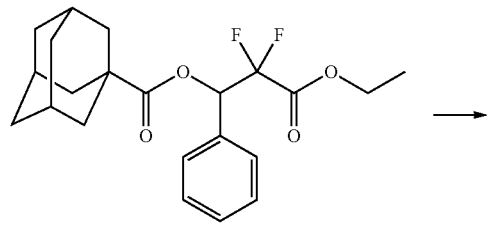

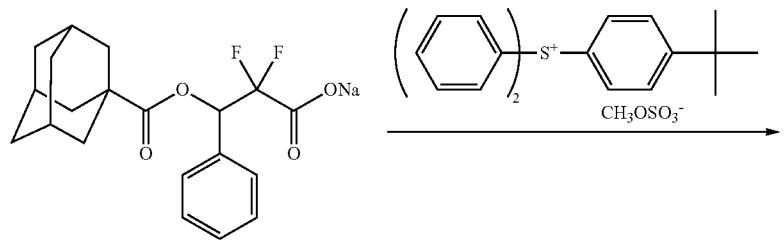

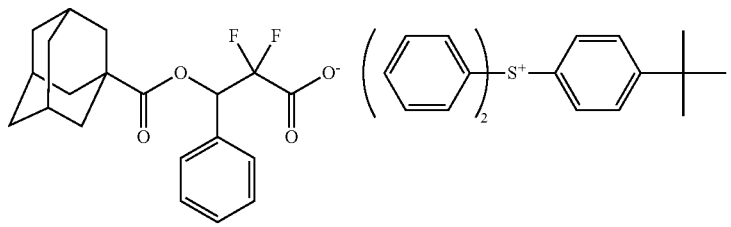

2904, 2851, 1730, 1660, 1476, 1446, 1378, 1227, 1183, 1111, 1073, 1049, 997, 799, 751, 723, 684 cm$^{-1}$

TOFMS; MALDI
Positive M$^+$ 319 (corresponding to (C$_{10}$H$_{13}$) (C$_6$H$_5$)$_2$S$^+$)
Negative M$^-$ 363 (corresponding to C$_{18}$H$_{21}$O$_2$—CF$_2$CO$_2^-$)

Synthesis Example 1-8

Synthesis of ethyl difluoro-(2-hydroxyadamantan-2-yl)acetate (Intermediate 4)

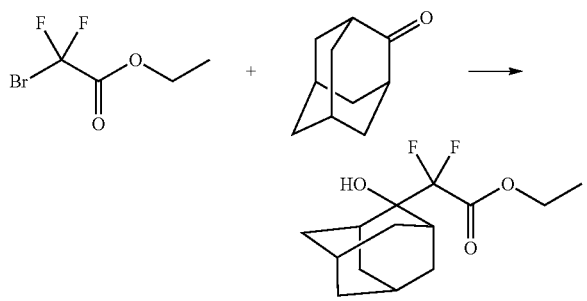

A mixture of 24 g of ethyl bromodifluoroacetate, 2.2 g of dibromoethane and 25 g of tetrahydrofuran was added dropwise to a mixture of 7.8 g of zinc, 15 g of 2-adamantanone, 30 mL of trimethyl borate, and 25 g of tetrahydrofuran at a temperature of 50° C., followed by stirring for 10 hours at 80° C. Thereafter, 50 g of 5 wt % hydrochloric acid was added to quench the reaction. Ethyl acetate, 20 g, was added to the reaction solution, from which the organic layer was extracted. The organic layer was washed with saturated sodium chloride water and then with water. The reaction solution after washing was concentrated under reduced pressure. Methyl isobutyl ketone was added to the concentrate, the resulting solution was concentrated under reduced pressure again, and n-hexane was added to the concentrate for crystallization. The resulting solid was dried in vacuum, obtaining 15 g of the target compound, ethyl difluoro-(2-hydroxyadamantan-2-yl)acetate as white crystals (yield 58%).

Synthesis Example 1-9

Synthesis of triphenylsulfonium difluoro-(2-hydroxyadamantan-2-yl)acetate (Q-5)

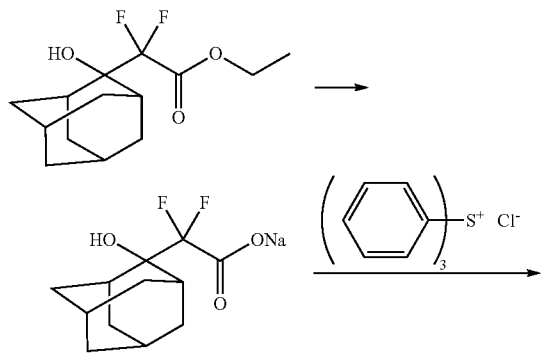

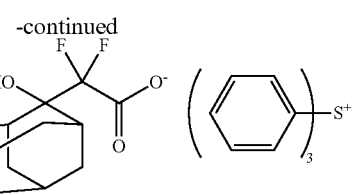

A mixture of 3.9 g of ethyl difluoro-(2-hydroxyadamantan-2-yl)acetate, prepared in Synthesis Example 1-8, 20 g of 1,4-dioxane, and 4.8 g of 25 wt % sodium hydroxide was stirred for 2 hours. To the reaction solution, 1.5 g of 35 wt % hydrochloric acid was added, and then 24 g of an aqueous solution of triphenylsulfonium chloride and 100 g of methylene chloride were added. After stirring for 30 minutes, the organic layer was taken out, washed with water, and concentrated under reduced pressure. Methyl isobutyl ketone was added to the concentrate, which was concentrated again. Diisopropyl ether was added to the concentrate for crystallization. The resulting solid was dried in vacuum, obtaining 4.7 g of the target compound, triphenylsulfonium difluoro-(2-hydroxyadamantan-2-yl)acetate as white crystals (yield 63%).

Figure 9:
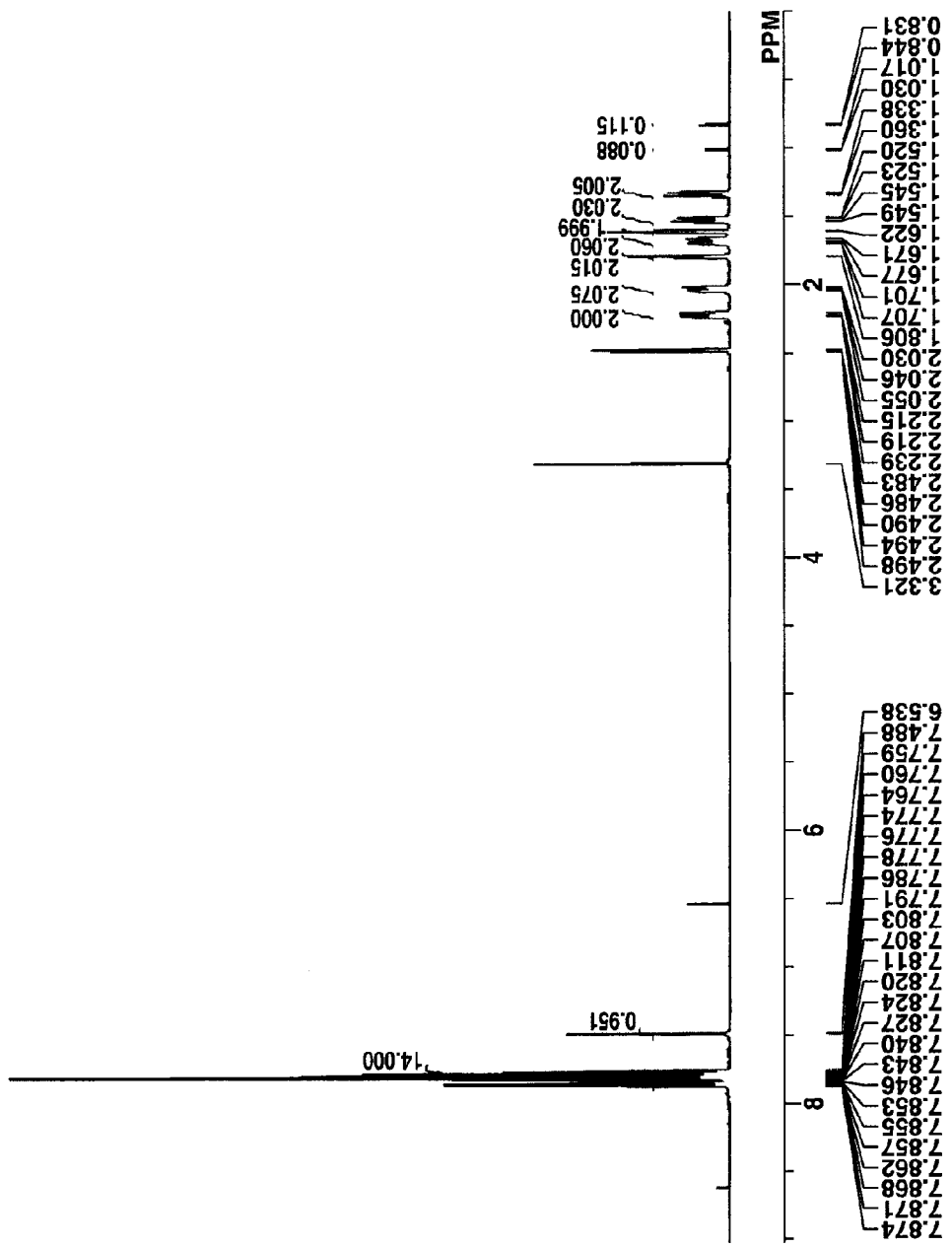
FIGS. 9 and 10 are diagrams of $^1$H- and $^{19}$F-NMR spectra of the compound obtained in Synthesis Example 1-9, respectively.
Figure 10:
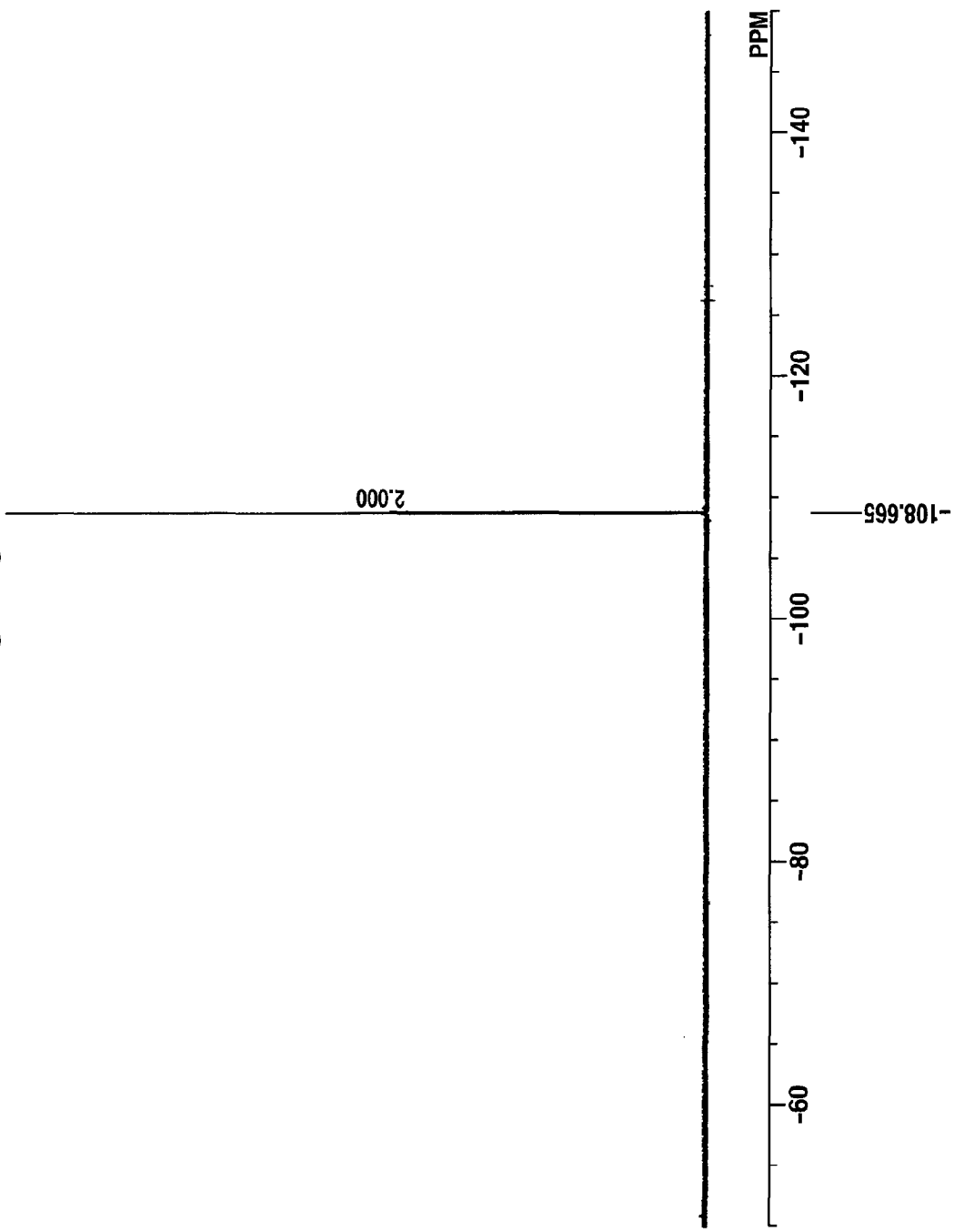

The target compound was analyzed by spectroscopy. The NMR spectra, $^1$H and $^{19}$F-NMR in DMSO-d$_6$, are shown in FIGS. 9 and 10. In $^1$H-NMR analysis, minute amounts of residual solvents (diisopropyl ether, methyl isobutyl ketone, water) were observed.

IR (D-ATR): cm$^{-1}$
3057, 2911, 2857, 1644, 1475, 1446, 1391, 1186, 1105, 1089, 1071, 1047, 1037, 1020, 994, 963, 800, 746, 681 cm$^{-1}$

TOFMS; MALDI
Positive M$^+$ 263 (corresponding to (C$_6$H$_5$)$_3$S$^+$)
Negative M$^-$ 245 (corresponding to C$_{10}$H$_{15}$O—CF$_2$CO$_2^-$)

Synthesis Example 1-10

Synthesis of 4-fluorophenyldiphenylsulfonium difluoro-(2-hydroxyadamantan-2-yl)acetate (Q-6)

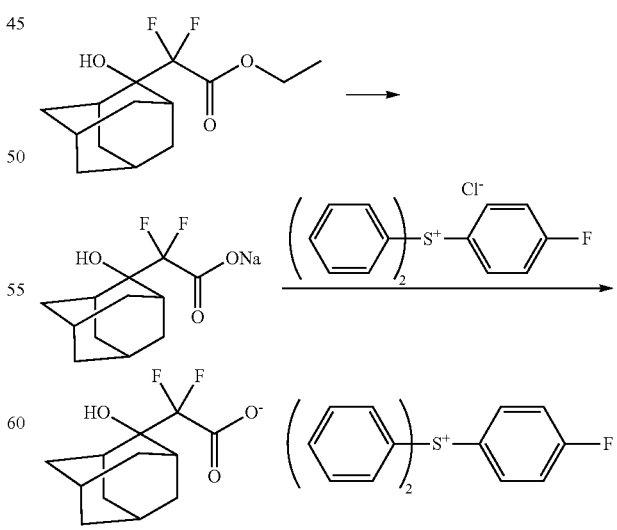

A mixture of 2.6 g of ethyl difluoro-(2-hydroxyadamantan-2-yl)acetate, prepared in Synthesis Example 1-8, 30 g of 1,4-dioxane, 4.0 g of 25 wt % sodium hydroxide, and 10 g of water was stirred for 2 hours. To the reaction solution, 1.0 g of 35 wt % hydrochloric acid was added, and then 66 g of an aqueous solution of 4-fluorophenyldiphenylsulfonium chloride and 100 g of methylene chloride were added. After stirring for 30 minutes, the organic layer was taken out, washed with water, and concentrated under reduced pressure. Methyl isobutyl ketone was added to the concentrate, which was concentrated again. Diisopropyl ether was added to the concentrate. The supernatant was removed, leaving 2.4 g of the target compound, 4-fluorophenyldiphenylsulfonium difluoro-(2-hydroxyadamantan-2-yl)acetate as vitreous solids (yield 45%).

Figure 11:
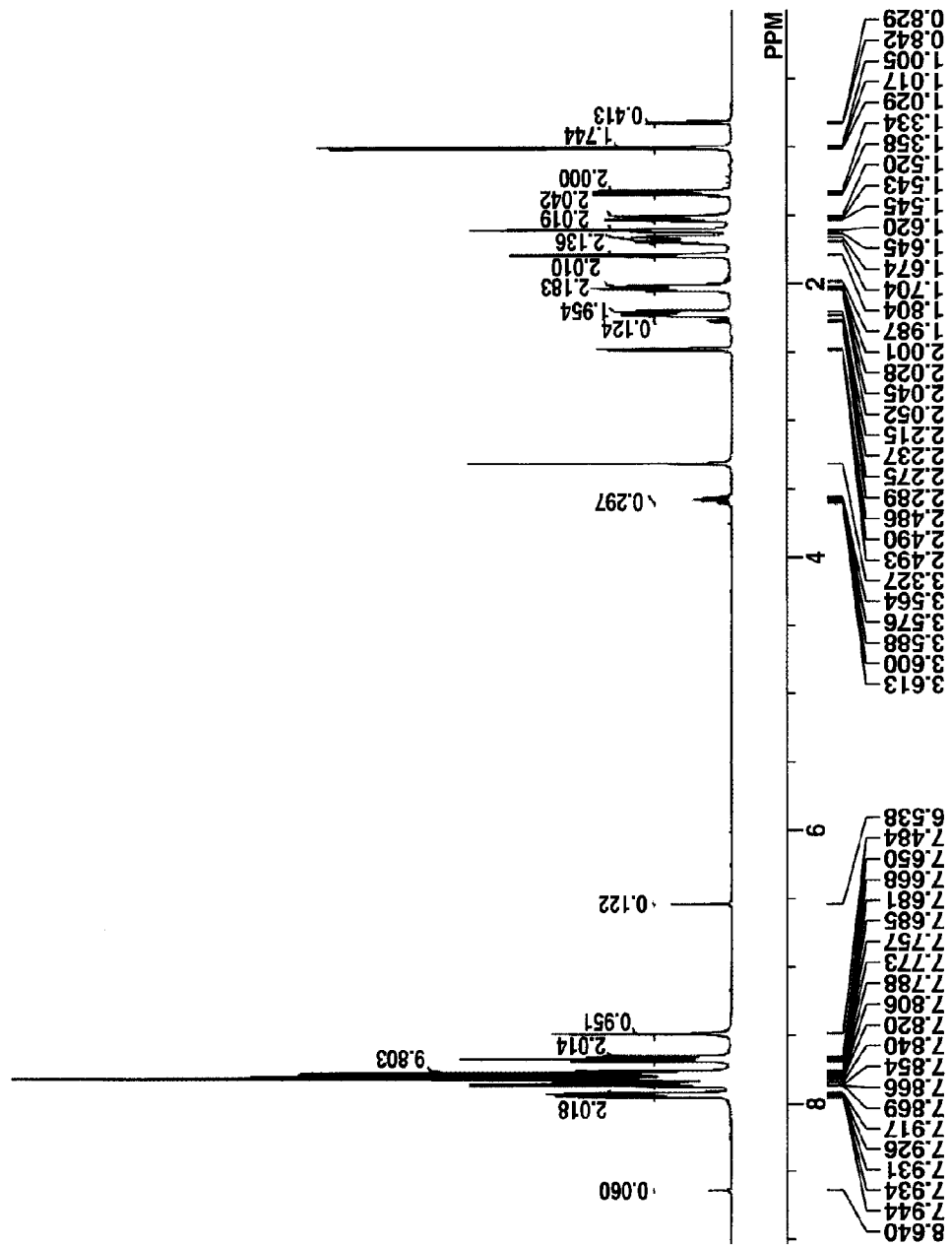
FIGS. 11 and 12 are diagrams of $^1$H- and $^{19}$F-NMR spectra of the compound obtained in Synthesis Example 1-10, respectively.
Figure 12:
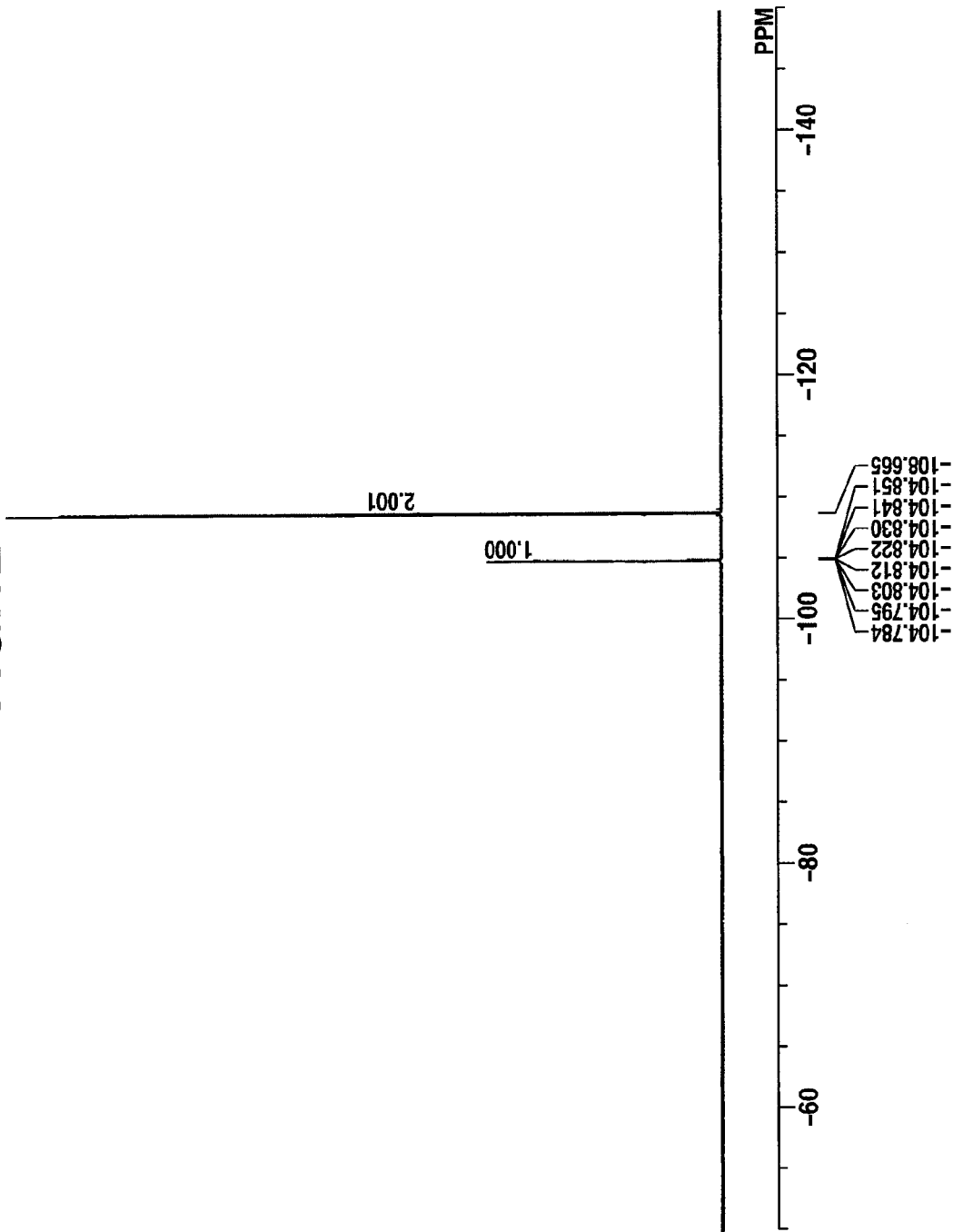

The target compound was analyzed by spectroscopy. The NMR spectra, $^1$H and $^{19}$F-NMR in DMSO-$d_6$, are shown in FIGS. 11 and 12. In $^1$H-NMR analysis, minute amounts of residual solvents (diisopropyl ether, methyl isobutyl ketone, water) were observed.

IR (D-ATR): cm$^{-1}$ 3366, 3094, 3058, 2903, 2849, 1651, 1586, 1492, 1476, 1447, 1404, 1241, 1195, 1163, 1099, 1074, 1045, 999, 839, 813, 797, 750, 708, 684 cm$^{-1}$

TOFMS; MALDI

Positive M$^+$ 281 (corresponding to $(C_6H_4F)(C_6H_5)_2S^+$)

Negative M$^-$ 245 (corresponding to $C_{10}H_{15}O-CF_2CO_2^-$)

Synthesis Example 1-11

Synthesis of ethyl 3-(1-adamantyl)-2,2-difluoro-3-hydroxypropionate (Intermediate 5)

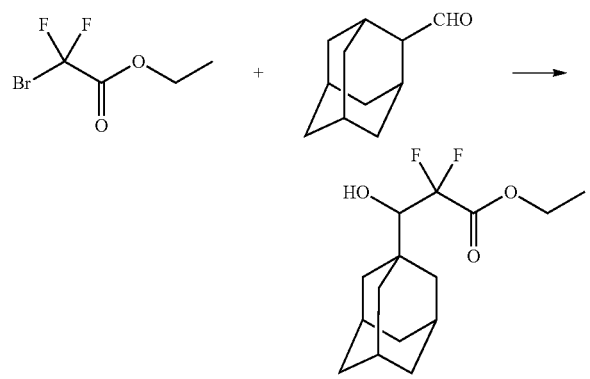

A mixture of 40 g of ethyl bromodifluoroacetate, 3.7 g of dibromoethane and 50 g of tetrahydrofuran was added dropwise to a mixture of 13 g of zinc, 29 g of 2-adamantanecarbaldehyde, 60 mL of trimethyl borate, and 50 g of tetrahydrofuran at a temperature of 50° C., followed by stirring for 10 hours at 60° C. Thereafter, 100 g of 5 wt % hydrochloric acid was added to quench the reaction. Ethyl acetate, 200 g, was added to the reaction solution, from which the organic layer was extracted. The organic layer was washed with saturated sodium chloride water and then with water. The reaction solution after washing was concentrated under reduced pressure, obtaining 23 g of the target compound, ethyl 3-(1-adamantyl)-2,2-difluoro-3-hydroxypropionate as oily matter (yield 54%).

Synthesis Example 1-12

Synthesis of 4-fluorophenyldiphenylsulfonium 3-(1-adamantyl)-2,2-difluoro-3-hydroxypropionate (Q-7)

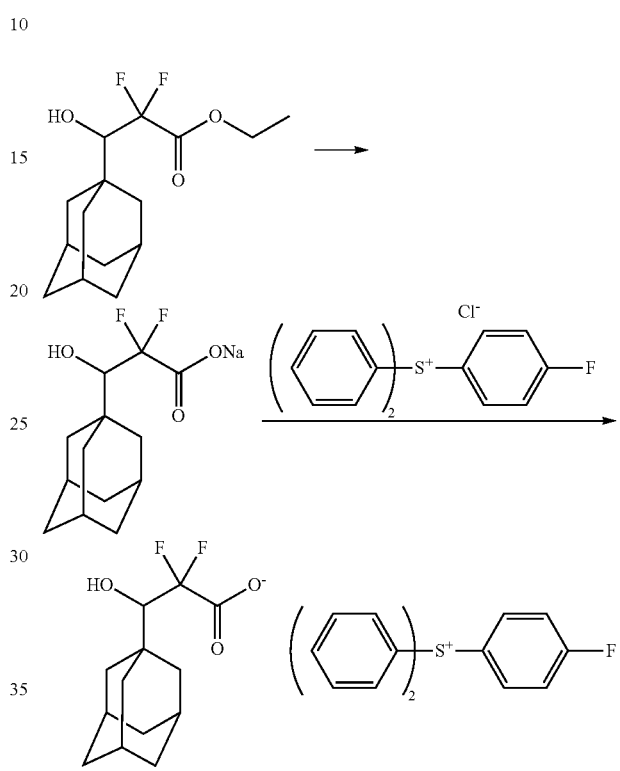

A mixture of 6.6 g of ethyl 3-(1-adamantyl)-2,2-difluoro-3-hydroxypropionate, prepared in Synthesis Example 1-11, 50 g of 1,4-dioxane, 8.0 g of 25 wt % sodium hydroxide, and 20 g of water was stirred for 2 hours. To the reaction solution, 2.0 g of 35 wt % hydrochloric acid was added, and then 53 g of an aqueous solution of 4-fluorophenyldiphenylsulfonium chloride and 100 g of methylene chloride were added. After stirring for 30 minutes, the organic layer was taken out, washed with water, and concentrated under reduced pressure. Methyl isobutyl ketone was added to the concentrate, which was concentrated again. Diisopropyl ether was added to the concentrate for crystallization. The resulting solid was dried in vacuum, obtaining 6.2 g of the target compound, 4-fluorophenyldiphenylsulfonium 3-(1-adamantyl)-2,2-difluoro-3-hydroxypropionate as white crystals (yield 57%).

Figure 13:
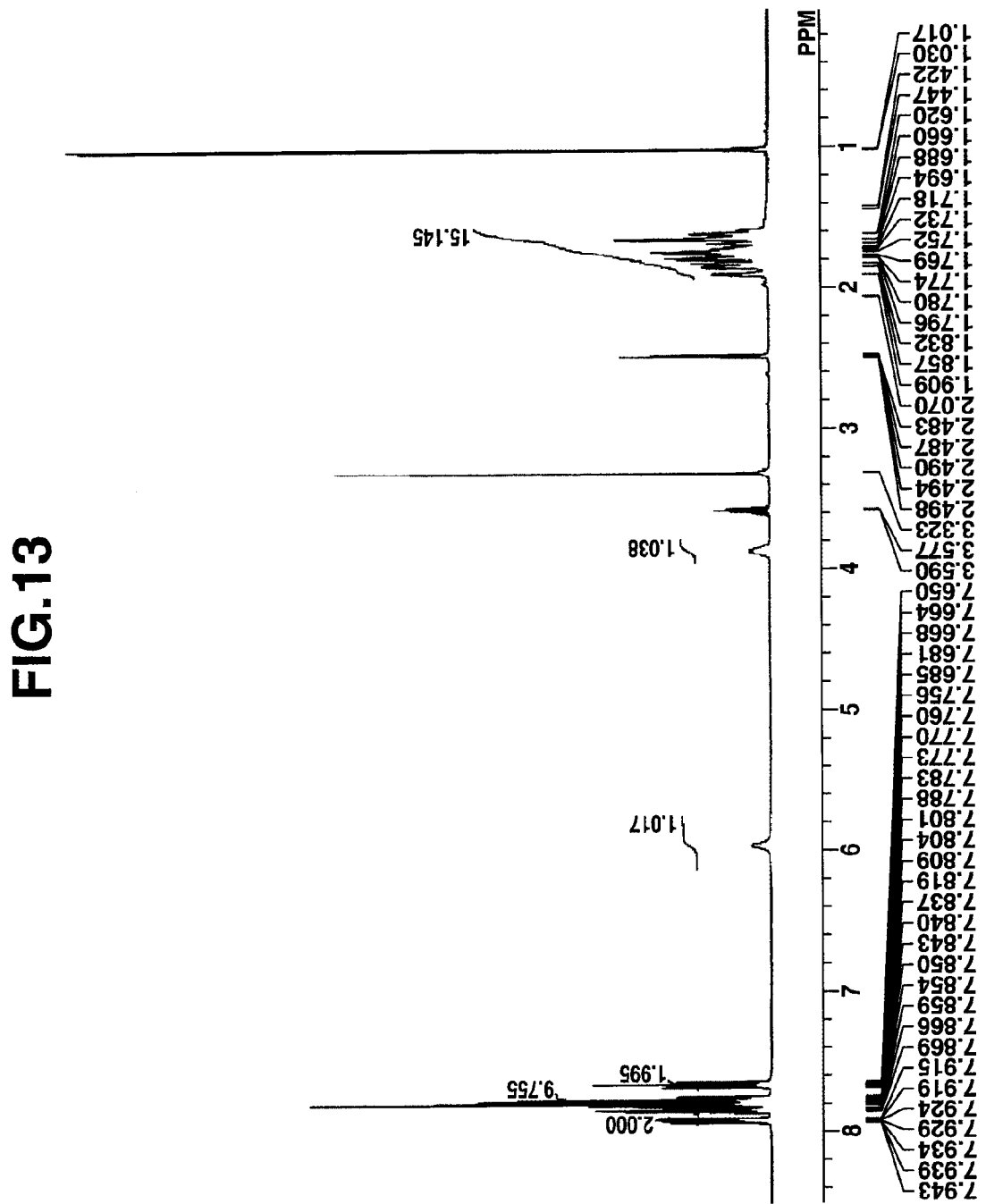
FIGS. 13 and 14 are diagrams of $^1$H- and $^{19}$F-NMR spectra of the compound obtained in Synthesis Example 1-12, respectively.
Figure 14:
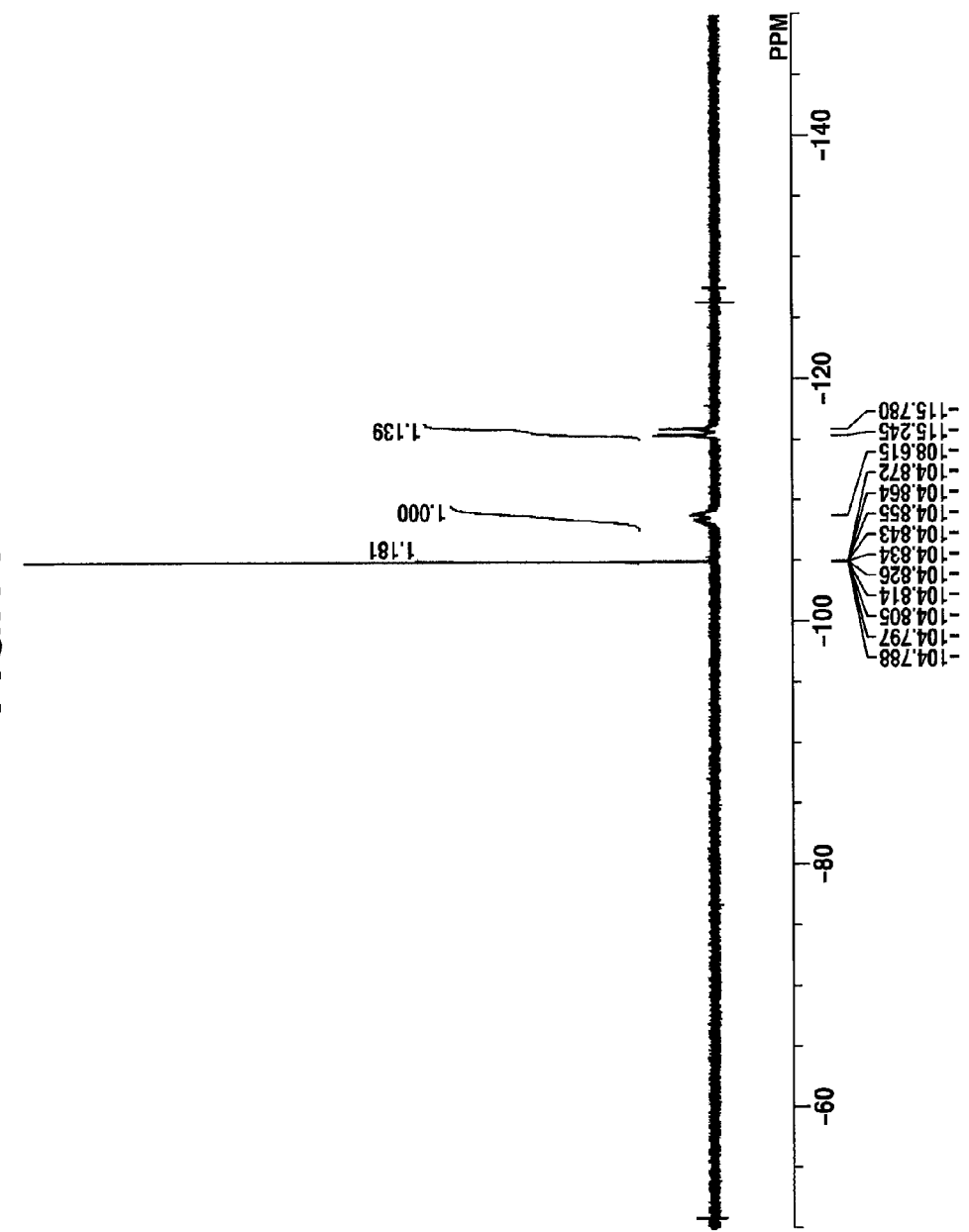

The target compound was analyzed by spectroscopy. The NMR spectra, $^1$H and $^{19}$F-NMR in DMSO-$d_6$, are shown in FIGS. 13 and 14. In $^1$H-NMR analysis, minute amounts of residual solvents (diisopropyl ether, water) were observed.

TOFMS; MALDI

Positive M$^+$ 281 (corresponding to $(C_6H_4F)(C_6H_5)_2S^+$)

Negative M$^-$ 259 (corresponding to $C_{11}H_{17}O-CF_2CO_2^-$)

Synthesis Example 2

Polymers for use in resist compositions were synthesized according to the following formulation. Notably, Mw and Mn are weight and number average molecular weights, respectively, as measured by GPC versus polystyrene standards, and Mw/Mn is a polydispersity index.

Synthesis Example 2-2

Synthesis of Polymer P-1

Under a nitrogen blanket, a flask was charged with 3.9 g of 3-hydroxy-1-adamantyl methacrylate, 18.0 g of 3-ethyl-3-exo-tetracyclo[4.4.0.1$^{2,5}$.1$^{7,10}$]dodecyl methacrylate, 18.3 g of 4,8-dioxatricyclo[4.2.1.0$^{3,7}$]nonan-5-on-2-yl methacrylate, 0.38 g of dimethyl 2,2'-azobis(2-methylpropionate) (V-601 by Wako Pure Chemical Industries, Ltd.), 0.48 g of 2-mercaptoethanol, 24 g of PGMEA, and 31 g of γ-butyrolactone to form a monomer/initiator solution. Another flask under a nitrogen blanket was charged with 8.0 g of propylene glycol methyl ether acetate (PMA) and 10.5 g of γ-butyrolactone and heated at 80° C. with stirring, after which the monomer/initiator solution was added dropwise over 4 hours. After the completion of dropwise addition, the polymerization solution was continuously stirred for 2 hours while keeping the temperature of 80° C. It was then cooled to room temperature. With vigorous stirring, the polymerization solution was added dropwise to 640 g of methanol containing 10 wt % water where a copolymer precipitated. The copolymer was collected by filtration, washed twice with 240 g of methanol, and vacuum dried at 50° C. for 20 hours, obtaining 35.3 g of the copolymer in white powder form (yield 88%). The copolymer (designated Polymer P-1) was analyzed for composition. On GPC analysis, the copolymer had a Mw of 6,520 and a Mw/Mn of 1.86.

(P-1)
(a=0.40, b=0.50, C=0.10)

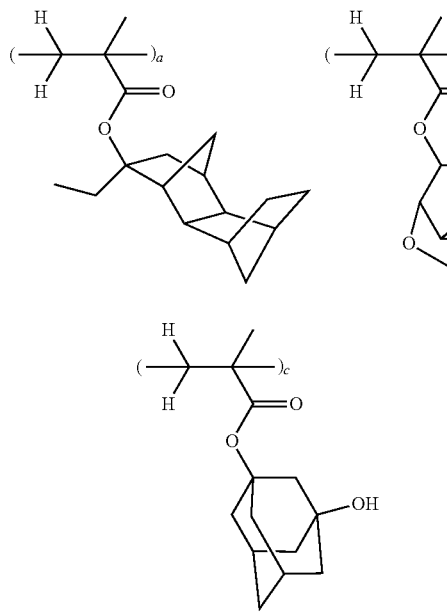

Synthesis Examples 2-2 to 2-14

Synthesis of Polymers P-2 to P-14

Polymers P-2 to P-14 were prepared by the same procedure as in Synthesis Example 2-1 except that the type and amount of monomers used were changed.

The compositional proportions of the polymers or resins thus prepared are shown in Table 1 where values are molar ratios of monomer units incorporated. The structures of units in Table 1 are shown in Tables 2 to 4.

TABLE 1

| Resin | Unit 1 | (ratio) | Unit 2 | (ratio) | Unit 3 | (ratio) | Unit 4 | (ratio) |
|---|---|---|---|---|---|---|---|---|
| P-1 | A-1 | (0.40) | B-1 | (0.50) | B-6 | (0.10) | — | |
| P-2 | A-1 | (0.25) | A-2 | (0.35) | B-1 | (0.30) | B-6 | (0.10) |
| P-3 | A-1 | (0.15) | A-2 | (0.35) | B-4 | (0.50) | — | |
| P-4 | A-4 | (0.50) | B-2 | (0.40) | B-6 | (0.10) | — | |
| P-5 | A-3 | (0.50) | B-1 | (0.50) | — | | — | |
| P-6 | A-3 | (0.50) | B-5 | (0.40) | B-6 | (0.10) | — | |
| P-7 | A-3 | (0.50) | B-1 | (0.20) | B-4 | (0.30) | — | |
| P-8 | A-3 | (0.50) | B-3 | (0.20) | B-4 | (0.30) | — | |
| P-9 | A-2 | (0.25) | A-5 | (0.25) | B-4 | (0.35) | B-6 | (0.15) |
| P-10 | A-3 | (0.25) | A-5 | (0.25) | B-4 | (0.35) | B-6 | (0.15) |
| P-11 | A-3 | (0.25) | A-5 | (0.25) | B-5 | (0.35) | B-6 | (0.15) |
| P-12 | A-5 | (0.30) | A-6 | (0.20) | B-1 | (0.40) | B-6 | (0.10) |
| P-13 | A-1 | (0.15) | A-2 | (0.32) | B-4 | (0.50) | C-1 | (0.03) |
| P-14 | A-1 | (0.15) | A-2 | (0.32) | B-4 | (0.50) | C-2 | (0.03) |

TABLE 2

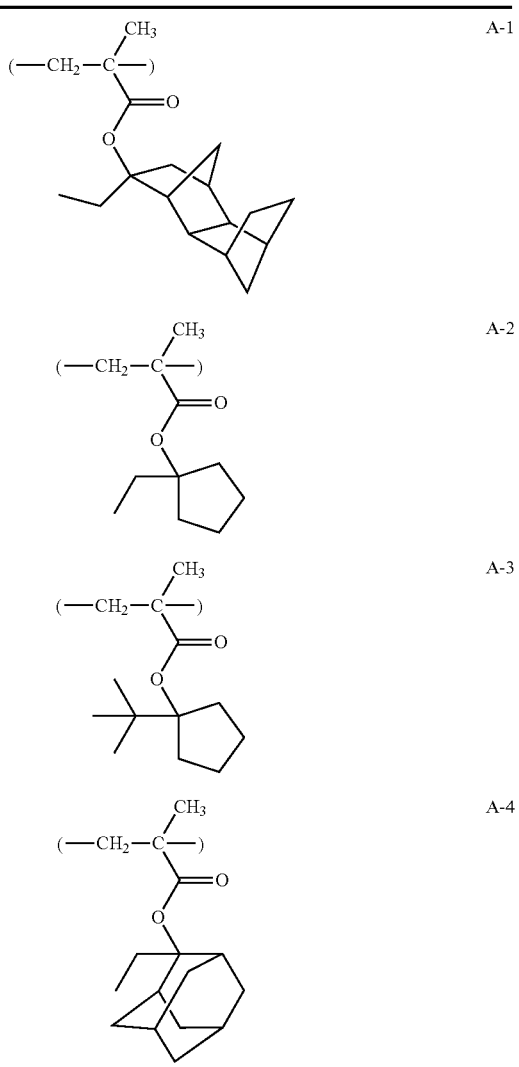

TABLE 2-continued
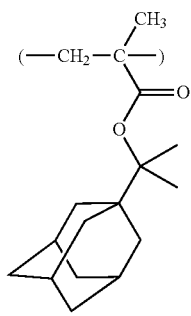
A-5
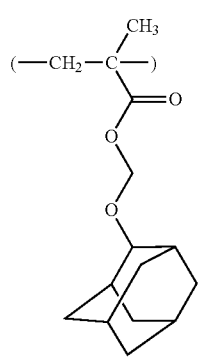
A-6
TABLE 3
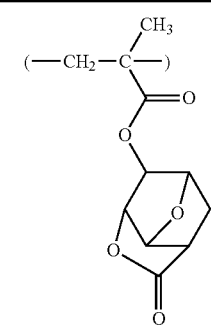
B-1
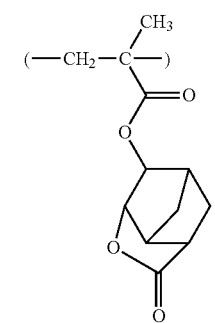
B-2
TABLE 3-continued
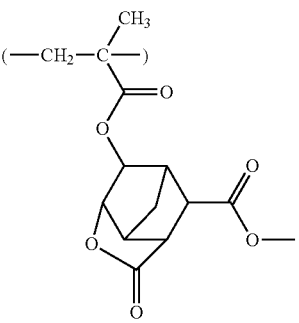
B-3
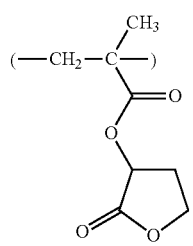
B-4
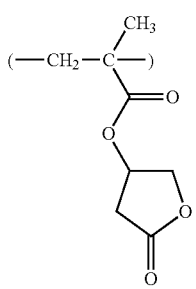
B-5
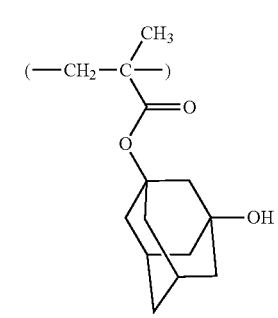
B-6

TABLE 4

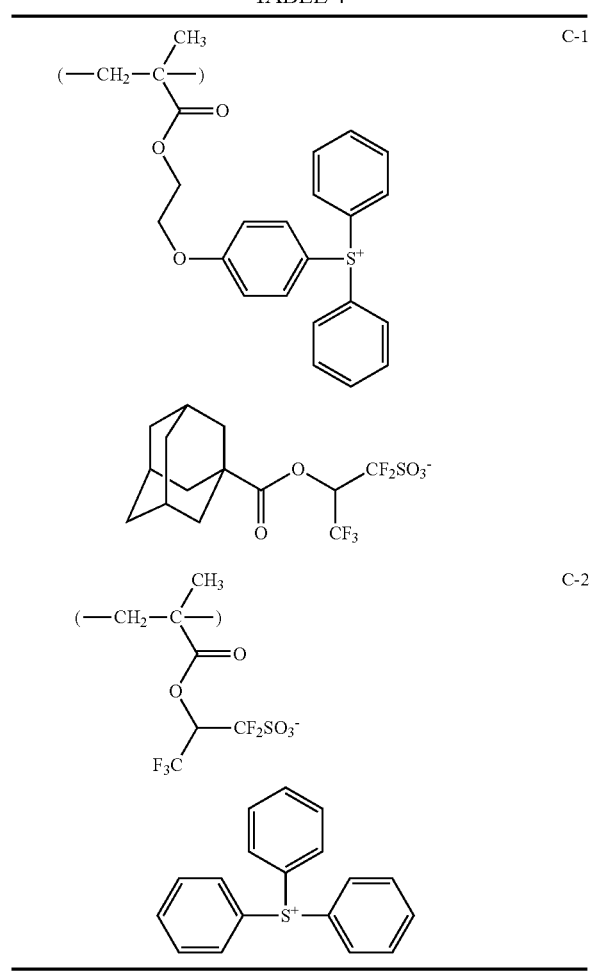

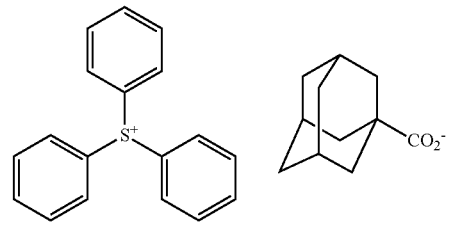
(Q-B)

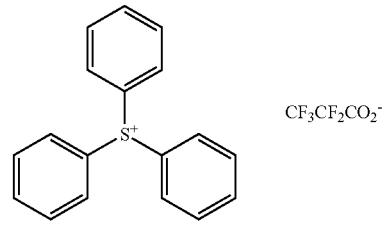
(Q-C)

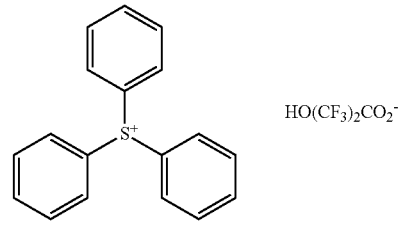
(Q-D)

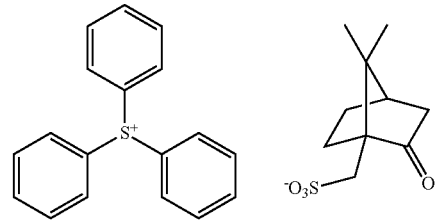
(Q-E)

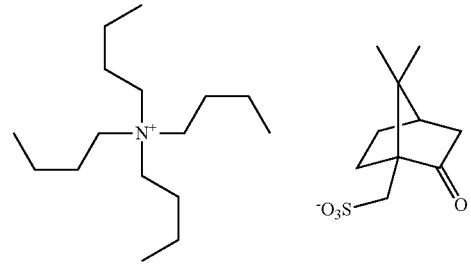
(Q-F)

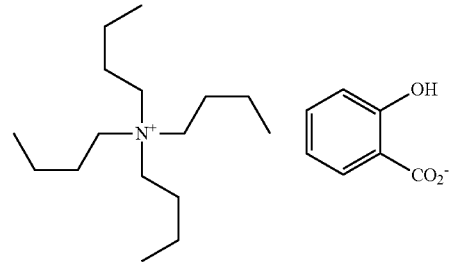
(Q-G)

Examples 1-1 to 1-20 and Comparative Examples 1-1 to 1-7

A resist solution was prepared by selecting a carboxylic acid sulfonium salt (Q-1 to Q-7, prepared in the above Synthesis Examples), polymer, PAG, and alkali-soluble surfactant SF-1 in accordance with the formulation shown in Table 5, dissolving the components in a solvent, and filtering through a Teflon® filter having a pore size of 0.2 μm. The solvent contained 0.01 wt % of surfactant A. A comparative resist solution was prepared by the same procedure aside from using an amine compound or onium salt (Q-A to Q-G) instead of the carboxylic acid sulfonium salt. The formulation of comparative resist solution is also shown in Table 5.

The solvent, PAG, alkali-soluble surfactant SF-1, surfactant A, and comparative quenchers (Q-A to Q-G) in Table 5 are identified below.

PGMEA: propylene glycol monomethyl ether acetate
GBL: γ-butyrolactone
PAG-X: triphenylsulfonium 2-(adamantane-1-carbonyloxy)-1,1,3,3,3-pentafluoropropane-1-sulfonate
PAG-Y: triphenylsulfonium 2-(adamantane-1-carbonyloxy)-3,3,3-trifluoro-2-trifluoromethylpropane-1-sulfonate
Surfactant SF-1: poly(2,2,3,3,4,4,4-heptafluoro-1-isobutyl-1-butyl methacrylate/9-(2,2,2-trifluoro-1-trifluoroethyloxycarbonyl)-4-oxatricyclo-[4.2.1.0$^{3,7}$]nonan-5-on-2-yl methacrylate) of the structural formula shown below

Comparative Quenchers

Q-A: 2-morpholinoethyl laurate (Q-B)
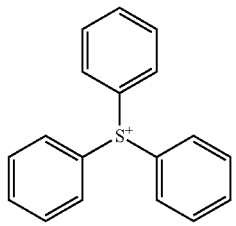 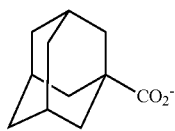

(Q-C)
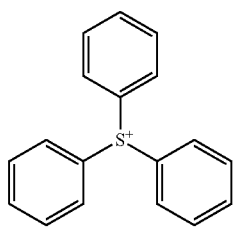 CF$_3$CF$_2$CO$_2^-$ (Q-D)
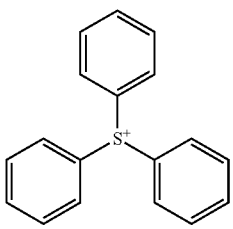 HO(CF$_3$)$_2$CO$_2^-$ (Q-E)
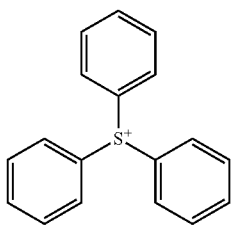 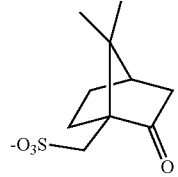

(Q-F)
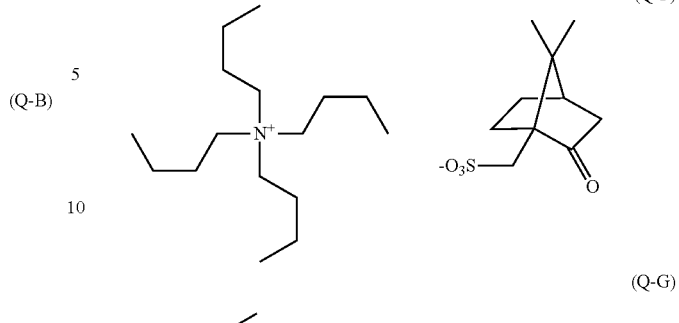

(Q-G)
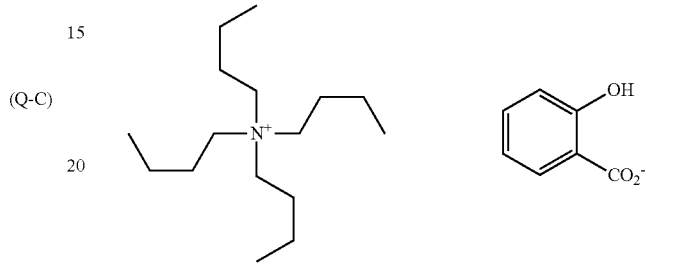

Surfactant A: 3-methyl-3-(2,2,2-trifluoroethoxymethyl)-oxetane/tetrahydrofuran/2,2-dimethyl-1,3-propanediol copolymer (Omnova Solutions, Inc.) of the structural formula shown below

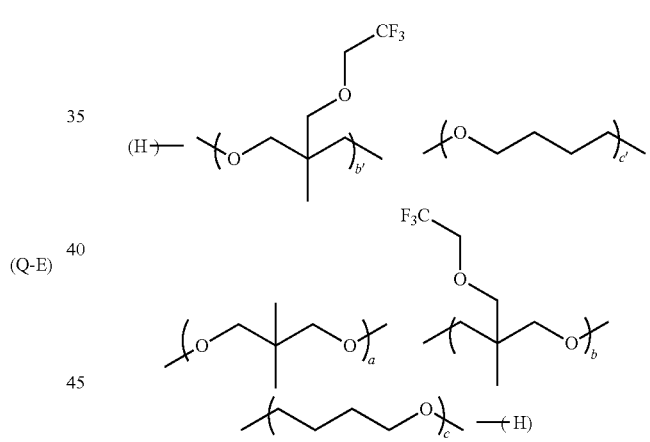

a:(b+b'):(c+c')=1:4-7:0.01-1 (molar ratio)
Mw=1,500

TABLE 5

|  |  | Resist | Resin (pbw) | PAG (pbw) | Quencher (pbw) | Surfactant (pbw) | Solvent 1 (pbw) | Solvent 2 (pbw) |
|---|---|---|---|---|---|---|---|---|
| Example | 1-1 | R-1 | P-1(80) | PAG-X(7.6) | Q-1(4.6) | SF-1(3.0) | PGMEA(1,728) | GBL(192) |
|  | 1-2 | R-2 | P-1(80) | PAG-X(7.6) | Q-2(5.0) | SF-1(3.0) | PGMEA(1,728) | GBL(192) |
|  | 1-3 | R-3 | P-1(80) | PAG-X(7.6) | Q-3(4.9) | SF-1(3.0) | PGMEA(1,728) | GBL(192) |
|  | 1-4 | R-4 | P-1(80) | PAG-X(7.6) | Q-4(5.3) | SF-1(3.0) | PGMEA(1,728) | GBL(192) |
|  | 1-5 | R-5 | P-1(80) | PAG-X(7.6) | Q-5(3.9) | SF-1(3.0) | PGMEA(1,728) | GBL(192) |
|  | 1-6 | R-6 | P-1(80) | PAG-X(7.6) | Q-6(4.1) | SF-1(3.0) | PGMEA(1,728) | GBL(192) |
|  | 1-7 | R-7 | P-1(80) | PAG-X(7.6) | Q-7(4.2) | SF-1(3.0) | PGMEA(1,728) | GBL(192) |
|  | 1-8 | R-8 | P-2(80) | PAG-X(7.6) | Q-1(4.6) | SF-1(3.0) | PGMEA(1,728) | GBL(192) |
|  | 1-9 | R-9 | P-3(80) | PAG-X(7.6) | Q-1(4.6) | SF-1(3.0) | PGMEA(1,728) | GBL(192) |
|  | 1-10 | R-10 | P-4(80) | PAG-X(7.6) | Q-1(4.6) | SF-1(3.0) | PGMEA(1,728) | GBL(192) |
|  | 1-11 | R-11 | P-5(80) | PAG-Y(13.3) | Q-1(4.6) | SF-1(3.0) | PGMEA(1,728) | GBL(192) |
|  | 1-12 | R-12 | P-6(80) | PAG-Y(13.3) | Q-1(4.6) | SF-1(3.0) | PGMEA(1,728) | GBL(192) |
|  | 1-13 | R-13 | P-7(80) | PAG-Y(13.3) | Q-1(4.6) | SF-1(3.0) | PGMEA(1,728) | GBL(192) |
|  | 1-14 | R-14 | P-8(80) | PAG-Y(13.3) | Q-1(4.6) | SF-1(3.0) | PGMEA(1,728) | GBL(192) |

TABLE 5-continued

|   |  | Resist | Resin (pbw) | PAG (pbw) | Quencher (pbw) | Surfactant (pbw) | Solvent 1 (pbw) | Solvent 2 (pbw) |
|---|---|---|---|---|---|---|---|---|
|   | 1-15 | R-15 | P-9(80) | PAG-X(7.6) | Q-1(4.6) | SF-1(3.0) | PGMEA(1,728) | GBL(192) |
|   | 1-16 | R-16 | P-10(80) | PAG-X(7.6) | Q-1(4.6) | SF-1(3.0) | PGMEA(1,728) | GBL(192) |
|   | 1-17 | R-17 | P-11(80) | PAG-X(7.6) | Q-1(4.6) | SF-1(3.0) | PGMEA(1,728) | GBL(192) |
|   | 1-18 | R-18 | P-12(80) | PAG-X(7.6) | Q-1(4.6) | SF-1(3.0) | PGMEA(1,728) | GBL(192) |
|   | 1-19 | R-19 | P-13(80) | — | Q-1(4.6) | SF-1(3.0) | PGMEA(1,728) | GBL(192) |
|   | 1-20 | R-20 | P-14(80) | — | Q-1(4.6) | SF-1(3.0) | PGMEA(1,728) | GBL(192) |
| Comparative | 1-1 | R-21 | P-1(80) | PAG-X(7.6) | Q-A(1.7) | SF-1(3.0) | PGMEA(1,728) | GBL(192) |
| Example | 1-2 | R-22 | P-1(80) | PAG-X(7.6) | Q-B(3.4) | SF-1(3.0) | PGMEA(1,728) | GBL(192) |
|   | 1-3 | R-23 | P-1(80) | PAG-X(7.6) | Q-C(3.3) | SF-1(3.0) | PGMEA(1,728) | GBL(192) |
|   | 1-4 | R-24 | P-1(80) | PAG-X(7.6) | Q-D(3.7) | SF-1(3.0) | PGMEA(1,728) | GBL(192) |
|   | 1-5 | R-25 | P-1(80) | PAG-X(7.6) | Q-E(3.8) | SF-1(3.0) | PGMEA(1,728) | GBL(192) |
|   | 1-6 | R-26 | P-1(80) | PAG-X(7.6) | Q-F(3.7) | SF-1(3.0) | PGMEA(1,728) | GBL(192) |
|   | 1-7 | R-27 | P-1(80) | PAG-X(7.6) | Q-G(2.9) | SF-1(3.0) | PGMEA(1,728) | GBL(192) |

Examples 2-1 to 2-20 and Comparative Examples 2-1 to 2-7

Resist Patterning by ArF Lithography 1

An antireflective coating solution (ARC-29A by Nissan Chemical Industries, Ltd.) was coated onto a silicon substrate and baked at 200° C. for 60 seconds to form an ARC film of 100 nm thick. The resist solution in Table 5 was spin coated onto the ARC and baked on a hot plate at 100° C. for 60 seconds to form a resist film of 90 nm thick. The resist film was exposed according to the ArF immersion lithography using an ArF excimer laser scanner (model NSR-S610C, Nikon Corp., NA 1.30, dipole illumination, Cr mask). The resist film was baked (PEB) at 80° C. for 60 seconds and developed in a 2.38 wt % tetramethylammonium hydroxide aqueous solution for 60 seconds.

Evaluation Method

The resist was evaluated by observing a 40-nm 1:1 line-and-space pattern under an electron microscope. The optimum dose (Eop) was a dose (mJ/cm²) which provided a line width of 40 nm. The profile of a pattern at the optimum dose was compared and judged good or poor.

The width of lines of a 40-nm 1:1 line-and-space pattern was measured under SEM to determine a line width variation (30 points measured, $3\sigma$ value computed), which was reported as line width roughness (LWR). A smaller value of LWR indicates a line pattern with a less fluctuation and of better profile. In this test, the sample is rated good when LWR is equal to or less than 3.0 nm and poor when LWR is equal to or more than 3.1 nm.

Defects in the pattern as developed were inspected by a flaw detector KLA2800 (KLA-Tencor). A defect density (count/cm²) was computed by dividing the total number of detected defects by a detection area. The pattern formed was an iterated 40-nm 1:1 line-and-space pattern. The defect inspection conditions included light source UV, inspected pixel size 0.28 μm, and cell-to-cell mode. In this test, the sample was rated good for a defect density of less than 0.05 defect/cm² and poor for a density of equal to or more than 0.05 defect/cm².

The collapse limit was a minimum width (nm) of lines which could be resolved without collapse when the line width was reduced by increasing the exposure dose. A smaller value indicates better collapse resistance.

The test results of the resist compositions are shown in Table 6.

TABLE 6

|   |   | Resist | Eop (mJ/cm³) | Pattern profile | LWR (nm) | Defect density (count/cm³) | Collapse limit (nm) |
|---|---|---|---|---|---|---|---|
| Example | 2-1 | R-1 | 35 | rectangular | 2.7 | 0.03 | 29 |
|   | 2-2 | R-2 | 37 | rectangular | 2.9 | 0.02 | 30 |
|   | 2-3 | R-3 | 35 | rectangular | 2.8 | 0.03 | 32 |
|   | 2-4 | R-4 | 37 | rectangular | 3.0 | 0.03 | 32 |
|   | 2-5 | R-5 | 36 | rectangular | 2.6 | 0.02 | 28 |
|   | 2-6 | R-6 | 37 | rectangular | 2.8 | 0.02 | 30 |
|   | 2-7 | R-7 | 37 | rectangular | 2.8 | 0.02 | 29 |
|   | 2-8 | R-8 | 35 | rectangular | 2.9 | 0.03 | 28 |
|   | 2-9 | R-9 | 35 | rectangular | 2.7 | 0.02 | 28 |
|   | 2-10 | R-10 | 38 | rectangular | 3.0 | 0.04 | 33 |
|   | 2-11 | R-11 | 32 | rectangular | 2.9 | 0.04 | 32 |
|   | 2-12 | R-12 | 30 | rectangular | 2.6 | 0.02 | 28 |
|   | 2-13 | R-13 | 31 | rectangular | 2.8 | 0.03 | 29 |
|   | 2-14 | R-14 | 32 | rectangular | 2.8 | 0.04 | 29 |
|   | 2-15 | R-15 | 40 | rectangular | 3.0 | 0.03 | 30 |
|   | 2-16 | R-16 | 38 | rectangular | 2.8 | 0.02 | 28 |
|   | 2-17 | R-17 | 38 | rectangular | 2.9 | 0.02 | 29 |
|   | 2-18 | R-18 | 38 | rectangular | 3.0 | 0.04 | 32 |
|   | 2-19 | R-19 | 48 | rectangular | 3.0 | 0.04 | 30 |
|   | 2-20 | R-20 | 41 | rectangular | 2.8 | 0.04 | 28 |
| Comparative | 2-1 | R-21 | 38 | poor, T-top | 3.5 | 0.07 | 38 |
| Example | 2-2 | R-22 | 37 | poor, some footing | 3.4 | 0.07 | 40 |
|   | 2-3 | R-23 | 34 | poor, some footing | 3.3 | 0.08 | 42 |
|   | 2-4 | R-24 | 35 | poor, some footing | 3.1 | 0.06 | 36 |
|   | 2-5 | R-25 | 33 | poor, footing | 3.2 | 0.06 | 38 |

TABLE 6-continued

|  | Resist | Eop (mJ/cm³) | Pattern profile | LWR (nm) | Defect density (count/cm³) | Collapse limit (nm) |
|---|---|---|---|---|---|---|
| 2-6 | R-26 | 34 | poor, footing | 3.3 | 0.07 | 40 |
| 2-7 | R-27 | 36 | poor, some footing | 3.3 | 0.08 | 42 |

It is evident from the data of Table 6 that the resist compositions within the scope of the invention form patterns of good profile having a high resolution, minimal LWR, and low defect density. They are thus best suited as the ArF immersion lithography material.

Examples 3-1 to 3-20 and Comparative Examples 3-1 to 3-7

Resist Patterning by ArF Lithography 2

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition in Table 5 was spin coated, then baked on a hot plate at 100° C. for 60 seconds to form a resist film of 100 nm thick. Using an ArF excimer laser immersion lithography scanner NSR-610C (Nikon Corp., NA 1.30, σ 0.98/0.78, 4/5 annular illumination), pattern exposure was performed through Mask A or B described below.

Mask A is a 6% halftone phase shift mask bearing a line pattern with a pitch of 100 nm and a line width of 50 nm (on-wafer size). After exposure through Mask A, the wafer was baked (PEB) for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask A were dissolved in the developer, that is, image reversal took place to form a line-and-space (L/S) pattern with a space width of 50 nm and a pitch of 100 nm.

Mask B is a 6% halftone phase shift mask bearing a line pattern with a pitch of 200 nm and a line width of 45 nm (on-wafer size). After exposure through Mask B, the wafer was baked (PEB) for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask B were dissolved in the developer, that is, image reversal took place to form an isolated space pattern (referred to as "trench pattern", hereinafter) with a space width of 45 nm and a pitch of 200 nm.

Evaluation of Sensitivity

As an index of sensitivity, the optimum dose (Eop, mJ/cm²) which provided an L/S pattern with a space width of 50 nm and a pitch of 100 nm on exposure through Mask A was determined.

Evaluation of Exposure Latitude (EL)

The exposure dose which provided an L/S pattern with a space width of 50 nm±10% (i.e., 45 nm to 55 nm) on exposure through Mask A was determined. EL (%) is calculated from the exposure doses according to the following equation:

$$EL(\%) = (|E1 - E2|/Eop) \times 100$$

wherein E1 is an exposure dose which provides an L/S pattern with a space width of 45 nm and a pitch of 100 nm, E2 is an exposure dose which provides an L/S pattern with a space width of 55 nm and a pitch of 100 nm, and Eop is the optimum exposure dose which provides an L/S pattern with a space width of 50 nm and a pitch of 100 nm.

Evaluation of Line Width Roughness (LWR)

An L/S pattern was formed by exposure in the optimum dose (determined in the sensitivity evaluation) through Mask A (in ArF lithography patterning test 2). By observation under TDSEM S-9380 (Hitachi Hitechnologies, Ltd.), the space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of Mask Error Factor (MEF)

An L/S pattern was formed by exposure in the optimum dose (determined in the sensitivity evaluation) through Mask A with the pitch fixed and the line width varied. MEF was calculated from variations of the mask line width and the pattern space width according to the following equation:

$$MEF = (\text{pattern space width})/(\text{mask line width}) - b$$

wherein b is a constant. A value closer to unity (1) indicates better performance.

Evaluation of Depth-of-Focus (DOF) Margin

The exposure dose and DOF which ensured to form a trench pattern with a space width of 35 nm on exposure through Mask B were defined as the optimum exposure dose and the optimum DOF, respectively. The depth (μm) over which focus was changed that could form a resist pattern with a space width of 35 nm±10% (i.e., 31.5 nm to 38.5 nm) was determined and reported as DOF. A larger value indicates a smaller change of pattern size with a change of DOF and hence, better DOF margin.

The results are shown in Table 7.

TABLE 7

|  |  | Resist | Eop (mJ/cm³) | EL (%) | LWR (nm) | MEF | DOP (nm) |
|---|---|---|---|---|---|---|---|
| Example | 3-1 | R-1 | 28 | 17 | 3.1 | 3.2 | 140 |
|  | 3-2 | R-2 | 34 | 19 | 3.4 | 2.9 | 130 |
|  | 3-3 | R-3 | 30 | 16 | 3.2 | 3.3 | 140 |
|  | 3-4 | R-4 | 35 | 18 | 3.5 | 3.0 | 120 |
|  | 3-5 | R-5 | 29 | 17 | 3.1 | 3.0 | 130 |
|  | 3-6 | R-6 | 31 | 18 | 3.3 | 3.1 | 120 |
|  | 3-7 | R-7 | 31 | 18 | 3.4 | 3.0 | 120 |
|  | 3-8 | R-8 | 29 | 17 | 3.4 | 2.9 | 140 |
|  | 3-9 | R-9 | 28 | 16 | 3.3 | 3.1 | 130 |
|  | 3-10 | R-10 | 32 | 18 | 3.5 | 2.9 | 120 |
|  | 3-11 | R-11 | 32 | 17 | 3.4 | 3.1 | 150 |
|  | 3-12 | R-12 | 27 | 16 | 3.0 | 3.3 | 140 |
|  | 3-13 | R-13 | 29 | 17 | 3.1 | 3.2 | 150 |
|  | 3-14 | R-14 | 29 | 16 | 3.2 | 3.4 | 130 |
|  | 3-15 | R-15 | 34 | 18 | 3.5 | 2.8 | 120 |
|  | 3-16 | R-16 | 32 | 17 | 3.2 | 3.0 | 140 |
|  | 3-17 | R-17 | 31 | 17 | 3.3 | 2.9 | 150 |
|  | 3-18 | R-18 | 32 | 16 | 3.5 | 3.3 | 120 |
|  | 3-19 | R-19 | 41 | 18 | 3.3 | 3.0 | 120 |

TABLE 7-continued

|  |  | Resist | Eop (mJ/cm$^3$) | EL (%) | LWR (nm) | MEF | DOP (nm) |
|---|---|---|---|---|---|---|---|
|  | 3-20 | R-20 | 38 | 19 | 3.1 | 2.8 | 120 |
| Comparative | 3-1 | R-21 | 30 | 13 | 4.2 | 4.1 | 80 |
| Example | 3-2 | R-22 | 29 | 12 | 4.8 | 4.4 | 80 |
|  | 3-3 | R-23 | 28 | 10 | 4.6 | 4.8 | 70 |
|  | 3-4 | R-24 | 28 | 12 | 4.0 | 4.2 | 80 |
|  | 3-5 | R-25 | 26 | 10 | 4.2 | 4.7 | 70 |
|  | 3-6 | R-26 | 28 | 11 | 4.4 | 4.6 | 70 |
|  | 3-7 | R-27 | 30 | 12 | 4.5 | 4.5 | 80 |

As seen from the results of Table 7, the resist compositions within the scope of the invention form negative patterns via organic solvent development with the advantages of hole size uniformity, improved exposure latitude, LWR and MEF of L/S patterns, and improved DOF margin of trench patterns. The compositions are advantageously applicable to the organic solvent development process.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

Japanese Patent Application No. 2013-188086 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the general formula (1):

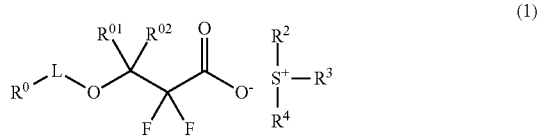

wherein $R^0$ is hydrogen, or a straight $C_1$-$C_{20}$ or branched or cyclic $C_3$-$C_{20}$ monovalent hydrocarbon group which may be substituted with or separated by a heteroatom, $R^{01}$ and $R^{02}$ are each independently hydrogen, or a straight $C_1$-$C_{20}$ or branched or cyclic $C_3$-$C_{20}$ monovalent hydrocarbon group which may be substituted with or separated by a heteroatom, or $R^{01}$ and $R^{02}$ may bond together to form a ring with the carbon atom to which they are attached, with the proviso that at least one of $R^0$, $R^{01}$ and $R^{02}$ has a cyclic structure, L is a single bond or forms an ester bond, sulfonate bond, carbonate bond or carbamate bond with the vicinal oxygen atom, $R^2$, $R^3$ and $R^4$ are each independently a straight $C_1$-$C_{20}$ or branched or cyclic $C_3$-$C_{20}$ monovalent hydrocarbon group which may be substituted with or separated by a heteroatom, at least two of $R^2$, $R^3$ and $R^4$ may bond together to form a ring with the sulfur atom in the formula.

2. The sulfonium salt of claim 1 wherein the anion moiety of the formula:

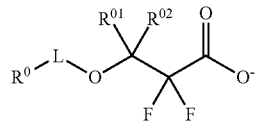

is selected from the following formulae (A-9) to (A-16), (A-27) to (A-34), (A-44) to (A-50), (A-52), and (A-53):

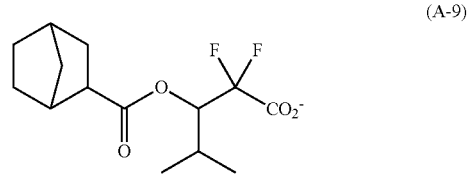

(A-9)

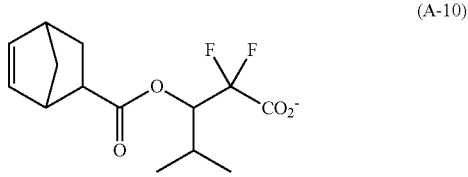

(A-10)

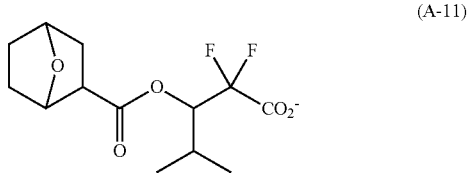

(A-11)

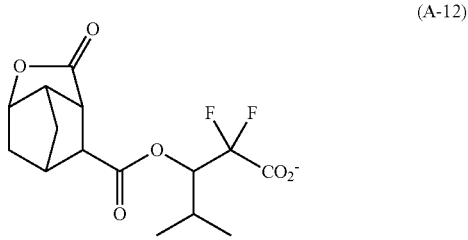

(A-12)

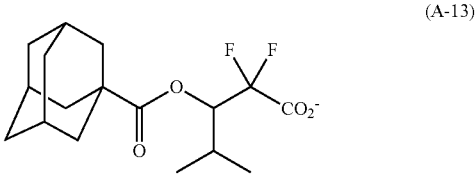

(A-13)

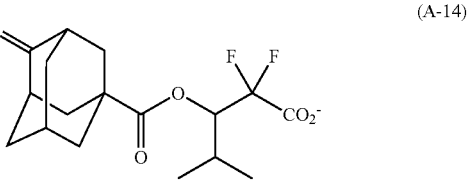

(A-14)

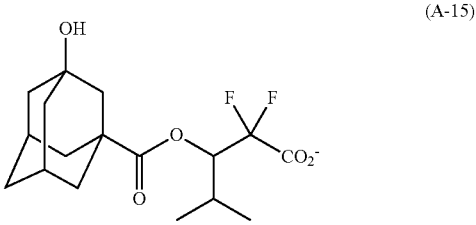

(A-15)

-continued
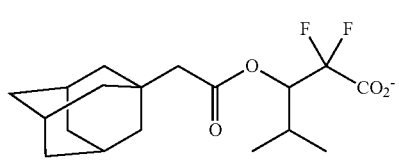
(A-16)
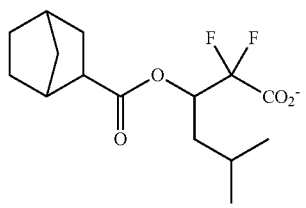
(A-27)
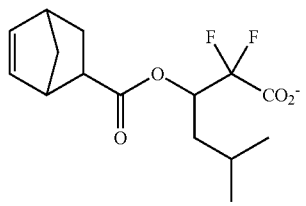
(A-28)
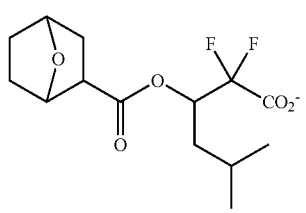
(A-29)
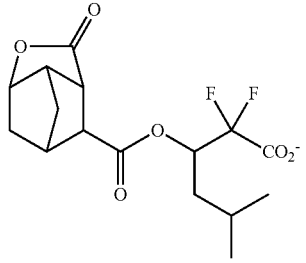
(A-30)
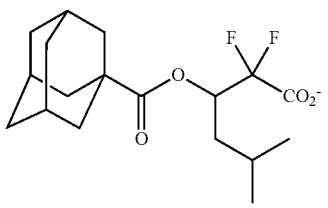
(A-31)
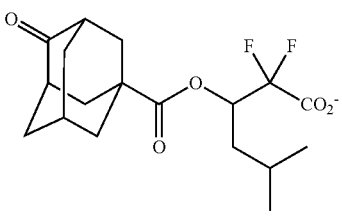
(A-32)
-continued
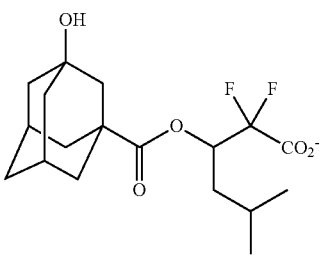
(A-33)
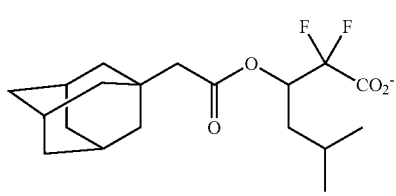
(A-34)
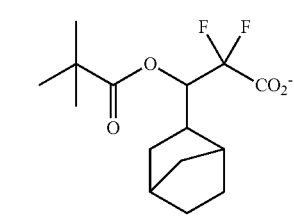
(A-44)
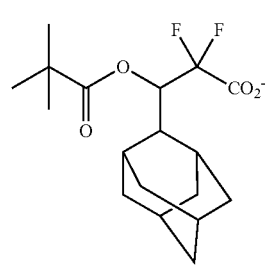
(A-45)
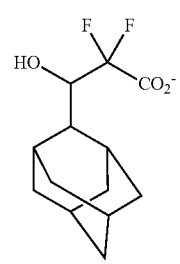
(A-46)
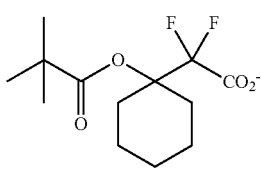
(A-47)
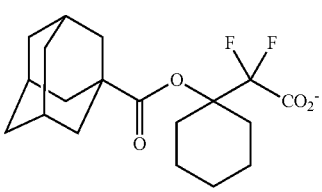
(A-48)

(A-49)
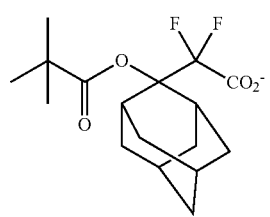
(A-50)
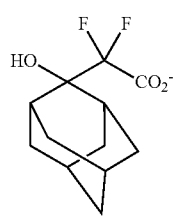
(A-52)
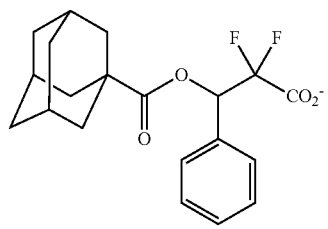
(A-53)
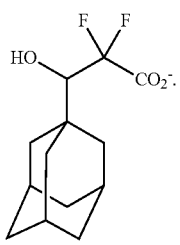
3. The sulfonium salt of claim 1 wherein the cation moiety of the formula:
$$\begin{array}{c} R^2 \\ | \\ S^+ - R^3 \\ | \\ R^4 \end{array}$$
is selected from the following formulae:
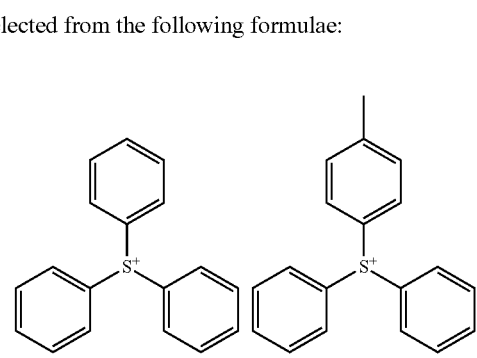
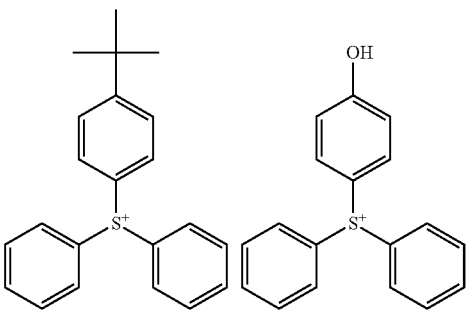
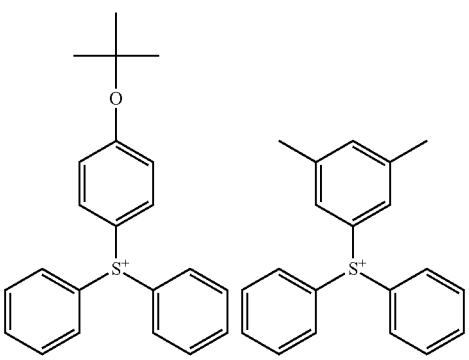
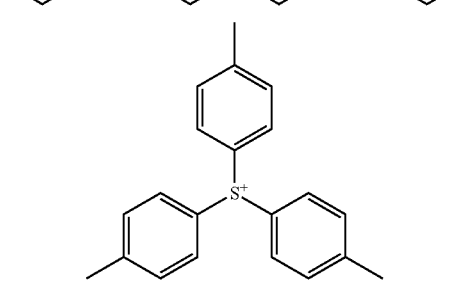
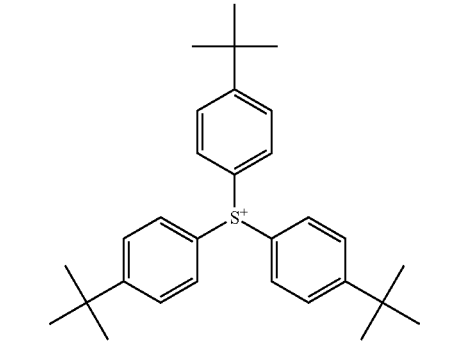
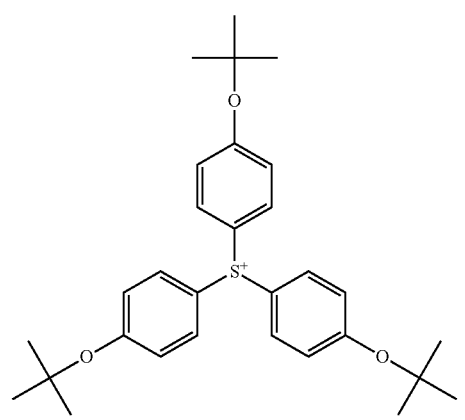

-continued

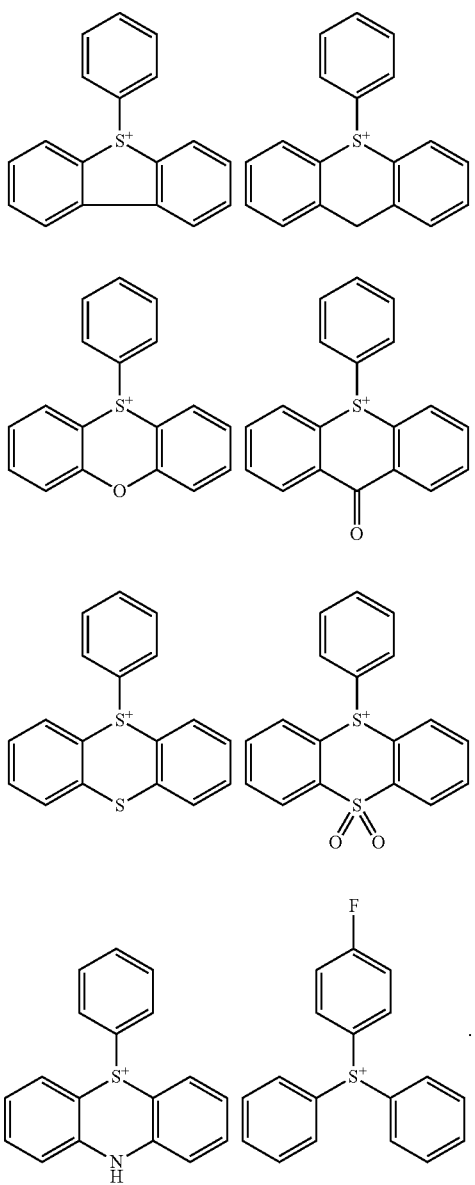

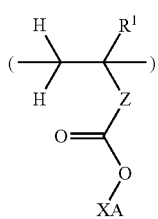

4. A chemically amplified resist composition comprising
(A) the sulfonium salt of claim 1, 2 or 3,
(B) a polymer as a base resin, and
(E) an organic solvent,
said polymer comprising recurring units having the general formulae (2) and (3):

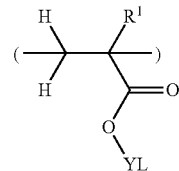
(2)

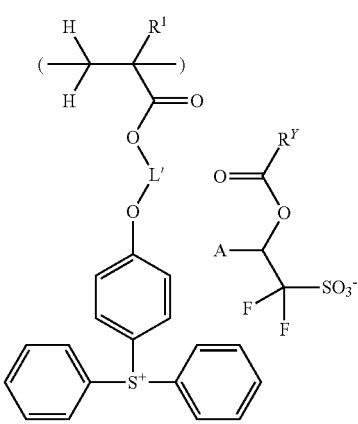
(3)

wherein $R^1$ is hydrogen, fluorine, methyl or trifluoromethyl, Z is a single bond, phenylene, naphthylene or (backbone)-C(=O)—O—Z'—, Z' is a straight $C_1$-$C_{10}$ or branched or cyclic $C_3$-$C_{10}$ alkylene group which may contain a hydroxyl radical, ether bond, ester bond, or lactone ring, or a phenylene or naphthylene group, XA is an acid labile group, and YL is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

5. The resist composition of claim 4 wherein the polymer further comprises recurring units (d1) or (d2) having the general formula:

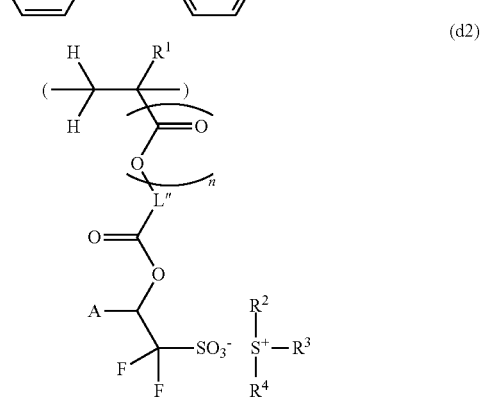
(d1)

(d2)

wherein $R^1$, $R^2$, $R^3$, and $R^4$ are as defined above, L' is a single bond or $C_2$-$C_5$ alkylene group, $R^Y$ is a straight $C_1$-$C_{20}$ or branched or cyclic $C_3$-$C_{20}$ monovalent hydrocarbon group which may be substituted with or separated by a heteroatom, A is hydrogen or trifluoromethyl, L'' is a single bond or a straight $C_1$-$C_{20}$ or branched or cyclic $C_3$-$C_{20}$ divalent hydrocarbon group which may be substituted with or separated by a heteroatom, n is 0 or 1, with the proviso that n is 0 when L'' is a single bond.

6. The resist composition of claim 4, further comprising a photoacid generator having the general formula (4):

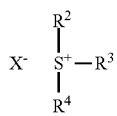
(4)

wherein $R^2$, $R^3$, and $R^4$ are as defined above, $X^-$ is an anion of any one of the general formulae (5) to (8):

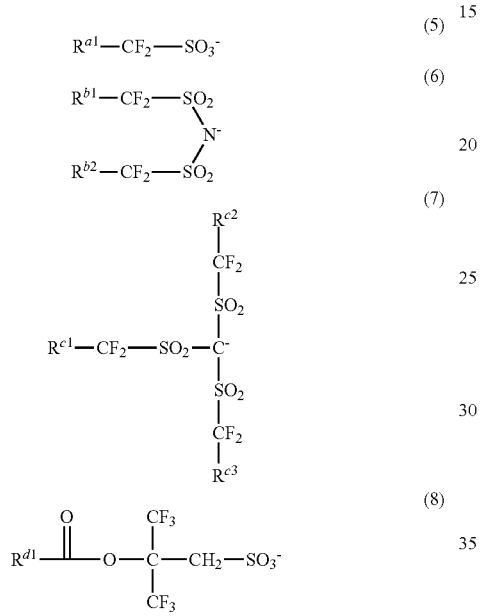

wherein $R^{a1}$, $R^{b1}$, $R^{b2}$, $R^{c1}$, $R^{c2}$, and $R^{c3}$ are each independently fluorine or a straight $C_1$-$C_{40}$ or branched or cyclic $C_3$-$C_{40}$ monovalent hydrocarbon group which may be substituted with or separated by a heteroatom, $R^{b1}$ and $R^{b2}$, or $R^{c1}$ and $R^{c2}$ may bond together to form a ring with —$CF_2$—$SO_2$— group to which they are attached, $R^{d1}$ is a straight $C_1$-$C_{40}$ or branched or cyclic $C_3$-$C_{40}$ monovalent hydrocarbon group which may be substituted with or separated by a heteroatom.

7. The resist composition of claim 4, further comprising a nitrogen-containing compound.

8. The resist composition of claim 4, further comprising surfactant which is insoluble in water and soluble in alkaline developer.

9. A pattern forming process comprising the steps of applying the chemically amplified resist composition of claim 4 onto a substrate, prebaking to form a resist film, exposing the resist film to KrF excimer laser, ArF excimer laser or EUV through a photomask, baking, and developing the exposed resist film in a developer.

10. The pattern forming process of claim 9 wherein the exposing step is by immersion lithography wherein a liquid having a refractive index of at least 1.0 is interposed between the resist film and a projection lens.

11. The pattern forming process of claim 10, further comprising the step of forming a protective film on the resist film, and in the immersion lithography, the liquid is interposed between the protective film and the projection lens.

12. The sulfonium salt of claim 1 wherein $R^{o1}$ is hydrogen, or a straight $C_1$-$C_{20}$ or branched or cyclic $C_3$-$C_{20}$ monovalent hydrocarbon group which may be substituted with or separated by a heteroatom, and $R^{o2}$ is a straight $C_1$-$C_{20}$ or branched or cyclic $C_3$-$C_{20}$ monovalent hydrocarbon group which may be substituted with or separated by a heteroatom.

13. A chemically amplified resist composition comprising
(A) the sulfonium salt of claim 12,
(B) a polymer as a base resin, and
(E) an organic solvent,
said polymer comprising recurring units having the general formulae (2) and (3):

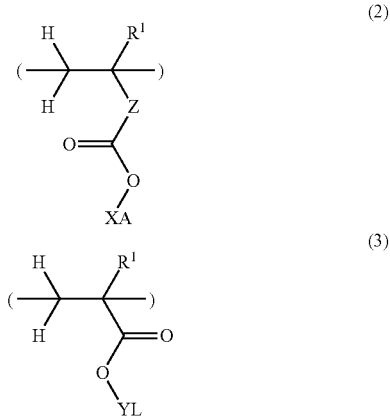

wherein $R^1$ is hydrogen, fluorine, methyl or trifluoromethyl, Z is a single bond, phenylene, naphthylene or (backbone)-C(=O)—O—Z'—, Z' is a straight $C_1$-$C_{10}$ or branched or cyclic $C_3$-$C_{10}$ alkylene group which may contain a hydroxyl radical, ether bond, ester bond, or lactone ring, or a phenylene or naphthylene group, XA is an acid labile group, and YL is hydrogen or a polar group having at least one structure selected from the group consisting of hydroxyl, cyano, carbonyl, carboxyl, ether bond, ester bond, sulfonate bond, carbonate bond, lactone ring, sultone ring, and carboxylic anhydride.

14. The resist composition of claim 13 wherein the polymer further comprises recurring units (d1) or (d2) having the general formula:

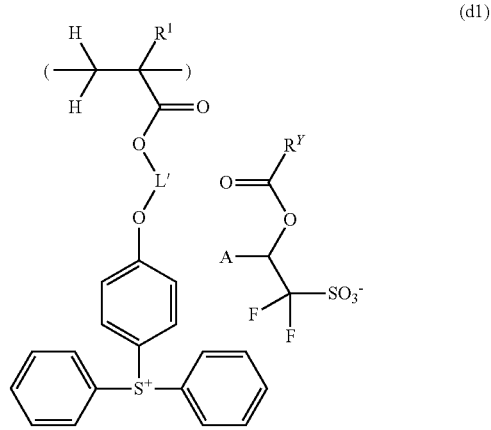

(d2)

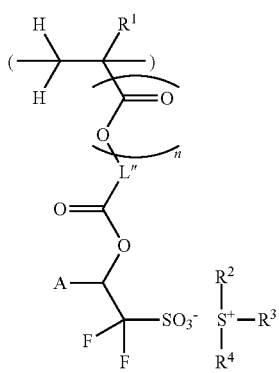

wherein $R^1$, $R^2$, $R^3$, and $R^4$ are as defined above, L' is a single bond or $C_2$-$C_5$ alkylene group, $R^Y$ is a straight $C_1$-$C_{20}$ or branched or cyclic $C_3$-$C_{20}$ monovalent hydrocarbon group which may be substituted with or separated by a heteroatom, A is hydrogen or trifluoromethyl, L" is a single bond or a straight $C_1$-$C_{20}$ or branched or cyclic $C_3$-$C_{20}$ divalent hydrocarbon group which may be substituted with or separated by a heteroatom, n is 0 or 1, with the proviso that n is 0 when L" is a single bond.

15. The resist composition of claim 13, further comprising a photoacid generator having the general formula (4):

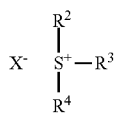 (4)

wherein $R^2$, $R^3$, and $R^4$ are as defined above, $X^-$ is an anion of any one of the general formulae (5) to (8):

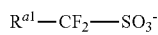 (5)

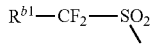 (6)

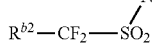

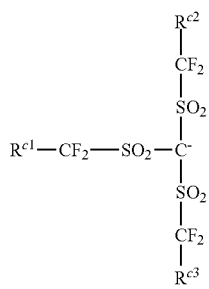 (7)

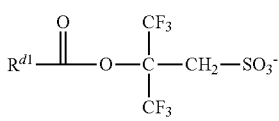 (8)

wherein $R^{a1}$, $R^{b1}$, $R^{b2}$, $R^{c1}$, $R^{c2}$, and $R^{c3}$ are each independently fluorine or a straight $C_1$-$C_{40}$ or branched or cyclic $C_3$-$C_{40}$ monovalent hydrocarbon group which may be substituted with or separated by a heteroatom, $R^{b1}$ and $R^{b2}$, or $R^{c1}$ and $R^{c2}$ may bond together to form a ring with —$CF_2$—$SO_2$— group to which they are attached, $R^{d1}$ is a straight $C_1$-$C_{40}$ or branched or cyclic $C_3$-$C_{40}$ monovalent hydrocarbon group which may be substituted with or separated by a heteroatom.

16. The resist composition of claim 13, further comprising a nitrogen-containing compound.

17. The resist composition of claim 13, further comprising surfactant which is insoluble in water and soluble in alkaline developer.

\* \* \* \* \*